US012714751B2

(12) United States Patent
He

(10) Patent No.: US 12,714,751 B2
(45) Date of Patent: Aug. 25, 2026

(54) LIGHT-INDUCED CELLULAR PRODUCTION OF IMMUNE FUNCTIONAL EXTRACELLULAR VESICLES

(71) Applicant: University of Florida Research Foundation, Incorporated, Gainesville, FL (US)

(72) Inventor: Mei He, Gainesville, FL (US)

(73) Assignee: University of Florida Research Foundation, Incorporated, Gainesville, FL (US)

( * ) Notice: Subject to any disclaimer, the term of this patent is extended or adjusted under 35 U.S.C. 154(b) by 259 days.

(21) Appl. No.: 18/576,793

(22) PCT Filed: Jul. 6, 2022

(86) PCT No.: PCT/US2022/036181
§ 371 (c)(1),
(2) Date: Jan. 5, 2024

(87) PCT Pub. No.: WO2023/283218
PCT Pub. Date: Jan. 12, 2023

(65) Prior Publication Data

US 2025/0090470 A1 Mar. 20, 2025

Related U.S. Application Data

(60) Provisional application No. 63/219,116, filed on Jul. 7, 2021.

(51) Int. Cl.

| | |
|---|---|
| ***A61K 40/24*** | (2025.01) |
| ***A61K 9/50*** | (2006.01) |
| ***A61K 39/00*** | (2006.01) |
| ***A61K 40/19*** | (2025.01) |
| ***A61K 40/40*** | (2025.01) |
| ***A61P 37/04*** | (2006.01) |
| ***C12N 5/0784*** | (2010.01) |
| ***C12N 13/00*** | (2006.01) |

(52) U.S. Cl.
CPC ............ *A61K 40/24* (2025.01); *A61K 9/5068* (2013.01); *A61K 39/0011* (2013.01); *A61K 40/19* (2025.01); *A61K 40/40* (2025.01); *A61P 37/04* (2018.01); *C12N 5/0639* (2013.01); *C12N 13/00* (2013.01)

(58) Field of Classification Search
None
See application file for complete search history.

(56) References Cited

U.S. PATENT DOCUMENTS

| | | | | |
|---|---|---|---|---|
| 2013/0053426 | A1* | 2/2013 | Seow .................. | C12N 15/113 514/44 R |
| 2016/0333317 | A1 | 11/2016 | Chang et al. | |
| 2017/0233766 | A1 | 8/2017 | Matsui et al. | |
| 2019/0160097 | A1 | 5/2019 | Pusic et al. | |
| 2021/0189329 | A1 | 6/2021 | Levenberg et al. | |

FOREIGN PATENT DOCUMENTS

| | | | | |
|---|---|---|---|---|
| CA | 2983731 | A1 | 11/2016 | |
| EP | 3293265 | A1 * | 3/2018 | ............. C07K 19/00 |
| WO | WO 2015/048844 | A1 | 4/2015 | |
| WO | WO 2016/176500 | A1 | 11/2016 | |
| WO | WO 2017/117585 | A1 | 7/2017 | |

OTHER PUBLICATIONS

Thery et al., "Proteomic Analysis of Dendritic Cell-Derived Exosomes: A Secreted Subcellular Compartment Distinct from Apoptotic Vesicles", *The Journal of Immunology*, Jun. 15, 2001, vol. 166, No. 12, pp. 7309-7318.

Schnitzer et al., "Fragments of Antigen-Loaded Dendritic Cells (DC) and DC-derived Exosomes Induce Protective Immunity Against Leishmania Major", *Vaccine*, Jul. 6, 2010, vol. 28, pp. 5785-5793.

Wu et al., "Bone Marrow Dendritic Cells Derived Microvesicles for Combinational Immunochemotherapy against Tumor", *Advanced Functional Materials*. Sep. 13, 2017, vol. 27, No. 42, pp. 1-15.

International Search Report and Written Opinon for Patent Cooperation Treaty Application No. PCT/US2022/036181, dated Oct. 4, 2022, 11 pages.

Ruan, et al., "Light-Induced High-Efficient Cellular Production of Immune Functional Extracellular Vesicles", *JExtracellVesicles*, Mar. 1, 2022, DOI: 10.1002/jev2.12194.

* cited by examiner

*Primary Examiner* — Celeste A Roney
(74) *Attorney, Agent, or Firm* — Alston & Bird LLP

(57) ABSTRACT

Described are method of producing extracellular vesicles from cells by exposing the cells to near UV light. Compositions containing the extracellular vesicles and methods of using the extracellular vesicles are also described.

20 Claims, 51 Drawing Sheets

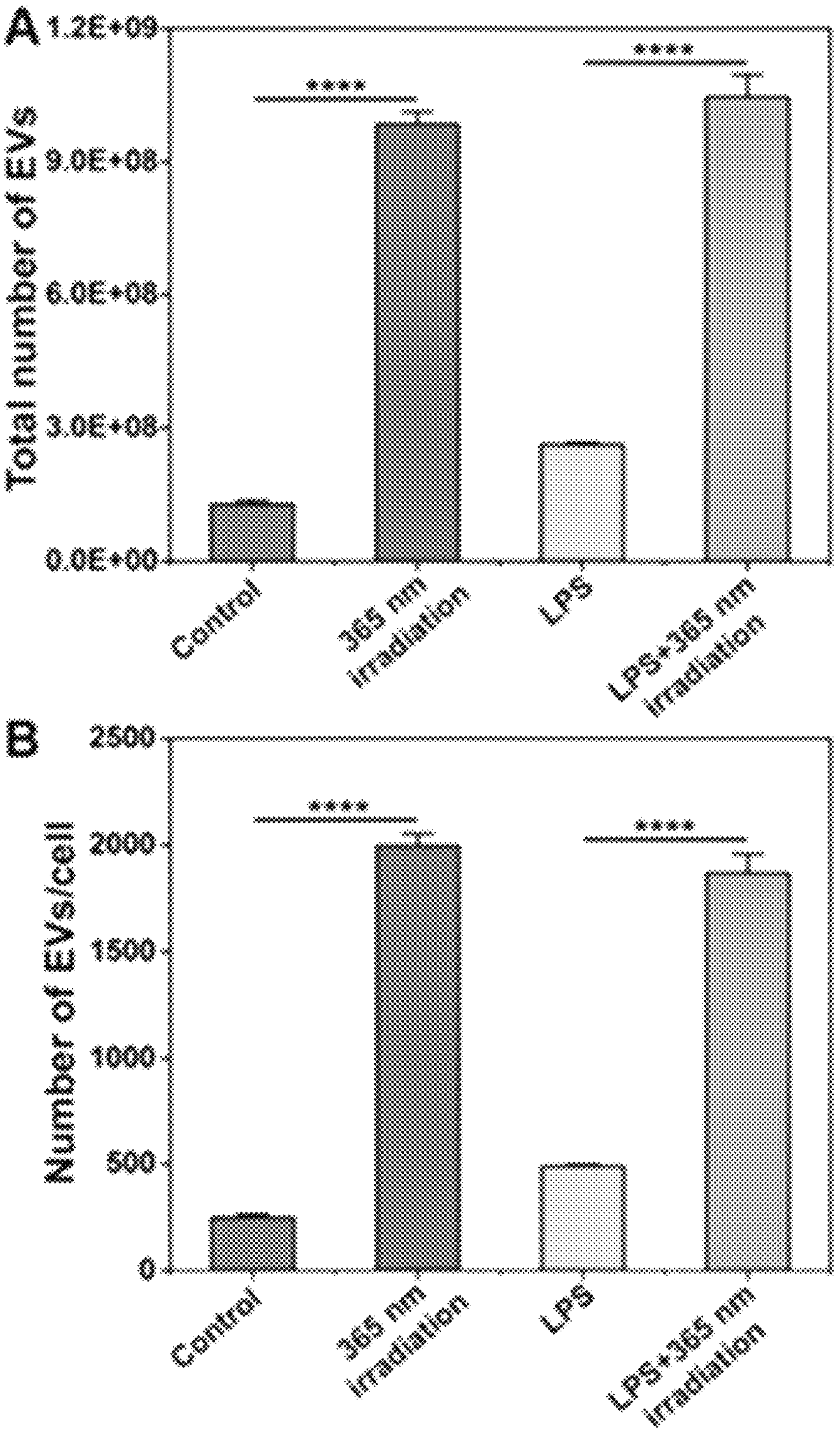
FIG. 1A-B

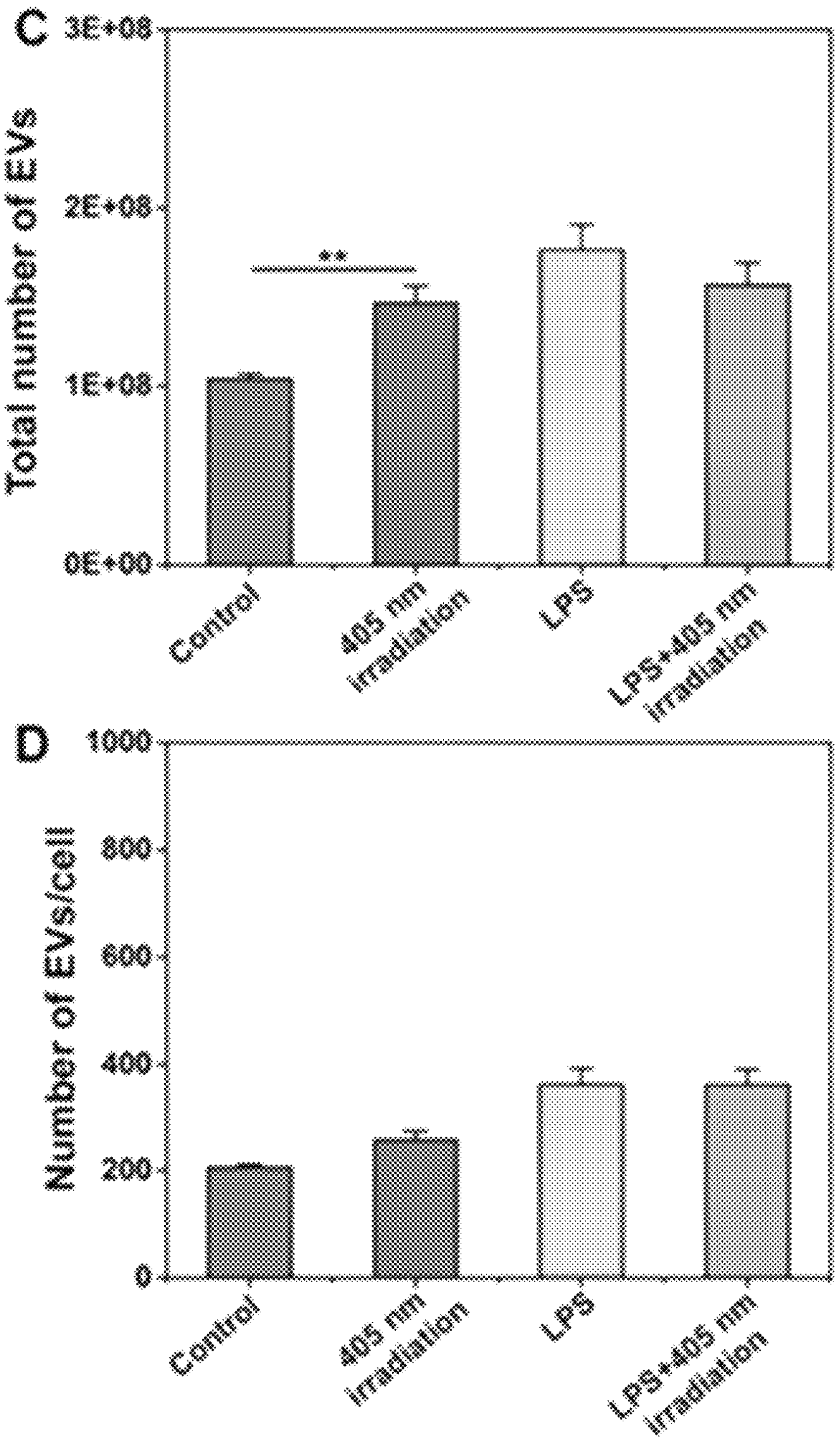
FIG. 1C-D

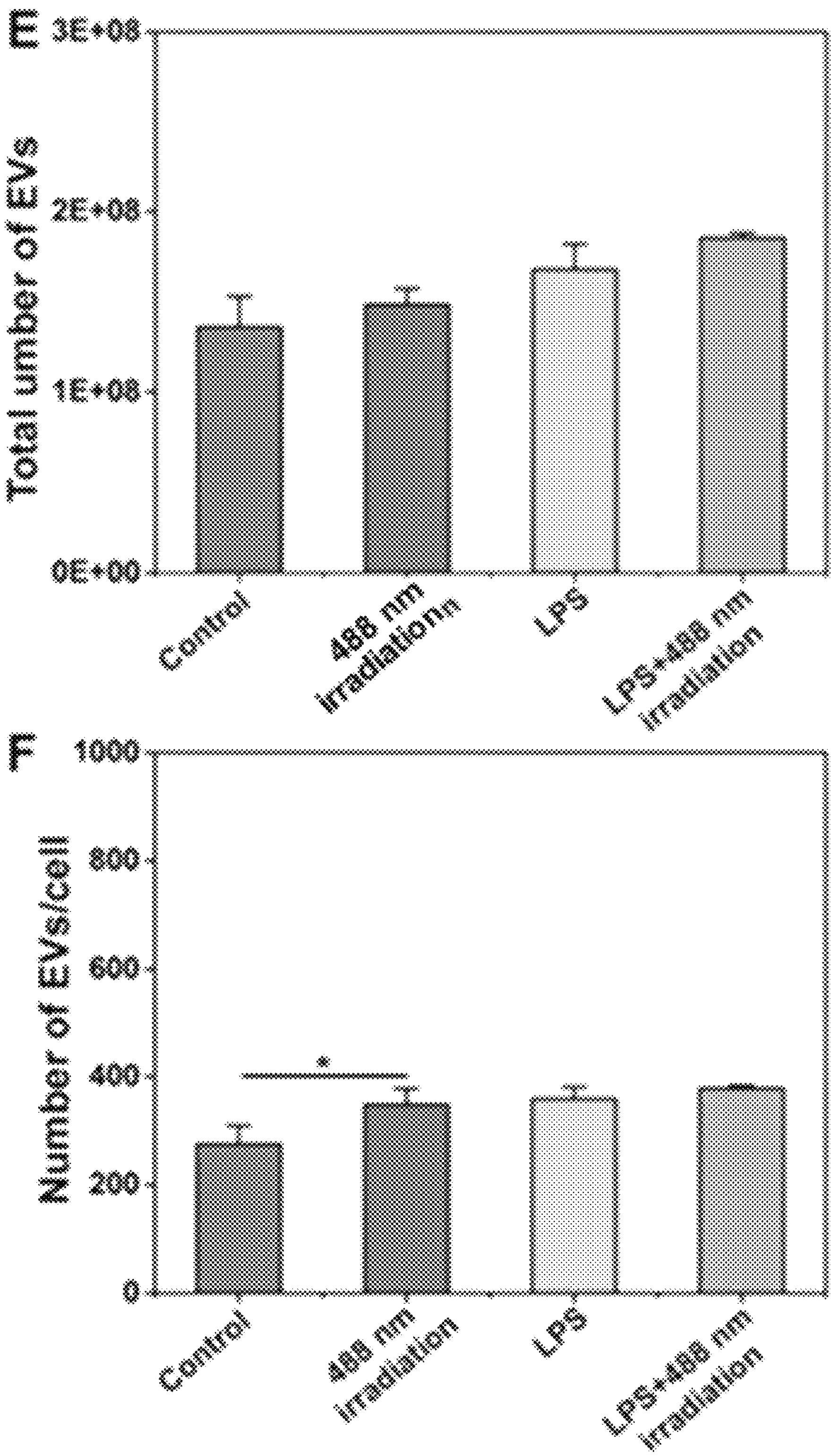
FIG. 1E-F

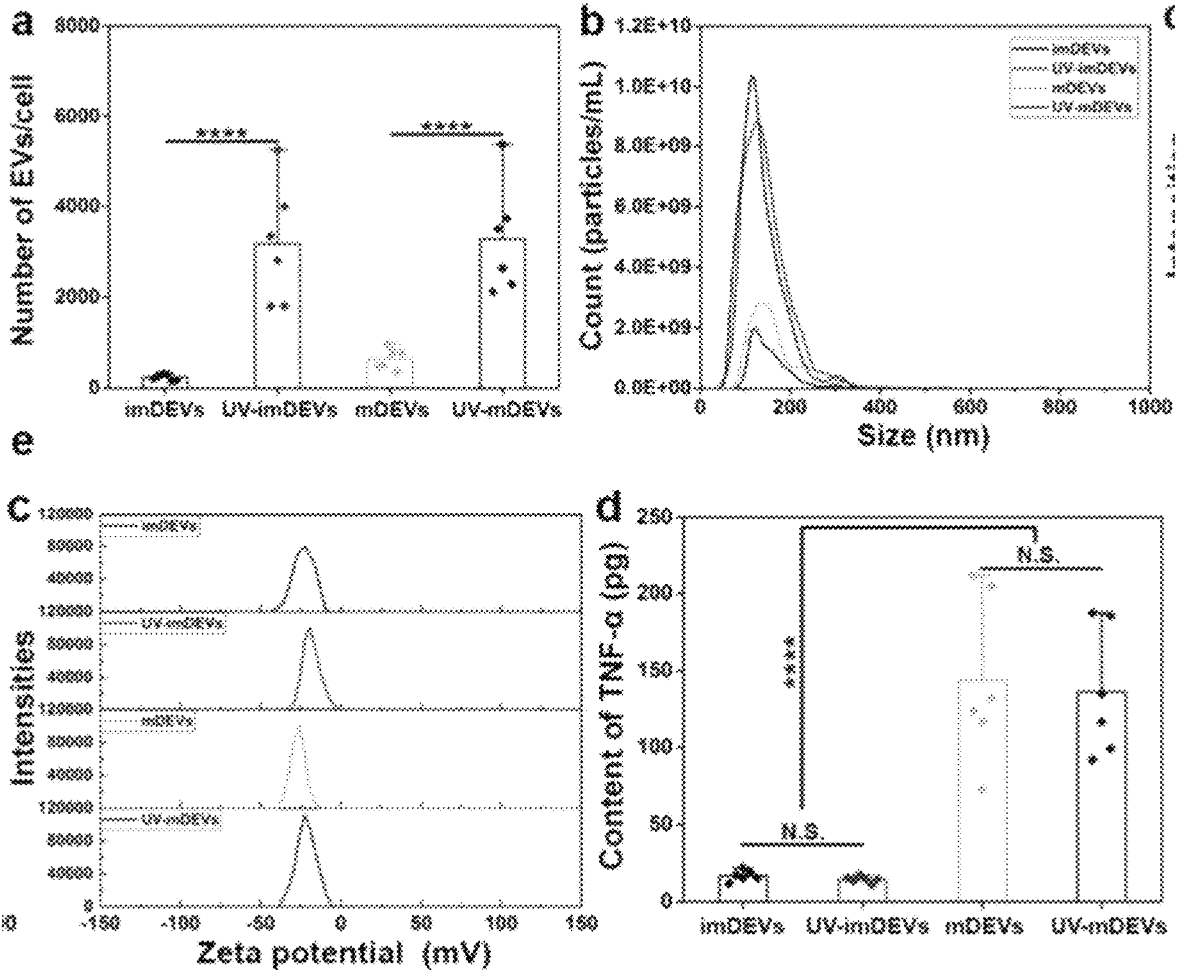
FIG. 5A-D

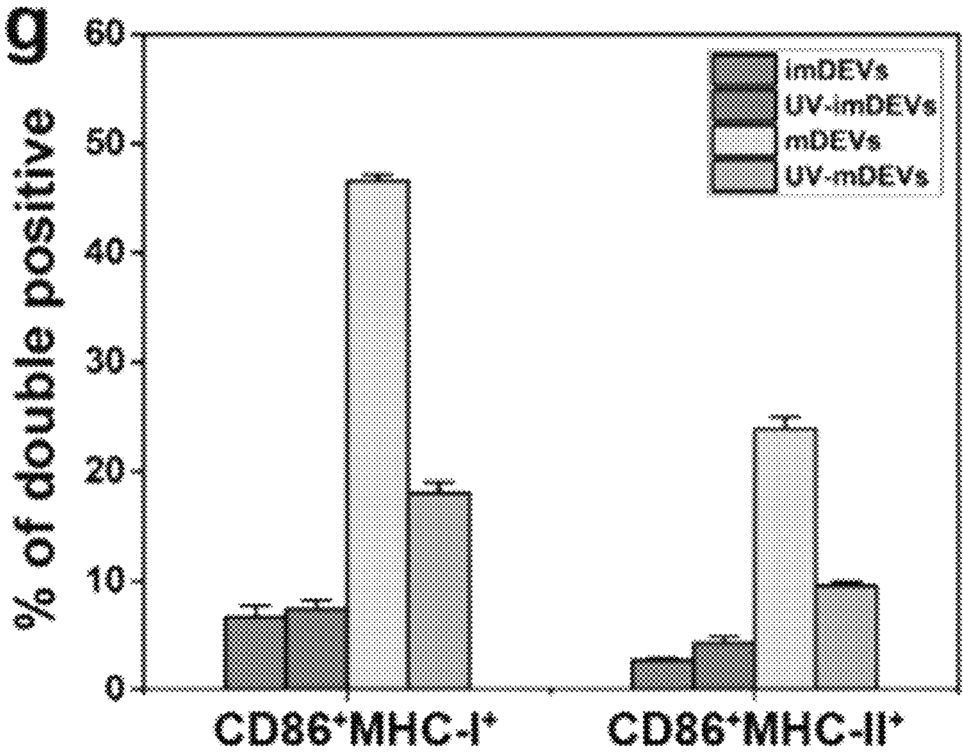
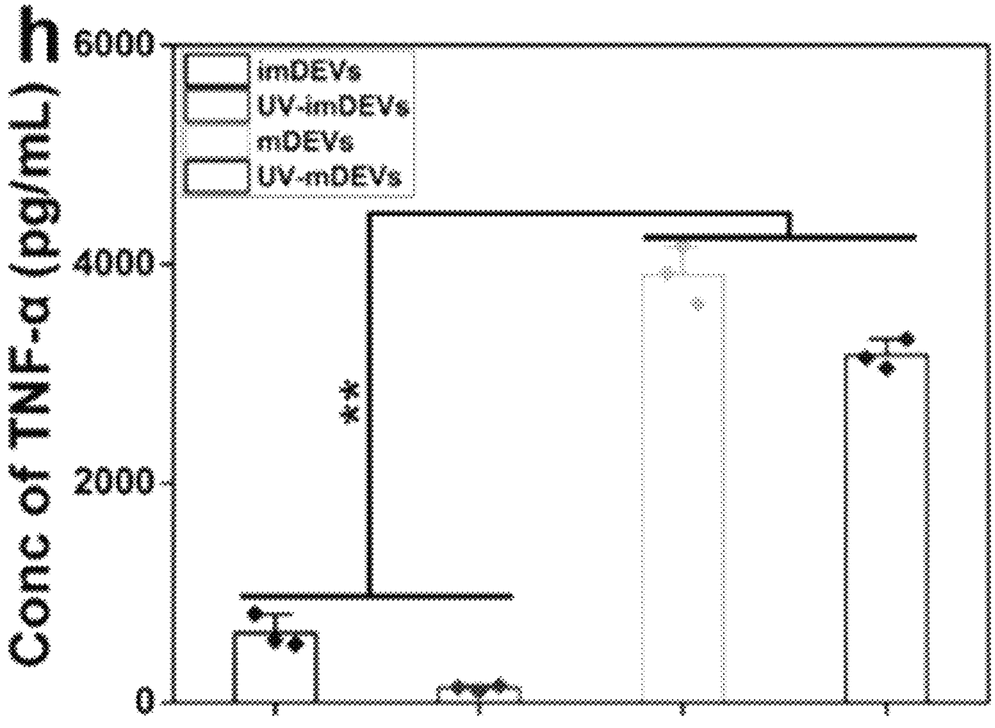
FIG. 5G-H

A.
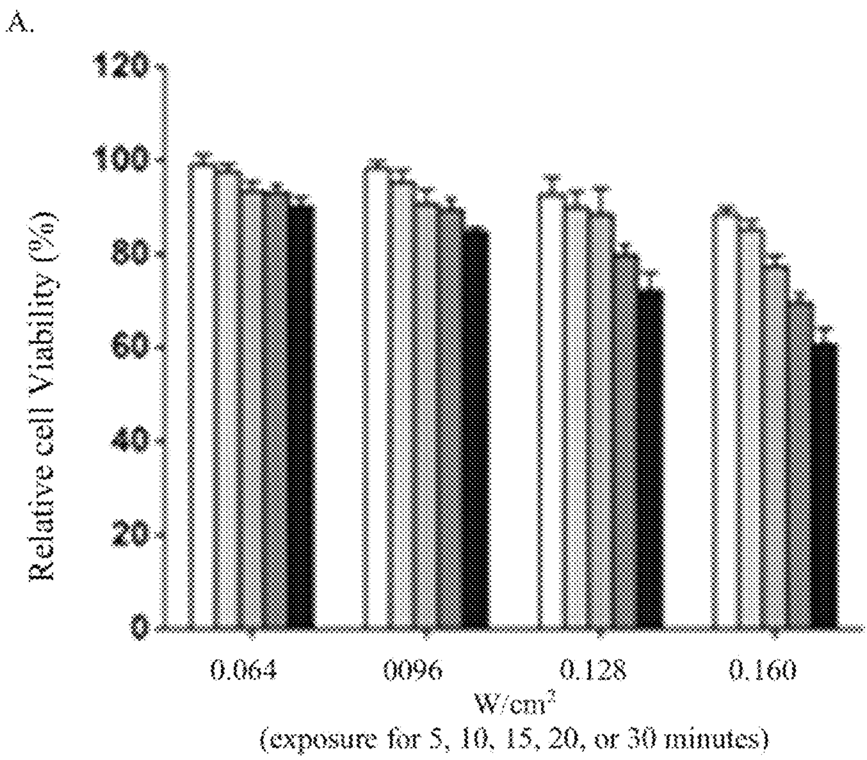
B.
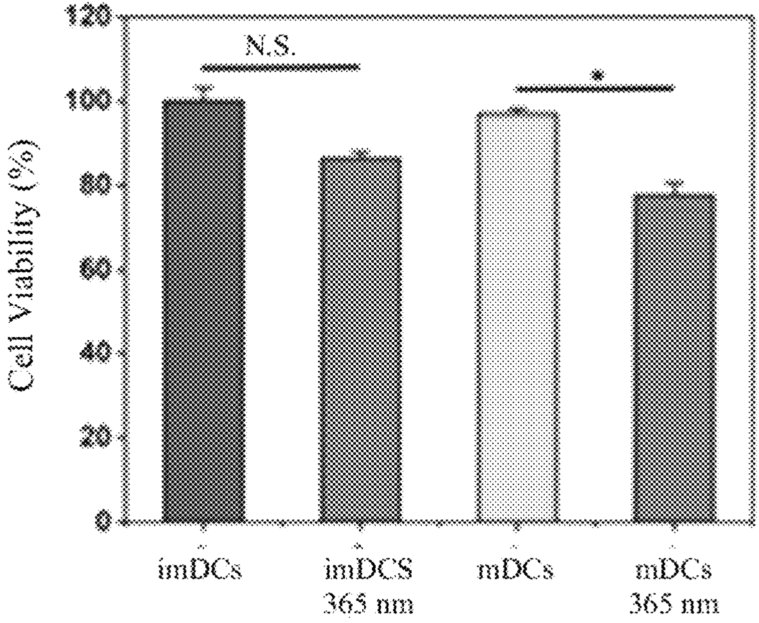
FIG. 6A-B

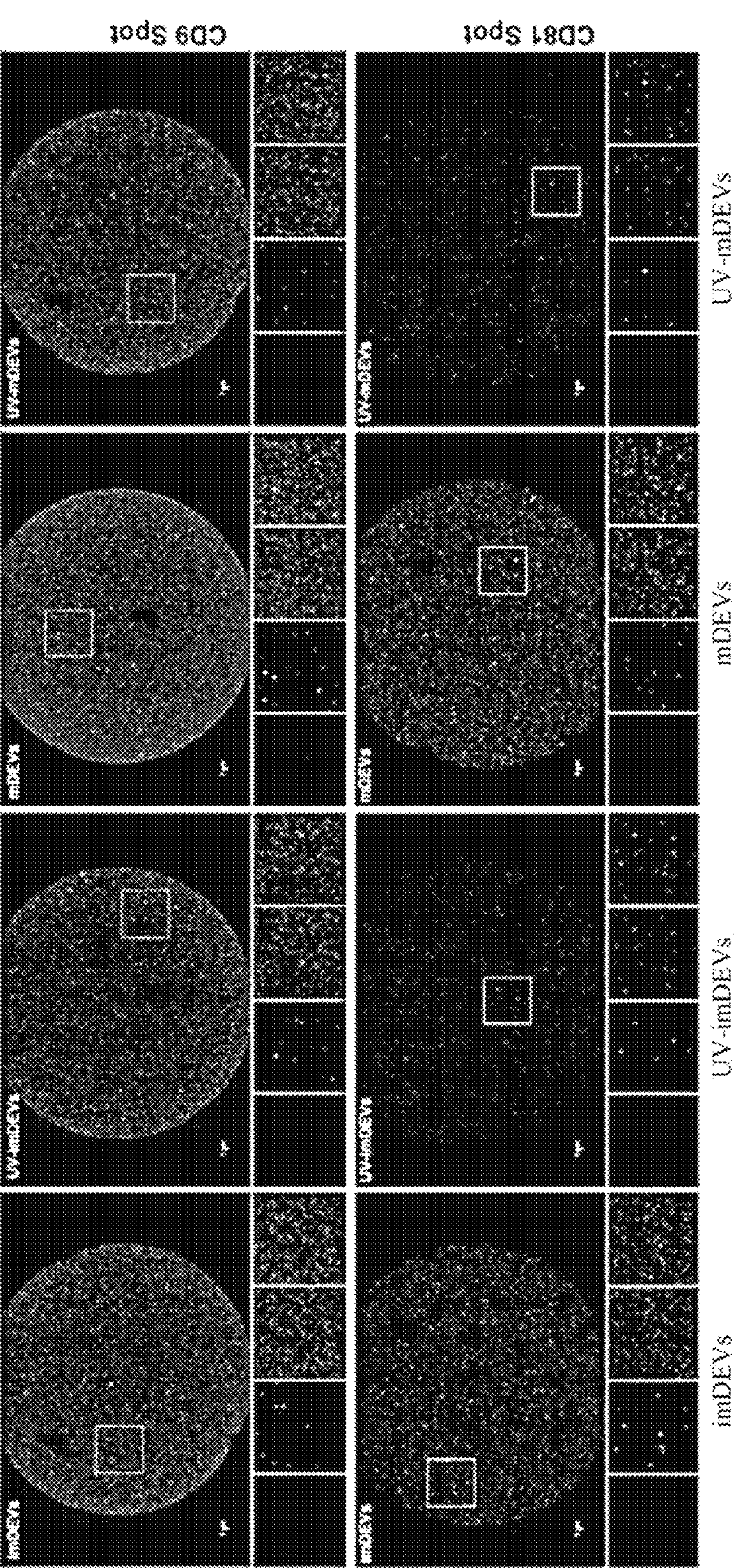
FIG. 7A-B

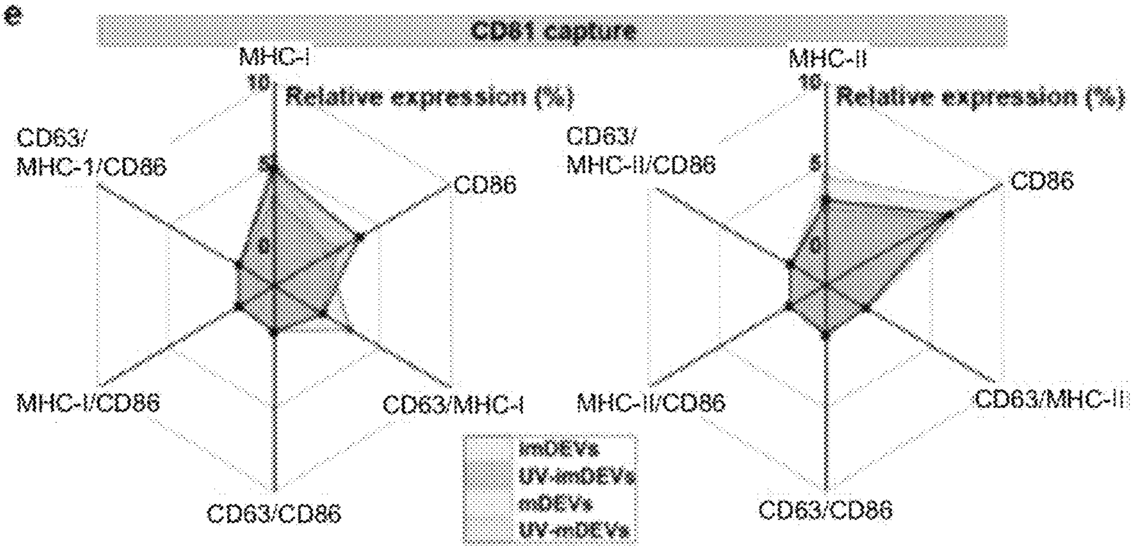
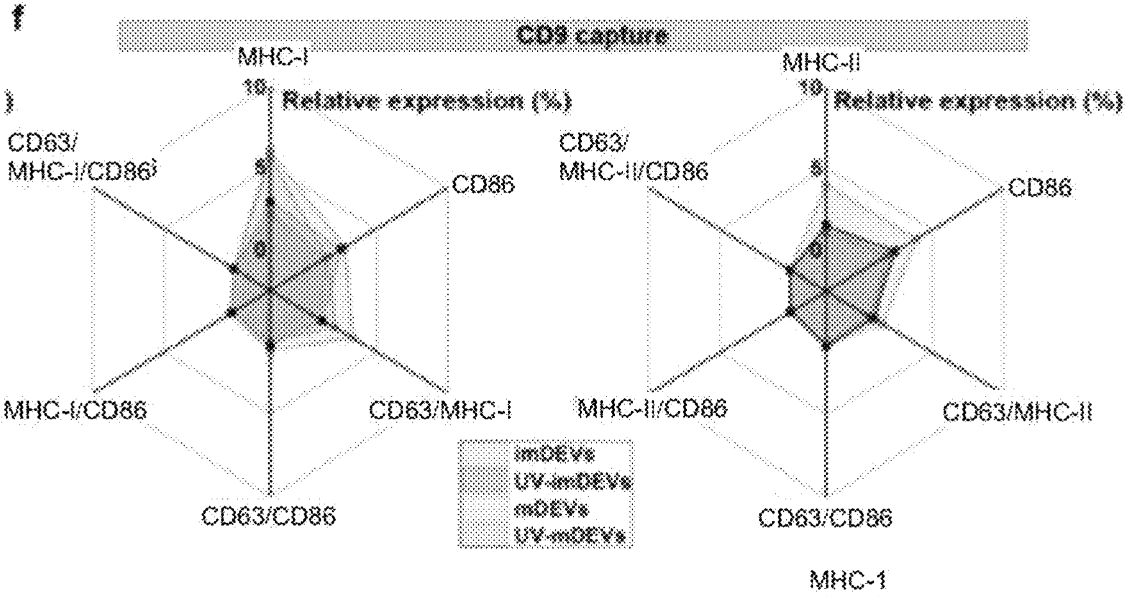
FIG. 7E-F

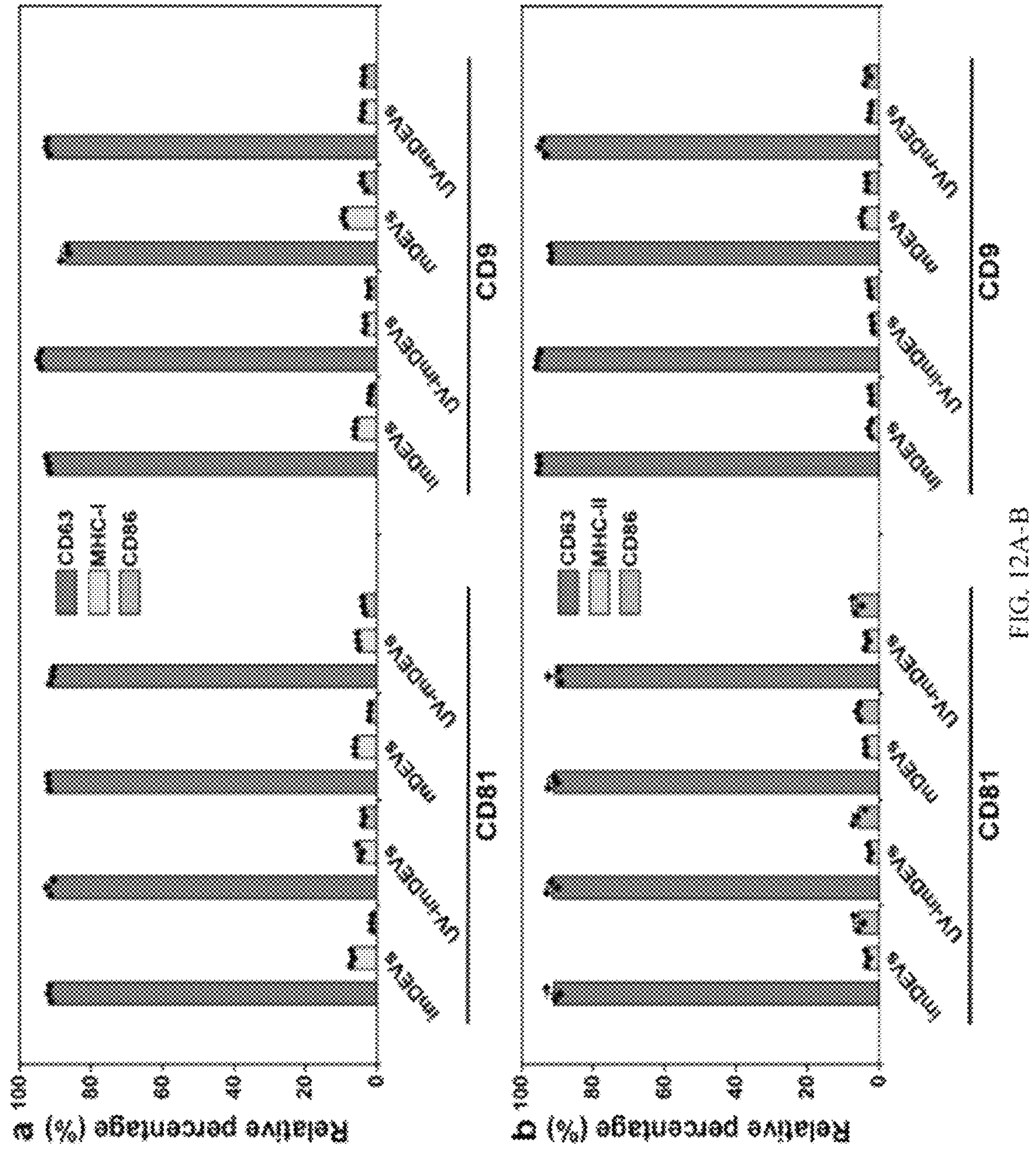
FIG. 12A-B

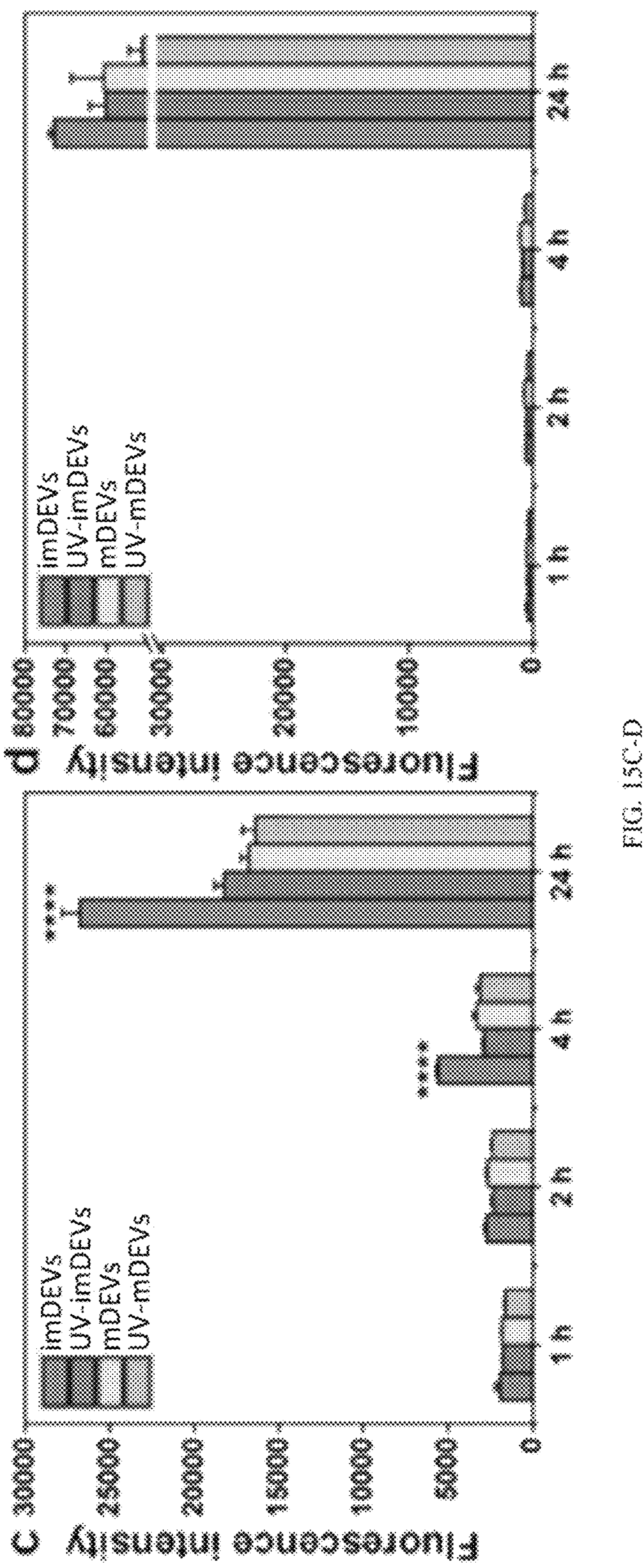
FIG. 15C-D

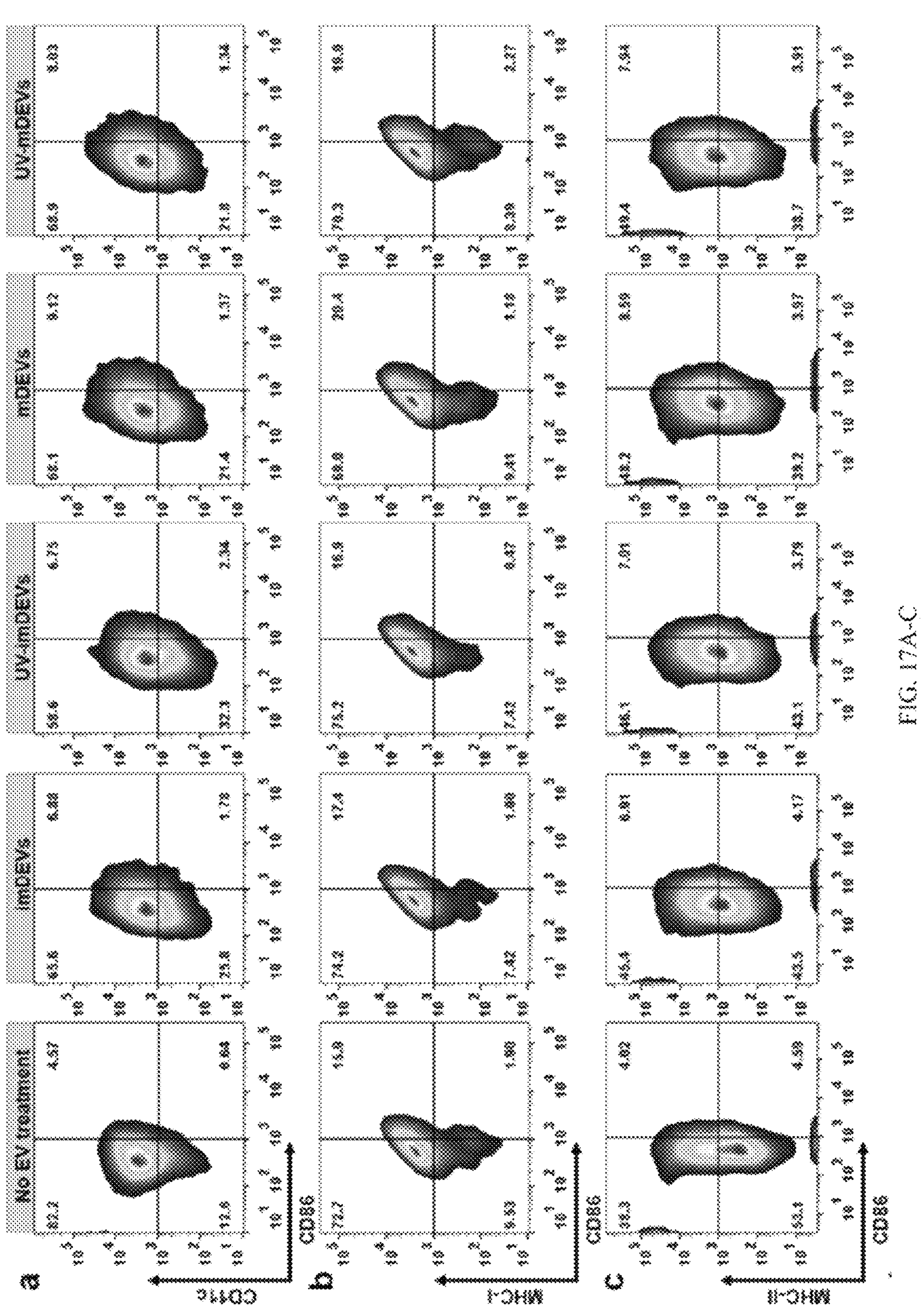
FIG. 17A-C

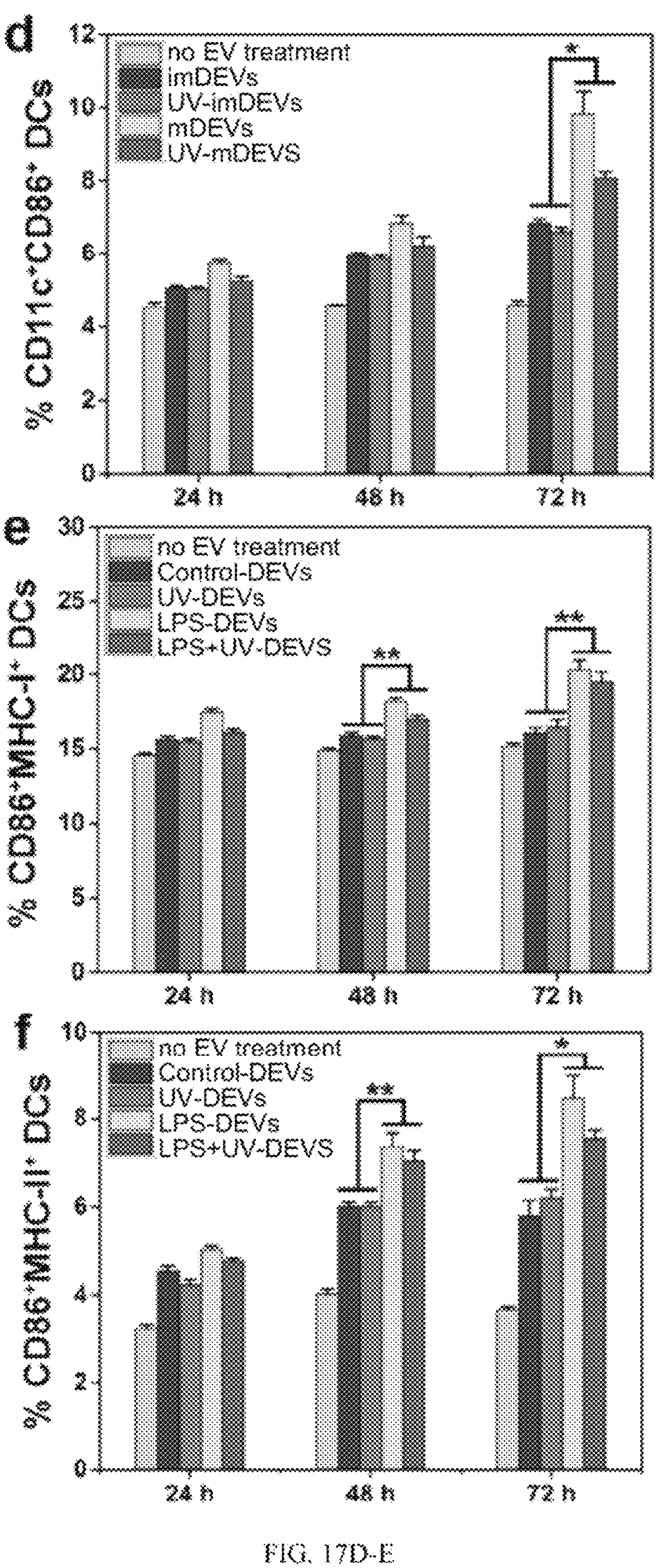
FIG. 17D-E

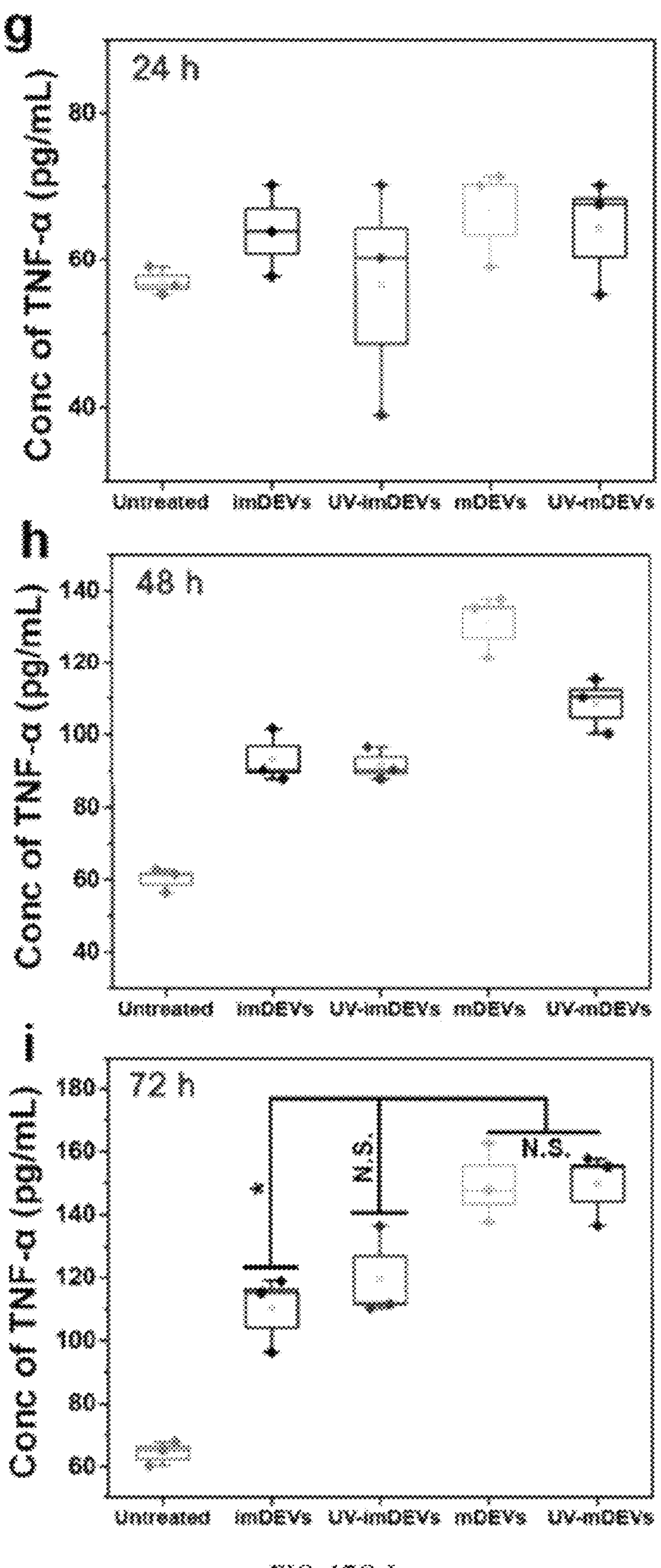
FIG. 17G-I

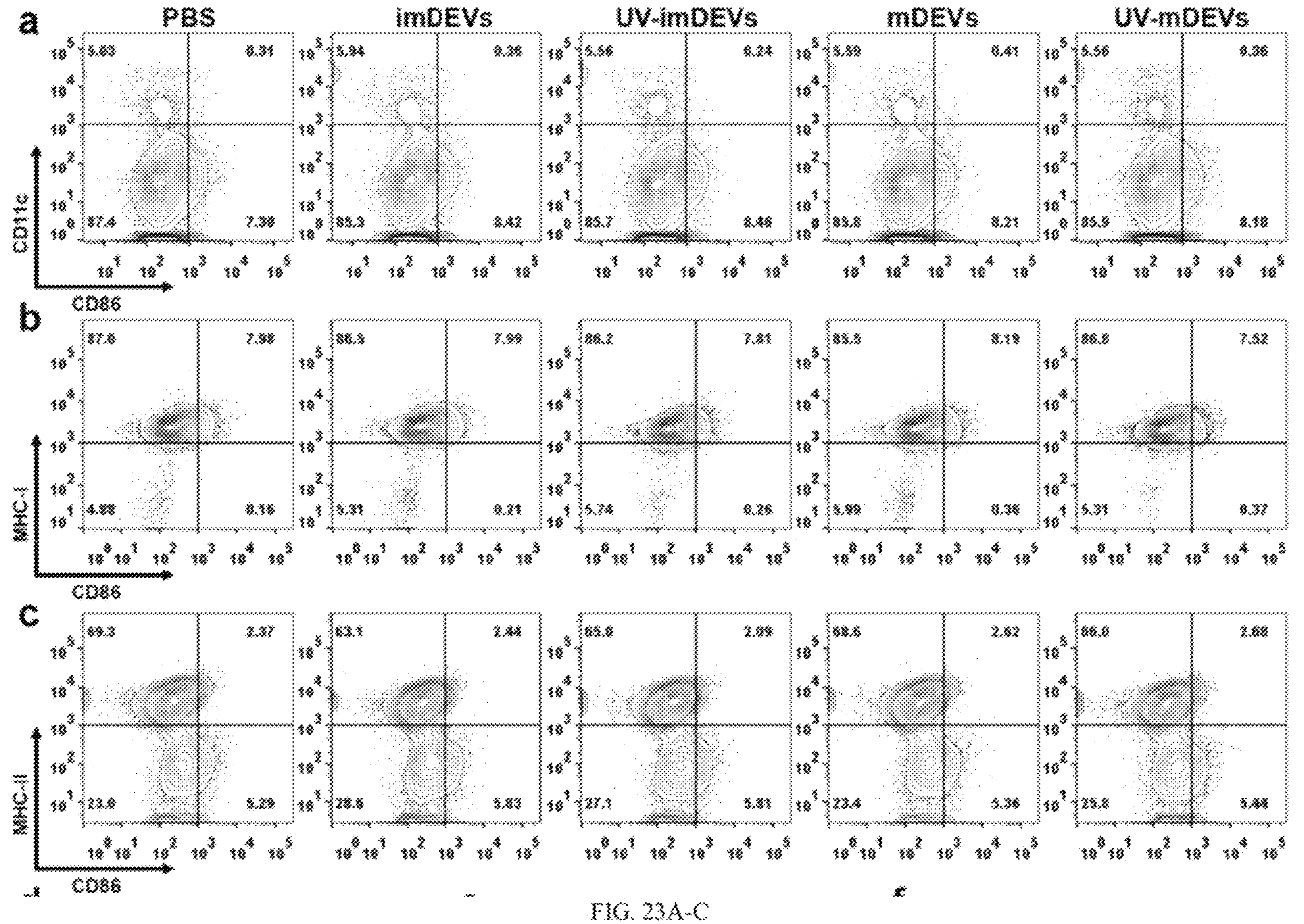
FIG. 23A-C

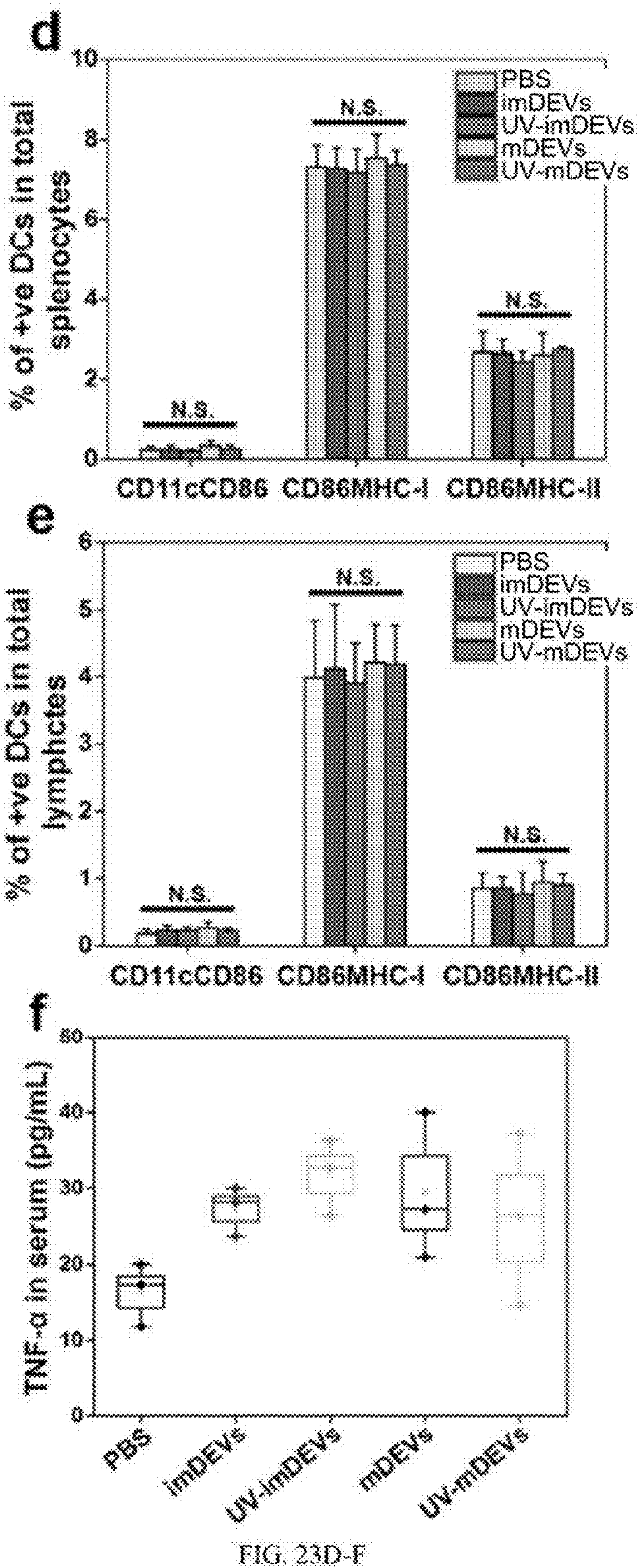
FIG. 23D-F

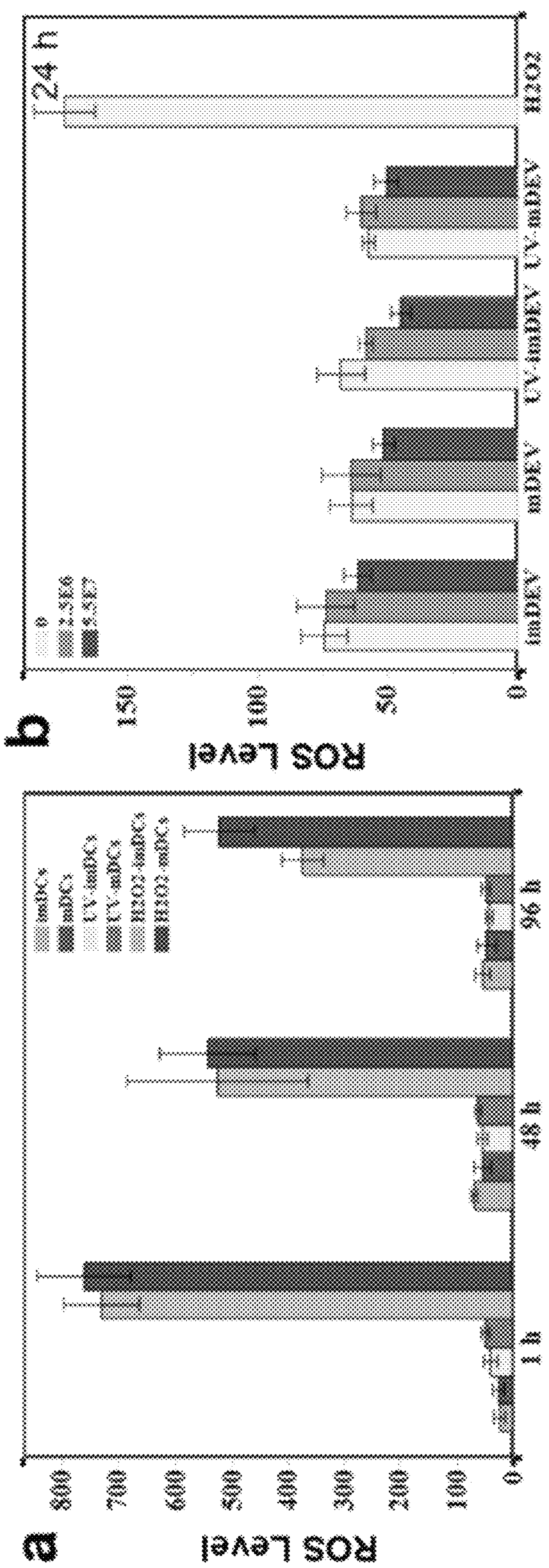
FIG. 27A-B

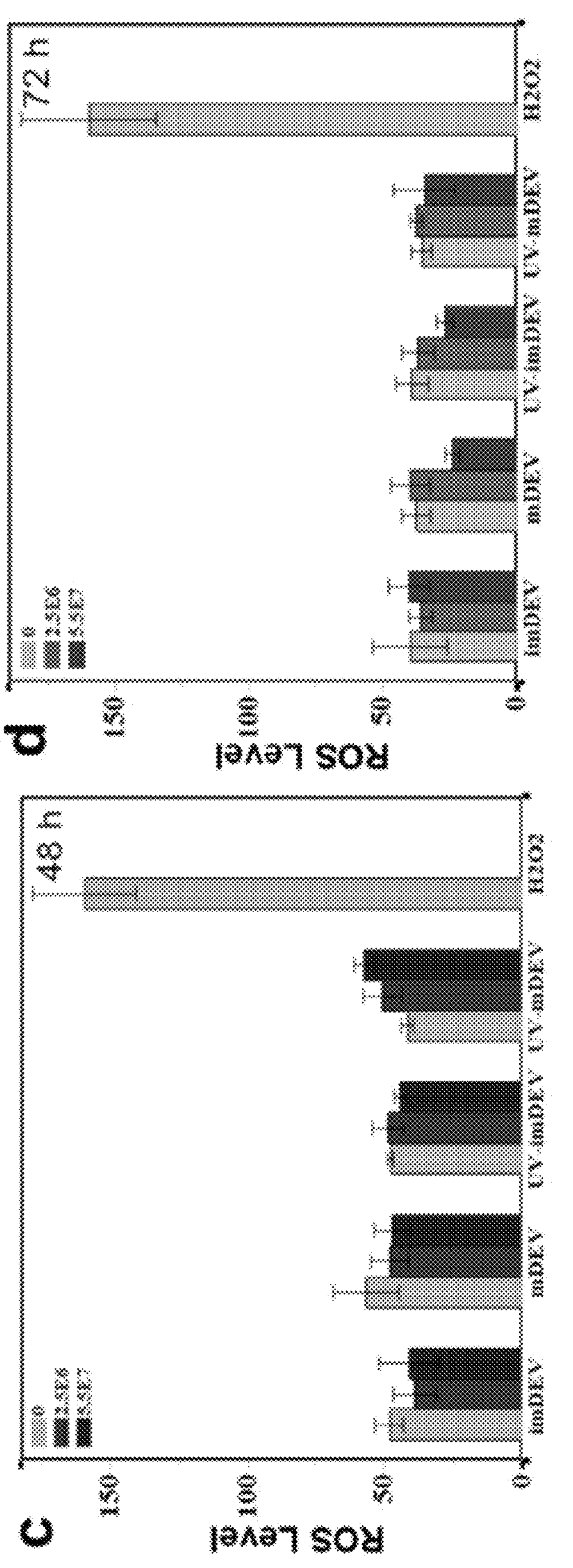
FIG. 27C-D

LIGHT-INDUCED CELLULAR PRODUCTION OF IMMUNE FUNCTIONAL EXTRACELLULAR VESICLES

CROSS-REFERENCE TO RELATED APPLICATIONS

This application is a National Stage Application, filed under 35 U.S.C. § 371, of International Application No. PCT/US2022/036181, filed Jul. 6, 2022, which claims the benefit of U.S. Provisional Application No. 63/219,116, filed Jul. 7, 2021; the contents of which are hereby incorporated by reference in their entirety.

STATEMENT REGARDING FEDERALLY SPONSORED RESEARCH OR DEVELOPMENT

This invention was made with government support under R35 GM133794 awarded by the National Institutes of Health. The government has certain rights in the invention.

INTRODUCTION

Dendritic cell (DC) therapy and DC based vaccine development have been emerging in cancer immunotherapy because DCs are the most potent antigen-presenting cells and are the key initiator of tumor-specific immune responses (Wang Y et al. "Dendritic cell biology and its role in tumor immunotherapy" J Hematol Oncol 13(1):107 (2020); Ogasawara M et al. "Immunotherapy employing dendritic cell vaccination for patients with advanced or relapsed esophageal cancer," Ther Apher Dial 24(5):482-491 (2020); Perez C R et al. "Engineering dendritic cell vaccines to improve cancer immunotherapy," Nat Commun 10(1):5408 (2019)). However, due to the unstable characteristics of DCs in vitro and in vivo, current clinical translation and trial development are suffering from inconsistency and low outcomes (Sadeghzadeh M et al. "Dendritic cell therapy in cancer treatment; the state-of-the-art," Life Sci 254:117580 (2020)). Implementing DC therapy across large populations is costly, difficult to store in long periods, and requires well-defined quality control (Saxena M et al. "Towards superior dendritic-cell vaccines for cancer therapy," Nat Biomed Eng 2(6):341-346 (2018)). Compared to DCs, the secreted extracellular vesicles (EVs) possess superior properties to surmount such drawbacks from cell-based immunotherapies, while maintaining immune-modulation and major stimulating molecules, such as the major histocompatibility complex class I (MHC-I) and class II (MHC-II), intercellular adhesion molecule-1 (ICAM-1), integrins, and costimulatory molecules (e.g., CD80, CD86) (Pitt J M et al. "Dendritic cell-derived exosomes for cancer therapy," J Clin Invest 126(4):1224-32 (2016); Markov O et al. "Immunotherapy Based on Dendritic Cell-Targeted/-Derived Extracellular Vesicles-A Novel Strategy for Enhancement of the Anti-tumor Immune Response," Front Pharmacol 10:1152 (2019)). Currently, DC-EVs based phase I and II clinical trials have been conducted with patients in advanced malignancies, which showed the feasibility and good safety (Pitt J M et al. 2016; Yang X et al. "Clinical use of dendritic cell-derived exosomes for hepatocellular carcinoma immunotherapy: How far we are?" J Hepatol 69(4):984-986 (2018); Tian H et al. "Dendritic cell-derived exosomes for cancer immunotherapy: hope and challenges," Ann Transl Med 5(10):221 (2017); Pitt J M et al. "Dendritic cell-derived exosomes as immunotherapies in the fight against cancer," J Immunol 193(3):1006-11 (2014)).

Extracellular vesicles (EVs)-based therapy and vaccines are emerging. The immunogenicity and the immunomodulatory functions are central roles of EVs (Robbins P D et al. "Regulation of immune responses by extracellular vesicles," Nat Rev Immunol 14(3):195-208 (2014)), which are highly relevant with their parent cell types, as well as the intravesicular and surface molecular compositions. The DC-EVs regulate antigen presentation by carrying membrane and cytoplasmic DC components (Pitt J M et al. 2016; Utsugi-Kobukai S et al. "MHC class I-mediated exogenous antigen presentation by exosomes secreted from immature and mature bone marrow derived dendritic cells," Immunol Lett 89(2-3):125-31 (2003); Gurunathan S et al. "Review of the Isolation, Characterization, Biological Function, and Multifarious Therapeutic Approaches of Exosomes," Cells 8(4) (2019), including MHC-I and MHC-II, ICAM-1, integrins, and T cell co-stimulatory molecules (e.g., CD80, and CD86), which are important for the activation of adaptive immune response (Chaput N et al. "Dendritic cell derived-exosomes: biology and clinical implementations," J Leukoc Biol 80(3):471-8 (2006); Morelli A E et al. "Endocytosis, intracellular sorting, and processing of exosomes by dendritic cells," Blood 104(10):3257-66 (2004); Munich S et al. "Dendritic cell exosomes directly kill tumor cells and activate natural killer cells via TNF superfamily ligands," Oncoimmunology 1(7):1074-1083 (2012). Accumulating evidence suggested that DC-EVs could modulate immune response either directly by exposing MHC-antigen complexes and co-stimulatory molecules to T cells, or indirectly by conveying antigens to surrounding DCs (Fernandez-Delgado I et al. "Immune Regulation by Dendritic Cell Extracellular Vesicles in Cancer Immunotherapy and Vaccines," Cancers (Basel) 12(12) (2020)).

Employment at the scale for population-based dose development is thus far a bottleneck (Jafari D et al. "Improvement, scaling-up, and downstream analysis of exosome production," Crit Rev Biotechnol 1-15 (2020)). Conventional cellular culture and secretion is unable to generate the quantity that meets the clinical dosage needs. Large numbers of cell cultures have to be incubated for days. Unfortunately, current purification of EVs is still in low efficiency. Enhancing the cellular secretion rate for high-efficient production of EVs has been a pressing need (Yamashita T et al. "Possibility of Exosome-Based Therapeutics and Challenges in Production of Exosomes Eligible for Therapeutic Application," Biol Pharm Bull 41(6):835-842 (2018)). A few attempts have been made to increase the production of EVs via genetic manipulation of biogenesis and recycling pathways in their parent cells, such as the genetically engineered overexpression of activator genes or downregulation of ISGylation involved in EV recycling pathways (Ghossoub R et al. "Tetraspanin-6 negatively regulates exosome production, Proc Natl Acad Sci USA 117(11):5913-5922 (2020); Riquelme J A et al. Increased production of functional small extracellular vesicles in senescent endothelial cells," J Cell Mol Med 24(8):4871-4876 (2020); Surman M et al. Extracellular Vesicles as Drug Delivery Systems-Methods of Production and Potential Therapeutic Applications, Curr Pharm Des 25(2):132-154 (2019); Piffoux M et al. "Extracellular vesicles for personalized medicine: The input of physically triggered production, loading and theranostic properties," Adv Drug Deliv Rev 138:247-258 (2019)). Such genetic manipulation could induce cellular production which is different than natural cellular secretion process. Some culture condition engaged methods have been reported to produce more EVs, such as heat shock or radiation treatment, for introducing external stimuli in control of cell proliferation, hypoxia, inflammation, and shear stress (Mitchell J P et al. "Increased exosome production from tumor cell cultures using the Integra CELLine Culture System," J Immunol Methods 335(1-2):98-105 (2008); McNeill B et al. "Collagen biomaterial stimulates the production of extracellular vesicles containing microRNA-21 and enhances the proangiogenic function of CD34 (+) cells," FASEB J 33(3):4166-4177 (2019); Lamichhane T N et al. Production of Extracellular Vesicles Loaded with Therapeutic Cargo, Methods Mol Biol 1831:37-47 (2018)). Recently, Lee research group reported a cellular-nanoporation method for the production of large quantities of EVs containing therapeutic mRNAs and targeting peptides through a focal and transient electrical stimulus, which promotes the release of EVs up to 50-fold increase (Yang Z et al. "Large-scale generation of functional mRNA-encapsulating exosomes via cellular nanoporation," Nat Biomed Eng 4(1):69-83 (2020)). However, to date, how the immunogenicity of produced EVs could be changed or pose influences on downstream applications in therapeutic development and drug delivery has not been explored.

We introduce a simple and straightforward approach for promoting cellular production of dendritic cell derived EVs (DC-EVs) by leveraging a phototherapy based light induction. Compared to other physical stimulations (e.g., heat shock and electric stimuli), light treatment is relatively simple, straightforward, and can be easily adapted into the cell culture incubators or bioreactors on demand at manufacturing scale, without the requirement of specific equipment setup.

SUMMARY

Described are methods of using light wavelengths, intensities, and exposure times, to increase production of extracellular vesicles from cells (e.g., antigen presenting cells, such as dendritic cells). Using the described methods, more than 13-fold enhancement in DC-EV production rate is achieved, while maintaining good integral quality and immune function from the produced EVs. Further, the conditions described triggers enhanced cellular production of EVs regardless of dendritic cell type.

Described are methods for producing extracellular vesicles comprising: exposing at least one cell (such as an antigen presenting cell) to near UV-visible light. The near UV-visible light comprises light having a wavelength of about 315 nm to about 750 nm, about 315 nm to about 500 nm, of about 340 nm to about 390 nm, about 365 nm, about 405 nm, about 488 nm, or about 670 nm. In some embodiments, the near UV to visible light comprises near UV light having a wavelength of about 365 to about 488 nm. In some embodiments, the near UV light has a wavelength of about 365 nm. The at least one cell is exposed to alight lamp having a light intensity of about 1 to about 10 W/cm$^2$ at a distance of about 1 to about 20 cm, a light intensity of 2.4±0.6 W/cm$^2$ at a distance of 10±5 cm, a light intensity of 2.4±0.2 W/cm$^2$ at a distance of 10±1 cm, or a light intensity of about 2.4 W/cm$^2$ at a distance of about 10 cm. The at least one cell can be exposed to near UV-visible light for a duration of about 5 to about 45 minutes, or 30±10 minutes. The intensity of light exposure on the cells can be about 0.05 W/cm$^2$ to about 0.25 W/cm$^2$. In some embodiments, the at least one cell is exposed to near UV-visible light at a light intensity of about 0.05 to about 0.25 W/cm$^2$. In some embodiments, the intensity of light exposure on the cells can be about 0.064 W/cm$^2$ to about 0.16 W/cm$^2$. In some embodiments, the intensity of light exposure on the cells can be about 0.064 W/cm$^2$, about 0.096 W/cm$^2$, about 0.128 W/cm$^2$, or about 0.16 W/cm$^2$. In some embodiments, the intensity of light exposure on the cells is 0.096±0.01 W/cm$^2$. In some embodiments, the intensity of light exposure on the cells is 0.096±0.05 W/cm$^2$. In some embodiments, the intensity of light exposure on the cells is about 0.096±0.05 W/cm$^2$.

The at least one cell can be a eukaryotic cell. The eukaryotic cell can be a mammalian cell. The mammalian cell can be an antigen presenting cell. The antigen presenting cell can be a dendritic cell, macrophage, or B cell. The dendritic cell can be an immature dendritic cell or a mature dendritic cell. The dendritic cell can be a bone marrow derived dendritic cell. The dendritic cell can also be a mammalian dendritic cell, a mouse dendritic cell, a rat dendritic cell, a rabbit dendritic cell, a pig dendritic cell, a sheep dendritic cell, a non-human primate dendritic cell, a human dendritic cell, a horse dendritic cell, a bovine dendritic cell, a dog dendritic cell, or a cat dendritic cell. The at least one mammalian call can also be, but is not limited to, a T cell, a stem cell, or an endothelial cell. The at least one mammalian call can be a primary cell or a cell line cell.

In some embodiments, the methods comprise exposing the at least one cell to 365 nm near UV lamp having a light intensity of about 2.4 W/cm$^2$, at a distance of about 10 cm, and for a duration of about 30 minutes.

In some embodiments, the methods comprise exposing the cells to near UV-visible light at an intensity of about 0.05 W/cm$^2$ to about 0.25 W/cm$^2$ for a duration of 5-35 minutes. In some embodiments, the methods comprise exposing the cells to near UV-visible light at an intensity of about 0.064 W/cm$^2$ to about 0.16 W/cm$^2$ for a duration of 5-30 minutes. In some embodiments, the methods comprise exposing the cells to near UV-visible light at an intensity of about 0.064 W/cm$^2$, about 0.096 W/cm$^2$, about 0.128 W/cm$^2$, or about 0.16 W/cm$^2$ for a duration of 5-30 minutes. In some embodiments, the methods comprise exposing the cells to near UV-visible light at an intensity of about 0.064 W/cm$^2$ for a duration of 5-30 minutes. In some embodiments, the method comprise exposing the cells to 365 nm near UV light at an intensity of about 0.096 W/cm$^2$ for a duration of 5-30 minutes. In some embodiments, the methods comprise exposing the cells to near UV-visible light at an intensity of about 0.128 W/cm$^2$ for a duration of 5-30 minutes. In some embodiments, the methods comprise exposing the cells to near UV-visible light at an intensity of about 0.16 W/cm$^2$ for a duration of 5-30 minutes.

In some embodiments, the methods comprise exposing the cells to 365 nm near UV light at an intensity of about 0.05 W/cm$^2$ to about 0.25 W/cm$^2$ for a duration of 5-35 minutes. In some embodiments, the methods comprise exposing the cells to 365 nm near UV light at an intensity of about 0.064 W/cm$^2$ to about 0.16 W/cm$^2$ for a duration of 5-30 minutes. In some embodiments, the methods comprise exposing the cells to 365 nm near UV light at an intensity of about 0.064 W/cm$^2$, about 0.096 W/cm$^2$, about 0.128 W/cm$^2$, or about 0.16 W/cm$^2$ for a duration of 5-30 minutes. In some embodiments, the methods comprise exposing the cells to 365 nm near UV light at an intensity of about 0.064 W/cm$^2$ for a duration of 5-30 minutes. In some embodiments, the method comprise exposing the cells to 365 nm near UV light at an intensity of about 0.096 W/cm$^2$ for a duration of 5-30 minutes. In some embodiments, the methods comprise exposing the cells to 365 nm near UV light at an intensity of about 0.128 W/cm$^2$ for a duration of 5-30 minutes. In some embodiments, the methods comprise exposing the cells to 365 nm near UV light at an intensity of about 0.16 W/cm$^2$ for a duration of 5-30 minutes.

In some embodiments, the EVs produced from dendritic cells using the described methods are immune functional. The extracellular vesicles can contain one or more of: TNF-α, MHC-I, MHC-II, CD86, CD9, and CD63.

In some embodiments, the methods can be used to provide EVs expressing one or more therapeutic or targeting proteins or polypeptides or one or more therapeutic nucleic acids. In some embodiments, the EVs are derived from a dendritic cell and the therapeutic polypeptide can comprise an antigen, such as tumor antigen or a pathogenic antigen. The cell can be modified to expresses one or more therapeutic or targeting proteins or polypeptides or one or more therapeutic nucleic acids prior to exposure to the near UV-visible light.

The near UV-visible light-induced EVs may be purified or isolated. In some embodiments, isolated DC-derived EVs formed by exposing DC cells to near UV-visible light are described. The isolated DC derived EVs can be loaded with one or more therapeutic molecules. Similar methods can be used to isolate EVs from other cells types, including mammalian cell types. The EVs can also be used to screen potential therapeutic compounds, such as by loading EVs with a library of compounds or creating a library of EVs loaded with compounds to be screened.

DC-derived EVs formed by exposing DC cells to near UV-visible light can be used to deliver or provide a therapeutic treatment to a subject or to provide an immunotherapy. Immunotherapy can comprise stimulating or modulating an immune response in the subject. Stimulating an immune response in a subject can include inducing an immune response against a cancer or vaccinating the subject against a pathogen. Alternatively, EVs formed by exposing other cells to near UV-visible light can be used to deliver or provide a therapeutic treatment to a subject.

BRIEF DESCRIPTION OF THE FIGURES

FIG. 1A-B. (A) Total number of EVs secreted by imDCs and mDCs with or without light treatment (365 nm). (B) Average cellular EV secretion ability with or without light treatment (365 nm).

FIG. 1C-D. (C) Total number of EVs secreted by imDCs and mDCs with or without light treatment (405 nm). (D) Average cellular EV secretion ability with or without light treatment (405 nm).

FIG. 1E-F. (E) Total number of EVs secreted by imDCs and mDCs with or without light treatment (488 nm). (F) Average cellular EV secretion ability with or without light treatment (488 nm). The light condition is at ~0.096 W/cm$^2$ for 30 min. *p<0.0332, p<0.0021, and **p<0.0001.

FIG. 5A-D. Characterization of light-promoted cellular production of EVs. (a) Average cellular secretion rate for EV production from both imDCs and mDCs after light treatment (n=6, each point corresponding to a separate experiment done on a different day). ****p<0.0001. (b) NTA analysis of size distribution of light-promoted EVs, indicating the consistent size range compared to the control group EVs without light treatment (NTA plot is from the average of 5 independent measurements). (c) Zeta potential profiles from light-promoted EVs which is consistent with their control group without light treatment. (d) The TNF-α level carried by light-promoted EVs which is consistent with the control group of native EVs (n=6).

FIG. 5G-H. (g) Quantitative analysis of marker expression levels from immature and mature DCs with or without light treatment (n=3). (c) The TNF-α level in the culture medium secreted by both immature and mature DCs with or without light treatment. All values are presented as means±SD (n=3). ****p<0.0001.

FIG. 6A-B. (a) imDC viability tested 2 days post light treatment under variable light exposure times (5, 10, 15, 20 and 30 min) and intensities (0.064, 0.096, 0.128 and 0.160 W/cm$^2$). (b) The cell viability tested 2 days post light treatment for both imDCs and mDCs at the condition of 0.096 W/cm$^2$ for 30 min, compared to the control group imDC cells without light treatment. *p<0.0332.

FIG. 7A. Evaluation of the immune marker expression from light promoted DEVs using Nano View single-EV microarray. (A, top row) Representative fluorescent microarray imaging of CD63+ (red), MHC-I+ (green), CD86+ (blue) DEVs on CD9 (upper) and CD81 (lower) capture spots. (B, bottom row) Image frames are enlarged views of captured EVs under each fluorescent channel as well as the overlay.

FIG. 7E-F. Radar chart analysis of the relative coexpression levels of multimarkers in various combinations from different EV sample conditions on both CD81 (e) and CD9 (f) capture spots.

FIG. 12. (a) Relative percentage of $CD63^+$, $MHC-I^+$, $CD86^+$ EVs on different CD81 capture spots and CD9 capture spots. (b) Relative percentage of $CD63^+$, $MHC-II^+$, $CD86^+$ EVs on different CD81 capture spots and CD9 capture spots.

FIG. 15C-D. (c) Flow cytometry analysis of imDCs for internalizing light-promoted DEVs compared with native DEVs along time intervals between 1-24 h (n=3). (d) Flow cytometry analysis of IC-21 macrophage cells for internalizing light-promoted DEVs compared with native DEVs along time intervals between 1-24 h (n=3). All values are presented as means±SD. ****$p<0.0001$.

FIG. 17A-C. Assessment of in vitro immunomodulatory function from light-promoted DEVs. Representative flow cytometry analysis of imDCs incubated with DEVs produced from different conditions. The EV dose is 1×109 for 72 h. The imDCs were immunostained with CD11c and CD86 (a), MHC-I and CD86 (b), and MHC-II and CD86 (c).

FIG. 17D-F. Quantitative analysis of immune marker expression level from imDCs after incubation with different DEV samples for 24, 48, and 72 h (n=3), in terms of coexpression of CD11c+CD86+ (d), CD86+MHC-I+ (e), and CD86+MHC-II+ (f).

FIG. 17G-I. Quantitative analysis of cellular cytokine TNF-α secretion by imDCs after incubation with different DEV samples for 24 h (g), 48 h (h), and 72 h (i) (n=3). All values are presented as means±SD. *$p<0.0332$ and **$p<0.0021$.

FIG. 23A-C. In vivo evaluation of immunogenicity of light-promoted DEVs. Representative flow cytometry analysis of CD11c+CD86+ (a), MHC-I+CD86+ (b), and MHC-II+CD86+ (c) in total splenocytes from healthy male mice treated with different DEV samples at 72 h post injection (n=3). PBS injection was set as the negative control.

FIG. 23D-F. Quantitative analysis of the expression level of immune markers from total splenocytes (d) and LNs (e) (n=3). (f) Cytokine level of TNF-α in serum from healthy male mice at 72 h post injection with different DEV samples. PBS injection was set as the negative control (n=3).

FIG. 27A-B. (a) Characterization of cellular oxidative stress levels from light treated DCs monitored 1 h post light treatment to 96 h. The DCs without light treatment serve as the negative control group, and the $H_2O_2$ treated DCs serve as the positive control group. All values are presented as means±SD (n=4). (b) Characterization of cellular oxidative stress levels from imDCs after uptaking light promoted DC EVs at different doses and monitored at 24 h. The EVs derived from DCs without light treatment serve as the negative control group, and the $H_2O_2$ treated DCs serve as the positive control group. All values are presented as means±SD (n=4).

FIG. 27C-D. Characterization of cellular oxidative stress levels from imDCs after uptaking light promoted DC EVs at different doses and monitored at 48 h (c) and 72 h (d). The EVs derived from DCs without light treatment serve as the negative control group, and the $H_2O_2$ treated DCs serve as the positive control group. All values are presented as means±SD (n=4).

DETAILED DESCRIPTION

I. Definitions

Figure 2:
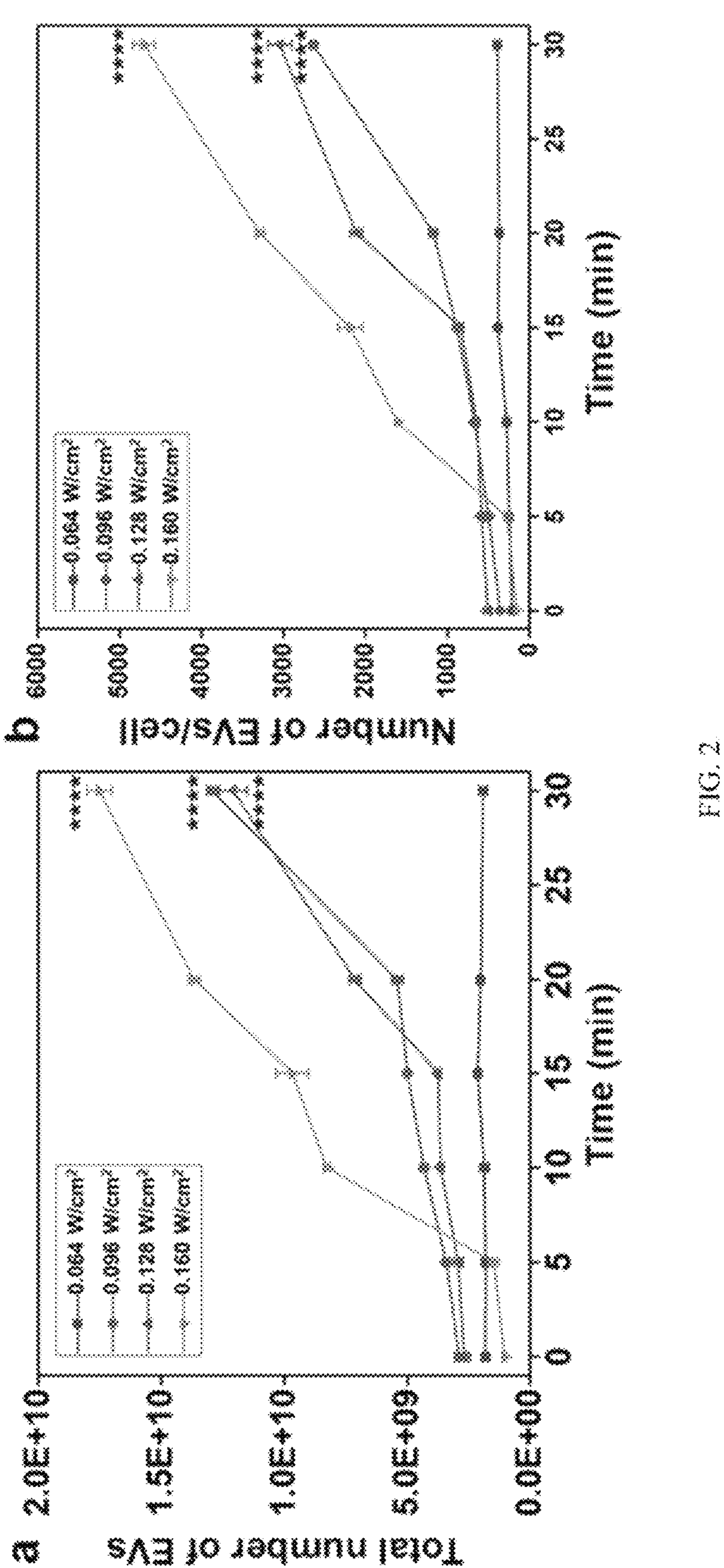
FIG. 2. (a) Total number of EVs secreted by imDCs after 365 nm light exposure at different intensities along time. (b) Average cellular EV secretion rate by each imDC after 365 nm light exposure at different intensities along time. ***p<0.0001 vs 0.064 W/cm$^2$.

Before describing the present teachings in detail, it is to be understood that the disclosure is not limited to specific compositions or process steps, as such may vary. As used in this specification and the appended claims, the singular form "a," "an," and "the" include plural references unless the context clearly dictates otherwise. Thus, for example, reference to "a peptide" includes a plurality of peptides and the like. The conjunction "or" is to be interpreted in the inclusive sense, i.e., as equivalent to "and/or," unless the inclusive sense would be unreasonable in the context.

The use of "comprise," "comprises," "comprising," "contain," "contains," "containing," "include," "includes," and "including" are not intended to be limiting. It is to be understood that both the foregoing general description and detailed description are exemplary and explanatory only and are not restrictive of the teachings. To the extent that any material incorporated by reference is inconsistent with the express content of this disclosure, the express content controls.

The term "about" or "approximately" means within an acceptable error range for the particular value as determined by one of ordinary skill in the art, which will depend in part on how the value is measured or determined, i.e., the limitations of the measurement system. For example, "about" can mean within 1 or more than 1 standard deviation, per the practice in the art. Alternatively, "about" can mean a range of up to 0 to 20%, 0 to 10%, 0 to 5%, or up to 1% of a given value. Where particular values are described in the application and claims, unless otherwise stated the term "about" meaning within an acceptable error range for the particular value should be assumed. In the context of the lengths of nucleotide sequences, the terms "about" or "approximately" are used these lengths encompass the stated length with a variation (error range) of 0 to 10% around the value (X±10%).

All ranges are to be interpreted as encompassing the endpoints in the absence of express exclusions such as "not including the endpoints"; thus, for example, "within 10-15" includes the values 10 and 15. One skilled in the art will understand that the recited ranges include the end values, as whole numbers in between the end values, and where practical, rational numbers within the range (e.g., the range 5-10 includes 5, 6, 7, 8, 9, and 10, and where practical, values such as 6.8, 9.35, etc.). When values are expressed as approximations, by use of the antecedent "about," it will be understood that the particular value forms a further aspect. For example, if the value "about 10" is disclosed, then "10" is also disclosed.

"Subject" refers to an animal, such as a mammal, for example a human. The methods described herein can be useful in both humans and non-human animals. In some embodiments, the subject is a mammal (such as an animal model of disease), and in some embodiments, the subject is human.

An "antigen-Presenting Cell" (APC) is a cell that displays antigen complexed with major histocompatibility complex II (MHCII) on their surfaces. APCs can process external antigens and present them to other immune cells, such as T cells. Macrophages, B cells and dendritic cells (professional antigen presenting cells) are naturally occurring professional APCs. An APC may also express one or more co-stimulatory molecules.

"Dendritic cells" are antigen-presenting cells having the broadest range of antigen presentation and the ability to activate naïve T cells. Their main function is to process antigen material and present it on the cell surface to T cells. DCs present antigen to both helper and cytotoxic T cells.

"Immune therapy" or "Immunotherapy" is the treatment of disease, such as cancer, by activating or suppressing the immune system. Immunotherapies can be designed to elicit or amplify an immune response.

II. Extracellular Vesicles (DC-Derived EVs)

Membranous vesicles are released by a variety of cells into the extracellular microenvironment. Based on the mode of biogenesis, these membranous vesicles can be classified into three broad classes (i), extracellular vesicles (EVs, also termed exosomes) (following the MISEV 2018 guideline, the term EVs is used to cover exosomes as a specific subpopulation of membranous vesicles that includes exosomes, and excludes ectosomes (microvesicles) and apoptotic bodies (Thery C et al. "Minimal information for studies of extracellular vesicles 2018 (MISEV2018): a position statement of the International Society for Extracellular Vesicles and update of the MISEV2014 guidelines," J Extracell Vesicles 7(1):1535750 (2018)), (ii), ectosomes or microvesicles, and (iii) apoptotic bodies. Extracellular vesicles are cell-derived vesicles originating from endosomal compartments produced during the vesicular transport from the endoplasmic reticulum (ER) to the Golgi apparatus. Extracellular vesicles are released extracellularly after the multivesicular bodies are fused with the plasma membrane. Extracellular vesicles are distinct from both ectosomes and apoptotic bodies in size, content, and mechanism of formation. Ectosomes are vesicles of various size (typically 0.1-1 mm in diameter) that bud directly from the plasma membrane and are shed to the extracellular space. Ectosomes have on their surface the phospholipid phosphatidylserine. Apoptotic bodies are formed during the process of apoptosis and engulfed by phagocytes. Dendritic cell (DC)-derived extracellular vesicles (EVs) are EVs produced from dendritic cells. DC-derived EVs are nanoscale membrane vesicles and contain numerous plasma membrane and cytoplasmic DC components. DC-derived EVs can be used to modulate immune responses, either directly by exposing MHC and costimulatory molecules or indirectly transferring associated components to cognate DCs.

DC-derived EVs carry functionally active molecules on their surfaces that take part in modulating immunological response; e.g., antigens, tumor antigens, pathogenic antigens, MHC class I molecules, MHC class II molecules, complexes of MHC class I and/or II with antigens, immune co-stimulatory molecules, adhesion molecules (such as CD80, CD86, and CD40), and cytokines. DC-derived EVs can also contain one or more targeting ligands that target the DC-derived EVs to a tissue or cell type. DC-derived EVs can participate in immune regulation, including induction of anti-tumor T-cell immune responses.

In some embodiments, the DC-derived EVs carry one or more molecules required to activate anti-tumor T cell-mediated immune response. These molecules can include one or more of: tumor antigens, MHC class I molecules, MHC class II molecules, immune co-stimulatory molecules, adhesion molecules, targeting ligands, and cytokines.

In some embodiments, the DC-derived EVs carry one or more molecules required to activate a T cell-mediated immune response. These molecules can include one or more of: pathogenic antigens, MHC class I molecules, MHC class II molecules, immune co-stimulatory molecules, adhesion molecules, targeting ligands, and cytokines.

III. Near UV-Visible Light-Induced Production of EVs

Described herein are methods of producing extracellular vesicles from cells. The cells can be, but are not limited to, as antigen presenting cells. Antigen presenting cells can be, but are not limited to, dendritic cells. The methods comprises exposing the cells to near UV-visible light. In some embodiments, the methods comprises exposing the cells to near UV light. Exposing the cells to near UV-visible light induces production of EVs by the cells. Exposing the DCs to near UV-visible light induces production of immune-competent EVs by the dendritic cells. The methods can increase production of DC-derived EVs by about 5-15 fold or more compared to the same dendritic cells in the absence of the near UV-visible light exposure. The near UV-visible wavelengths used do not substantially impair cell growth.

The antigen presenting cells can be, but are not limited to, dendritic cells, immature DCs, mature DCs, bone marrow derive DCs, JAWS II cells, mature JAWS II cells (matured with exposure to bacterial (e.g., *E. coli*) lipopolysaccharide (LPS)), macrophages (e.g., IC-21 cells), and B lymphocytes (B cells). The DCs can be, but are not limited to, mammalian DCs, mouse DCs, rat DCs, rabbit DCs, pig DCs, sheep DCs, non-human primate DCs, human DCs, horse DCs, bovine DCs, dog DCs, or cat DCs.

In some embodiments, the described near UV-visible light exposure conditions can be used to induce formation of EVs from other cells. The other cells include, but are not limited to, mammalian cells, immune cells (e.g., T cells), stem cells, and endothelial cells (e.g., HUVEC cells).

In some embodiments, the cell can be a primary cell or a cell line cell.

In some embodiments, the cells (e.g., dendritic cells) are exposed to near UV-visible light having a wavelength of about 315 nm to about 750 nm. In some embodiments, the cells are exposed to near UV-visible light having a wavelength of about 315 nm to about 670 nm. In some embodiments, the cells are exposed to near UV-visible light having a wavelength of about 365 nm to about 670 nm. In some embodiments, the cells are exposed to near UV-visible light having a wavelength of about 315 nm to about 500 nm. In some embodiments, the cells are exposed to near UV light having a wavelength of about 315 nm to about 490 nm, about 365 nm to about 488 nm, about 315 nm to about 405 nm, about 340 nm to about 390 nm, about 355 nm to about 375 nm, about 360 nm to about 370 nm, about 365 nm, about 405 nm, or about 488 nm. In some embodiments, the cells are exposed to visible light having a wavelength of about 670 nm. In some embodiments, the cells are exposed to near UV light having a wavelength of about 365 nm. Near UV-visible light of a wavelength that does not readily induce apoptosis is used.

In some embodiments, the cells (e.g., dendritic cells) are exposed to near UV-visible light at the indicated wavelengths using a lamp that produces light at an intensity of about 0.1 mW to about 10 W/cm$^2$, about 1 to about 5 W/cm$^2$, about 1.6 to about 4 W/cm$^2$, about 2 to about 3 W/cm$^2$, about 1.6 W/cm$^2$, about 2.4 W/cm$^2$, about 3.2 W/cm$^2$, or about 4.0 W/cm$^2$. In some embodiments, the cells are exposed to near UV-visible light at the indicated wavelengths using a lamp that produces light at an intensity of 2.4±0.6 W/cm$^2$, 2.4±0.5 W/cm$^2$, 2.4±0.4 W/cm$^2$, 2.4±0.3 W/cm$^2$, 2.4±0.2 W/cm$^2$, or 2.4±0.1 W/cm$^2$.

In some embodiments, the cells (e.g., dendritic cells) are exposed to near UV light at the indicated wavelengths using a lamp that produces light at an intensity of about 0.1 mW to about 10 W/cm$^2$, about 1 to about 5 W/cm$^2$, about 1.6 to about 4 W/cm$^2$, about 2 to about 3 W/cm$^2$, about 1.6 W/cm$^2$, about 2.4 W/cm$^2$, about 3.2 W/cm$^2$, or about 4.0 W/cm$^2$. In some embodiments, the cells are exposed to near UV light at the indicated wavelengths using a lamp that produces light at an intensity of 2.4±0.6 W/cm$^2$, 2.4±0.5 W/cm$^2$, 2.4±0.4 W/cm$^2$, 2.4±0.3 W/cm$^2$, 2.4±0.2 W/cm$^2$, or 2.4±0.1 W/cm$^2$.

In some embodiments, the cells (e.g., dendritic cells) are exposed to near UV-visible light at the indicated wavelengths and light intensity for an exposure duration of about 1 to about 45 minutes, about 5 to about 40, about 1, about 2, about 3, about 4, about 5, about 6, about 7, about 8, about 9, about 10, about 11, about 12, about 13, about 14, about 15, about 16, about 17, about 18, about 19, about 20, about 21, about 22, about 23, about 24, about 25, about 26, about 27, about 28, about 29, about 30, about 31, about 32, about 33, about 34, or about 35 minutes. In some embodiments, the cells are exposed to near UV-visible light and the indicated wavelengths at a light intensity for an exposure duration of 30±10, 30±9, 30±8, 30±7, 30±6, 30±5, 30±4, 30±3, 30±2, or 30±1 minutes.

In some embodiments, the cells (e.g., dendritic cells) are exposed to near UV light at the indicated wavelengths and light intensity for an exposure duration of about 1 to about 45 minutes, about 5 to about 40, about 1, about 2, about 3, about 4, about 5, about 6, about 7, about 8, about 9, about 10, about 11, about 12, about 13, about 14, about 15, about 16, about 17, about 18, about 19, about 20, about 21, about 22, about 23, about 24, about 25, about 26, about 27, about 28, about 29, about 30, about 31, about 32, about 33, about 34, or about 35 minutes. In some embodiments, the cells are exposed to near UV light and the indicated wavelengths at a light intensity for an exposure duration of 30±10, 30±9, 30±8, 30±7, 30±6, 30±5, 30±4, 30±3, 30±2, or 30±1 minutes.

In some embodiments, the cells (e.g., dendritic cells) are exposed to near UV-visible light at the indicated wavelengths, light intensity, and exposure duration, at a distance of about 1 to about 20 cm, about 2 to about 18 cm, about 5 to about 15 cm, about 8 to about 12 cm, about 9 to about 11 cm, about 5 cm, about 6 cm, about 7 cm, about 8 cm, about 9 cm, about 10 cm, about 11 cm, about 12 cm, about 13 cm, about 15 cm, or about 15 cm. In some embodiments, the cells are exposed to near UV-visible light at the indicated wavelengths, light intensity, and exposure duration, at a distance of 10±5 cm, 10±4 cm, 10±3 cm, 10±2 cm, or 10±1 cm. In some embodiments, the cells are exposed to near UV-visible light at the indicated wavelengths, light intensity, and exposure duration, at a distance of about 10 cm.

In some embodiments, the cells (e.g., dendritic cells) are exposed to near UV light at the indicated wavelengths, light intensity, and exposure duration, at a distance of about 1 to about 20 cm, about 2 to about 18 cm, about 5 to about 15 cm, about 8 to about 12 cm, about 9 to about 11 cm, about 5 cm, about 6 cm, about 7 cm, about 8 cm, about 9 cm, about 10 cm, about 11 cm, about 12 cm, about 13 cm, about 15 cm, or about 15 cm. In some embodiments, the cells are exposed to near UV light at the indicated wavelengths, light intensity, and exposure duration, at a distance of 10±5 cm, 10±4 cm, 10±3 cm, 10±2 cm, or 10±1 cm. In some embodiments, the cells are exposed to near UV light at the indicated wavelengths, light intensity, and exposure duration, at a distance of about 10 cm.

In some embodiments, the cells (e.g., dendritic cells) are exposed to near UV light at a wavelength of about 365 nm at an intensity of about 2.4 W/cm$^2$ and a distance of about 10 cm for a duration of about 30 minutes.

In some embodiments, the cells receive an exposure intensity of near UV-visible light of about 0.05 W/cm$^2$ to about 0.25 W/cm$^2$. In some embodiments, the cells receive an exposure intensity of near UV-visible light of about 0.064 W/cm$^2$, about 0.096 W/cm$^2$, about 0.128 W/cm$^2$, or about 0.16 W/cm$^2$. In some embodiments, the cells receive an exposure intensity of near UV-visible light of about 0.085, about 0.09, about 0.095, about 0.096, about 0.1, about 0.105, or about 0.11 W/cm$^2$. In some embodiments, the cells receive an exposure intensity of near UV-visible light of about 0.096 W/cm$^2$ for about 30 minutes.

In some embodiments, the cells receive an exposure intensity of near UV light of about 0.05 W/cm$^2$ to about 0.25 W/cm$^2$. In some embodiments, the cells receive an exposure intensity of near UV light of about 0.064 W/cm$^2$, about 0.096 W/cm$^2$, about 0.128 W/cm$^2$, or about 0.16 W/cm$^2$. In some embodiments, the cells receive an exposure intensity of near UV light of about 0.085, about 0.09, about 0.095, about 0.096, about 0.1, about 0.105, or about 0.11 W/cm$^2$. In some embodiments, the cells receive an exposure intensity of near UV light of about 0.096 W/cm$^2$ for about 30 minutes.

In some embodiments, the cells receive an exposure intensity of 365 nm UV light of about 0.05 W/cm$^2$ to about 0.25 W/cm$^2$. In some embodiments, the cells receive an exposure intensity of 365 nm UV light of about 0.064 W/cm$^2$, about 0.096 W/cm$^2$, about 0.128 W/cm$^2$, or about 0.16 W/cm$^2$. In some embodiments, the cells receive an exposure intensity of 365 nm UV light of about 0.085, about 0.09, about 0.095, about 0.096, about 0.1, about 0.105, or about 0.11 W/cm$^2$. In some embodiments, the cells receive an exposure intensity of 365 nm UV light of about 0.096 W/cm$^2$ for about 30 minutes.

DC-derived EVs produced using the described methods exhibit size, zeta potential, morphology, immune surface markers and cytokines, biocompatibility, cellular uptake behavior, immune-modulation ability on eliciting cellular responses in vitro that are consistent with EVs from DCs produced in the absence of near UV-visible treatment (native DC-EVs). Further, the DC-derived EVs produced using the described methods exhibited biodistribution, immunogenicity, and administration safety properties in model mice that indicate that they are suitable of use in treatment of subjects, including human subjects. In vivo animal study also demonstrated near UV-visible light-promoted DC-derived EVs are as well tolerated as native DC-EVs, and exhibited no safety concerns. DC-derived EVs produced using the described methods are suitable for use in therapeutic platforms in scalable production. EVs produced from other cell types using the described methods are expected to exhibit sizes, zeta potentials, morphologies, surface markers, and biocompatibilities that are consistent with EVs from the same cell types produced (albeit at a lower rate) in the absence of near UV-visible light treatment (native EVs).

Analysis of major immune markers from produced EVs, from either immature DCs or mature DCs—including MHC-I, MHC-II, and CD86—did not show significant changes between EVs produced according to the described methods and a control group without light treatment. The immunomodulation function, immunogenicity, and biocompatibility of near UV-visible light-promoted EVs from both their parent immature (imDCs) or mature DCs (mDCs) are also comparable to naturally produced EVs both in vitro and in vivo. The in vivo animal study on biodistribution of near UV-visible light-promoted DC-derived EVs showed very high similarity (>98%) with naturally derived DC EVs. The immune profiling of single-cell suspended immune cells from mice spleens and lymph nodes exhibited no significant difference between near UV-visible light-promoted DC-derived EVs and naturally derived DC-EVs for the markers tested. The immunity elicitation by near UV-visible light-promoted DC-derived EVs is also comparable naturally produced DC EVs. However, the near-UC treatment of DCs resulted in signification higher production of EVs. Thus, near UV-visible light treatment of dendritic cells provides significantly increase yield of EVs without compromising function.

The near UV-visible light-promoted DC-derived EVs are immune functional and able to modulate immune function. Like DC EVs obtained in the absence of near UC exposure, the DC-derived EVs produced according to the described methods contain one or more immune-modulation functional markers selected from the group consisting of: TNF-α, MHC-I, MHC-II, CD86, CD9, and CD63.

In some embodiments, the DC-derived EVs produced according to the described methods can be internalized by immune and non-immune cells. The immune and non-immune cells can be in a subject, such as a human.

In some embodiments, the DC-derived EVs produced according to the described methods are able to modulate immune function. In some embodiments, the DC-derived EVs produced according to the described methods are able to modulate immune function in a subject, such as a human.

In some embodiments, the DC-derived EVs produced according to the described methods are able to induce expression of immune functional markers in dendritic cells. The dendritic cells can be in a subject, such as a human.

In some embodiments, the DC-derived EVs produced according to the described methods are able to stimulate DC maturation. In some embodiments, the DC-derived EVs produced according to the described methods are able to stimulate DC maturation in a subject.

In some embodiments, the DC-derived EVs produced according to the described methods are themselves non-immunogenic in that they do not induce an immune response against themselves.

In some embodiments, the EVs produced according to the described methods can be internalized by another cell. The cell can be in a subject, such as a human.

In some embodiments, the EVs produced according to the described methods are able to modulate on or more functions of cells following contacting the cells with the EVs. The cells can be in a subject, such as a human In some embodiments, the EVs produced according to the described methods are able to stimulate a response in a cell or tissue. The cell or tissue can be in a subject, such as a human.

In some embodiments, the EVs produced according to the described methods are themselves non-immunogenic in that they do not induce an immune response against themselves.

In some embodiments, the EVs produced according to the described methods can be used to screen potential therapeutic compounds.

IV. Formulation

In some embodiments, the DC-derived EVs produced by the methods described herein can be isolated using methods known in the art for isolating or purifying EVs. Such methods include, but are not limited to, sequential centrifugation (including ultracentrifugation), centrifugation using a sucrose density gradient or sucrose cushion, ultrafiltration, ExoQuick (System biosciences), Total Exosome Isolation Kit (Invitrogen), immunoaffinity capture, microfluidics-based isolation, and combinations thereof.

In some embodiments, the DC-derived EVs produced by the methods described herein can be formulated for long term storage.

In some embodiments, the DC-derived EVs produced by the methods described herein can be provided in a kit. Kits will generally comprise the DC-derived EVs in a suitable container or receptacle in a pharmaceutically acceptable formulation.

DC-derived EVs produced using the described methods can be loaded with one or more cargo molecules. The cargo molecule can be, for example, a therapeutic molecule or targeting molecule. In some embodiments, the DC-derived EVs contain one or more nucleic acids such as, but not limited to, antisense oligonucleotides, siRNAs, miRNAs, and CRISPR RNAs. In some embodiments, the DC-derived EVs contain one or more polypeptides. The polypeptides can be, but are not limited to, antigens, tumor antigens, pathogenic antigens, viral antigens, bacterial antigens, fungal antigens, and parasitic antigens, cytokines, targeting ligands, and immune co-stimulators. In some embodiments, the DC-derived EVs contain one or more drugs. The DC-derived EVs can be modified to contain or deliver particular molecules by loading them after shedding by the dendritic cells or by loading the dendritic cells prior to inducing EV formation using near UV-visible light. Targeting molecules include, but are not limited to: MHC molecules, tetraspanin family proteins, integrin family proteins, cell receptors and cell receptor ligands. A cargo molecule is loaded onto a DC-derived EV if it is present in the interior of the EV, in the membrane of the EV (e.g., integral membrane protein), or associated with the surface of the EV.

In some embodiments, DC-derived EVs are indirectly loaded with therapeutic or targeting molecules by loading the DCs prior to EV induction. In some embodiments, the DCs are transfected with a nucleic acid that expresses a therapeutic nucleic acid or a therapeutic polypeptide. The therapeutic nucleic acid or a therapeutic polypeptide is then incorporated into the EVs produced from the DCs. DCs can also be loaded with therapeutic polypeptides by relying on the intrinsic ability of DCs to capture proteins and peptides from surrounding fluids.

In some embodiments, DC-derived EVs are directly loaded with therapeutic molecules following near-UV-visible light-induced production. The EVs can be loaded prior to or after purification or isolation.

V. Methods of Using DC-derived EVs

In some embodiments, the DC-derived EVs produced according to the described methods are used to modulate immune function in a subject.

In some embodiments, the DC-derived EVs produced according to the described methods are used to induce expression of immune functional markers in dendritic cells. The dendritic cells can be in a subject, such as a human.

In some embodiments, the DC-derived EVs produced according to the described methods are used to stimulate DC maturation. In some embodiments, the DC-derived EVs produced according to the described methods are used to stimulate DC maturation in a subject, such as a human.

In addition to providing EVs with immunoregulatory function, the described methods can also be used to produce EVs that are loaded or can be loaded with drugs, specific tissue targeting molecules, or immunotherapeutic agents. The methods can also be used to produce EVs suitable for EV-based therapies and vaccines.

In some embodiments, the DC-derived EVs produced according to the described methods are loaded with a cargo molecule and optionally a targeting molecule and used to deliver the cargo molecule to a cell or tissue. The cell or tissue can be in a subject. In some embodiments, the cargo is a therapeutic molecule such as a drug.

In some embodiments, the DC-derived EVs produced according to the described methods are loaded with an antigen and used in a vaccine. In some embodiments, the DC-derived EVs are used in cell-free vaccines. The DC-derived EVs can contain one or more antigens. The antigen can be complexed with an MHC class I and or class II molecule. Antigens include, but are not limited to: tumor antigens and pathogenic antigens. Pathogenic antigens include, but are not limited to: viral antigens, bacterial antigens, fungal antigens, and parasitic antigens.

In some embodiments, the DC-derived EVs produced by the methods described herein can be formulated for use in anti-tumor vaccines.

In some embodiments, the DC-derived EVs produced according to the described methods are used in immunotherapy. In some embodiments, the DC-derived EVs produced by the methods described herein can be used to modulate an immune reaction or immunoregulation. In some embodiments, the DC-derived EVs produced by the methods described herein can be used to transfer tumor antigenic peptides and immunostimulatory molecules to DCs.

Is some embodiments, the DC-derived EVs produced according to the described methods can be engineered or modified to contain specific molecules on EV surfaces. The specific molecules include, but are not limited to, MHC molecules, tetraspanins, integrins, or targeting molecules.

The DC-derived EVs can be engineered or modified to target specific recipient cells and mediate cargo transfer and cellular responses.

In some embodiments, methods of providing therapeutic extracellular vesicles to a subject are provided comprising: exposing at least one cell to near UV-visible light to induce production of extracellular vesicles; isolating the extracellular vesicles; optionally loading the extracellular vesicles with one or more therapeutic molecules, and administering the extracellular vesicles to the subject.

In some embodiments, methods of immunotherapy comprises are provided comprising: exposing at least one cell containing or expressing a therapeutic polypeptide or nucleic acid to near UV-visible light to induce production of extracellular vesicles; isolating the extracellular vesicles; optionally loading the extracellular vesicles with one or more therapeutic molecules, and administering the extracellular vesicles to the subject.

EXAMPLES

Example 1

A. Cell Culture and Preparation.

Antigen presenting JAWS II cells were cultured in alpha-MEM (minimum essential medium $\alpha$) medium (Gibco, USA) containing 20% fetal bovine serum (FBS, Gibco, USA), 1% penicillin-streptomycin (Corning, Arizona, USA) and 5 ng/ml recombinant mouse granulocyte macrophage colony-stimulating factor (GM-CSF) (R&D Systems, USA). IC-21 macrophages were cultured in RPMI-1640 medium (ATCC, USA) containing 10% FBS and 1% penicillin-streptomycin. Human umbilical vein endothelial cells (HUVEC) were cultured in F-12K medium (gibco, USA) containing 10% FBS, 1% penicillin-streptomycin, 0.1 mg/mL heparin (Sigma, USA) and 30 μg/mL endothelial cell growth supplement (ECGS, Fisher Scientific, USA). Subculture were maintained in humidified incubator with 5% $CO_2$ supply at 37° C. and all experiments were performed during the logarithmic phase of cell growth.

B. Culture and Maturation of Mouse Bone Marrow DC Cell Line JAWS II.

Immature JAWS II cells were passaged into T-25 (25 $cm^2$) flask and allowed to grow 2 days (approximately 40% confluency). Afterwards, lipopolysaccharide (LPS) (LPS from *E. coli* O111:B4 strain) pre-dissolved in endotoxin-free water (1 mg/mL) was introduced into the culture medium at a final concentration of 100 ng/mL for another 2 days culture to induce JAWS II cells maturation. For immature DCs, cells were not exposed to LPS. For near UV condition screening, immature JAWS II cells were passaged into T-25 (25 $cm^2$) flask and allowed to grow 4 days (approximately 80% confluency).

C. Induction of EV Production.

Cell cultures were exposed under near-UV LED light (OmniCure AC450/P-365UV), at different wavelengths, time durations (5, 10, 15, 20 and 30 mins) and light intensities (1.6, 2.4, 3.2 and 4.0 W/$cm^2$) at fixed distance of 10 cm, which converted to the actual exposure intensities on cells at 0.064, 0.096, 0.128 and 0.16 W/$cm^2$. The OmniCure AC450/P air-cooled UV LED light has a flat light output window large enough to cover the entire cell culture flask with uniform LED light exposure. 2.4 W/$cm^2$ (0.096 W/$cm^2$ actual cell exposure) and 30 mins light treatment a fixed distance of 10 cm was selected for cell treatments discussed in the result section.

D. Extracellular Vesicle (EV) Purification and Characterization.

JAWS II cells were passaged into T-25 (25 $cm^2$) flask and treated with different conditions (near-UV LED light treatment on both imDCs and mDCs) as described above. Immature JAWS II cells without any treatment were set as the control group. The culture medium was then discarded and replaced with fresh medium containing EV-depleted FBS (Gibco, USA) for 48 h. Then cell culture supernatants from differently conditioned JAWS II cells were collected. JAWS II cells-derived EVs were isolated from the supernatant by sequential ultracentrifugation process, as previously reported (Thery C et al. "Isolation and characterization of exosomes from cell culture supernatants and biological fluids," Curr Protoc Cell Biol Chapter 3(Unit 3):22 (2006); Li P et al. "Progress in Exosome Isolation Techniques, Theranostics 7(3):789-804 (2017)). In brief, cells were removed from supernatant by centrifugation at 300×g for 10 min followed by removing cell debris at 2000×g for 30 min. To remove any possible apoptotic bodies and large cell debris, the supernatants were then centrifuged at 10,000×g for 30 min. Finally, culture medium was transferred to ultracentrifuge tube (Thermo Scientific, USA) and small EVs were collected by ultracentrifugation at 100,000×g for 70 min (Sorvall™ MTX150 Micro-Ultracentrifuge, USA). Then small EVs were further washed in 10 mL PBS and pelleted again by ultracentrifugation (100,000×g for 70 min). Purified small EVs were resuspended in 500 μL ice-cold PBS for further study or storage in −80° C.

The size and particle number of isolated small EVs were analyzed by nanoparticle tracking analysis (NTA) using the NanoSight LM10 instrument (Malvern Instruments, UK) equipped with a blue laser (405 nm). Briefly, 25 μL of the final pellet suspension was diluted at 1:20 for EVs derived from mDCs or imDCs and 1:100 for EVs derived from light promoted DC EVs. A solution of 300 μL was injected into the sample chamber of LM10 unit and 5 videos of 30 seconds trajectory monitoring were recorded for each sample. Data analysis was performed with NTA 3.4 software (NanoSight). Software settings for capture and analysis were showed as following: camera level=16, screen gain=1, detection threshold=5. The zeta potential of isolated small EVs was determined by dynamic laser scattering (ZS90 Zetasizer, Malvern Instruments). The morphology of isolated small EVs was verified by transmission electron microscopy (TEM, FEI Spirit TEM 120 kV) imaging following the protocol described previously (Lazaro-Ibanez E et al. "Different gDNA content in the subpopulations of prostate cancer extracellular vesicles: apoptotic bodies, microvesicles, and exosomes," Prostate 74(14):1379-90 (2014)). Briefly, ultra-thin copper grids coated with 400 mesh carbon film (FCF400-Cu-UB, Electron Microscopy Science, USA) was used with glow discharge treatment for 1 min before use. Then, 5 μL EV samples were individually added onto glow-discharged grids and were quiescent for 10 mins at room temperature. The grids were washed with distilled water one time, then negatively stained with filtered 2% aqueous uranyl acetate for 2 mins and dried at room temperature before observation. The TEM imaging power was set at 120 kV by FEI Spirit G2 with a digital camera (Soft Image System, Morada and Gatan Orius SC 1000B CCD-camera).

E. NanoView Microarray for Characterization of EV Surface Markers.

Culture medium was collected and centrifuged at 300×g for 10 min, 2000×g for 30 min, 10000×g for 30 min sequentially to remove cell debris. Per standard protocols provided by NanoView Biosciences (Brighton, MA), processed culture media was diluted appropriately using the EV binding buffer (solution A, pH7.4), then 35 μL of diluted sample was dropped on microarray chips for incubation overnight. Each three chip spots were pre-coated with capture antibodies CD81 (clone Eat-2, mouse, Biolegend), CD9 (clone MZ3, mouse, Biolegend), and negative controls HIgG (clone HTK888, mouse, Biolegend) and RIgG (clone RTK2758, Biolegend). Microarray chips were washed four times with solution A at 150 rpm/min, 3 min for each time. After washing, 300 μL blocking solution was incubated with each chip for 1 h at room temperature and protected from light, which contains three detection antibodies including 0.6 μL Alexa Fluor@647-conjugated CD63 (clone NVG-2, Biolegend), 2 μL Alexa Fluor@488-conjugated CD86 (clone GL-1, Biolegend), and 2.5 μL PE-conjugated MHC class I (mouse, clone AF6-88.5.5.3, Invitrogen) or MHC class II (mouse, clone M5/114.15.2, Invitrogen). Following, microarray chips were washed again with solution A, solution B and distilled water, sequentially, then chips were kept air dry for imaging by ExoView R100 (Nano View Biosciences) equipped with 40× objective lens (Olympus, Japan). Data was analyzed and quantified using off-line ExoViewer3 EAP_v3 software.

F. In Vitro Cellular Uptake Analysis by Confocal Microscopy Imaging.

EVs with a total number of $1\times10^{10}$ were diluted with diluent C to a final volume of 1 mL, per instruction of PKH-26 labeling kit (Sigma, USA). 6 μL PKH-26 dye solution was added and mixed gently, followed by the incubation at room temperature for 5 min (protected from light). The labeling was quenched by adding 2 mL cold 10% BSA in PBS and brought volume up to 8 mL. Afterwards, 2 mL 0.971 M sucrose solution was added by pipetting slowly and carefully into the bottom of ultracentrifuge tubes for maintaining EV-PKH26 solution on the top of sucrose cushion. The solution was then centrifuged at 100,000×g for 90 min at 4° C. The entire solution, including the sucrose layer, was aspirated carefully, retaining the EV pellet for resuspension in 10 mL cold PBS, followed by centrifuge filtration to remove free dyes using Amicon ultra centrifugal filter (10 kDa MWCF, Millipore Sigma, Missouri, USA) at 3000 g× for 40 min at 4° C.

For flow cytometry analysis of JAWS II cell uptake, JAWS II cells were seeded into 24-well plates at a density of $5\times10^4$ per well and allowed to grow for two more days (approximately 80% confluency). Then, the culture medium was discarded and replaced with fresh culture medium containing PKH-26 labelled EVs ($1\times10^9$ particles per cell). Different doses of EVs ($5\times10^8$, $1\times10^9$, $5\times10^9$, $1\times10^{10}$ particles) were also investigated. After 1, 2, 4, and 24 h incubation, cells were digested, harvested, and washed with PBS twice. Finally, cells were resuspended in 500 μL PBS for flow cytometry analysis. The fluorescence intensity was detected at PE channel using Fortessa multicolour flow cytometer (BD Biosciences, USA). For IC-21 uptake, IC-21 cells were seeded into 12-well plates at a density of $1\times10^5$ per well and allowed to grow for three more days (approximately 80% confluency). The following incubation, cell harvest, resuspension, and analysis were same as the procedures described above.

For confocal microscopic imaging, JAWS II cells were seeded into 6-well plate pre-placed with 400 $mm^2$ coverslip at a density of about $2\times10^5$ per well and allowed to grow for 2 days. The medium was then removed and replaced with fresh FBS-free medium containing PKH-67-labeled EV samples at a concentration of $1\times10^9$ for another 1, 2 and 4 h incubation. 30 mins before the end of incubation, lysotracker-red (DND-99, Invitrogen, USA) was introduced into the medium at a final concentration of 100 nM. Then cells were washed twice, fixed with 4% paraformaldehyde for 20 min at room temperature, and counterstained with 4',6-diamidino-2-phenylindole (DAPI, 0.5 μg/mL) for another 5 mins. The coverslips were transferred onto glass microscope slides and applied a drop of antifade mounting media (Thermo Fisher, USA). Fluorescence was captured using Nikon Ti2 fluorescence microscope (Japan).

G. MTT Assay.

To test the cell viability after 365 nm light treatment, different light intensities (0.064, 0.096, 0.128 and 0.16 W/$cm^2$) and time durations (5, 10, 15, 20 and 30 min) were applied to both mature and immature JAWS II DC cells. Afterwards, the culture medium was replaced with fresh complete culture medium and allowed to grow for another 2 days. Then, cells were harvested, centrifuged, and seeded into 96-well plates at a density of about 5000 cells per well, followed by adding 10 μL 3-(4,5-dimethylthiazol-2-yl)-2,5-diphenyltetrazolium bromide (MTT, 5 mg/ml). The immature JAWS II DC cells without light treatment were used as the control group. Cells were processed following the MTT assay protocols per vendor's instruction (Cell Proliferation Assay Kit, Thermo Fisher) and the absorbance was measured at 570 nm. To test the biocompatibility of secreted DC EVs, JAWS II DC cells were seeded into 96-well plates at a density of about 2000 cells per well and allowed to grow for 2 days. The medium was then removed and replaced with fresh medium containing different concentrations of DC EVs ($1.25\times10^8$, $2.5\times10^8$, $5\times10^8$, $1\times10^9$ particles) for incubation at 24, 48, and 72 h. 10 μL of the MTT (5 mg/ml) solution was added into the culture medium at a final concentration of 10% and further incubated for another 4 h. After incubation, the culture medium was removed and then added with 150 μL dimethyl sulfoxide per well. The plates were incubated at 150 rpm/min at 37° C. for 15 min and the absorbance was measured at 570 nm using a microplate reader (Biotek, USA). The immature JAWS II DC cells without incubation with DC EVs were used as the control group.

H. Immune-Stimulatory Functional Assessment.

JAWS II cells were seeded into 12-well plate at a density of about $1\times10^5$ per well and allowed to grow for 2 days. The medium was then removed and replaced with fresh FBS-free medium containing EV samples at a concentration of $1\times10^9$ for incubation at 24, 48 and 72 h. Afterward, cells were harvested and washed with PBS twice, then suspended in 100 μL PBS for flow cytometry analysis of immune-modulatory markers including MHC-I, MHC-II, and CD86. For single-color staining, cells suspension ($1\times10^6$ cells) in 100 μL of ice-cold flow cytometry buffer (PBS, 1% BSA, 0.1% sodium azide) were stained with PE-conjugated MHC-I (clone AF6-88.5.5.3, Invitrogen, 0.25 μg/test), MHC-II (clone M5/114.15.2, Invitrogen, 0.25 μg/test), CD86 (clone GL-1, Invitrogen, 0.25 μg/test) for 1 h at 4° C. in the dark. After staining, cells were washed three times by centrifugation at 400×g for 3 mins and resuspended in 500 μL of ice-cold flow cytometry buffer. In parallel, cells stained with PE-conjugated isotype control antibodies were set as negative control. The fluorescence intensity was detected at PE channel using Fortessa multicolor flow cytometer (BD Biosciences, USA). For double-color staining, cells suspension ($1\times10^6$ cells) in 100 μL of ice-cold flow cytometry buffer (PBS, 1% BSA, 0.1% sodium azide) were double-stained with Alexa Fluor 488-conjugated CD86 (clone GL-1, Biolegend, 0.25 μg/test) and PE-conjugated MHC class I (0.25

μg/test) or MHC class II (0.25 μg/test) for 1 h at 4° C. in the dark. The fluorescence intensity was detected at FITC and PE channels with appropriate compensation using Fortessa multicolor flow cytometer (BD Biosciences, USA).

To determine TNF-α secreted into culture medium, the supernatant was collected after EV isolation. The concentration of TNF-α in the supernatant was detected by TNF-α ELISA Kit (mouse, Invitrogen, USA) according to manufacturing protocols. In brief, 50 μL/well of the supernatant under different conditions was added into the microwell strip precoated with anti-mouse TNF-α and followed by 50 μL/well of biotin-conjugated antibody for 2 h incubation at room temperature with shaking (75 rpm/min). The about 100 μL/well of diluted streptavidin-HRP was incubated for 1 h to develop chemiluminescent detection with about 100 μL/well of tetramethylbenzidine (TMB) substrate for another 15 min incubation at room temperature. About 100 L/well of stop solution was applied and then read at 450 nm using microplate reader. To determine TNF-α in the EVs, 100 μL of EVs were first lysed with 50 μL of radio-immune precipitation assay (RIPA) buffer (Thermo Fisher, USA) containing 1% protease inhibitor cocktail (Thermo fisher, USA). The concentration of TNF-α carried by EVs was then detected according to protocol described above.

I. Oxidative Stress Analysis.

To determine whether cell-stress pathways in cells are activated by light treatment, immature and mature DC cells were treated with 365 nm near UV light (0.096 W/cm2, 30 min), and then seeded into 96-well plates at a density of about 2000 cells per well. Cells were allowed to grow 1, 48, and 96 h post light treatment. Then, 5 μM CellROX Deep Red Reagent in dimethyl sulfoxide was added to each well and the plates were incubated at 37° C. for 30 min. The presence of reactive oxygen species was measured through fluorescence intensity readings at an excitation of 630 nm and emission of 675 nm using a microplate reader (Biotek, USA). Untreated mature and immature cells were set as a control, along with 800 μM hydrogen peroxide treated cells as the positive control.

To test the effect of light promoted EVs on recipient cells, EVs were collected after two days of culture in fresh medium from imDC and mDC cells with light treatment at 0.096 W/cm2 for 30 min. Then, imDC cells were seeded into 96-well plates at a density of about 2000 cells per well with the different DEV samples at variable concentrations (0, $2.3\times10^6$, $5.5\times10^7$ particles) for incubation at 24, 48, and 72 h. Then, 5 μM CellROX Deep Red Reagent in dimethyl sulfoxide was added to each well and the plates were incubated at 37° C. for 30 min. After incubation, the presence of reactive oxygen species in the recipient cells was measured through fluorescence intensity readings at an excitation of 630 nm and emission of 675 nm using a microplate reader (Biotek, USA). The imDC EVs and mDC EVs were set as the control groups. The 800 μM hydrogen peroxide treated imDC cells were set as the positive control group.

J. In Vivo Biodistribution Study.

To perform in vivo biodistribution study, EVs were first labeled with a near-infrared lipophilic carbocyanine dye DiR (Invitrogen, USA). Briefly, 5 μL of DiR, at a concentration of 1 mg/mL in ethanol, was mixed with $5\times10^{10}$ EVs in 1 mL PBS and incubated at room temperature for 20 min. Subsequent spin column purification was performed to remove ethanol and the unincorporated DiR according to PKH-67 labeling protocol described above. Both male (n=4) and female (n=4) C57BL/6 mice were intravenously injected with freshly prepared DiR-labeled EV samples through the tail at a dose of $1\times10^{10}$ EVs (about 0.15 mL) per mouse. The in vivo biodistribution of these DiR-labeled EVs in live mice at 2, 6, 24, 48, and 72 h was evaluated using IVIS Lumina II optical imaging system (Xenogen, Caliper Life Science, USA). Before imaging, mice were pre-anesthetized using 2-4% isoflurane in 100% oxygen. Subsequently, the mice were euthanized, and major organs (heart, liver, lung, kidney, spleen, and lymph nodes) were harvested at the last time interval at 72 h for ex vivo imaging. Imaging conditions: fluorescence imaging with filter sets was used to perform optical studies. The scanning parameters include: excitation=730 nm, emission=780 nm, field of view=13.5 cm and fluency rate=2 mW $cm^{-2}$. The camera was set to a maximum gain, a binning factor of 4, and a luminescent exposure time of 4 s. The data was analyzed with the IVIS software (Living Image Software for IVIS). All procedures were approved by the IACUC committee of the University of Florida, and followed the guidelines established by NIH.

K. Evaluation of In Vivo Immunogenicity.

Male and female C57BL/6 mice were intravenously injected with freshly prepared different EV samples through the tail at an equivalent dose of $1\times10^{10}$ EVs per mouse, respectively. 72 h post-injection, spleen and lymph nodes (LNs) were isolated and prepared into single-cell suspensions. Briefly, spleens and LNs were ground and homogenized in fresh RPMI-1640 medium, then filtered with 70 μm cell strainer (Fisher Scientific). Before homogenized in RPMI-1640 medium, ground LNs were pre-incubated with 1 mg/mL of Collagenase IV (Stemcell Technologies, USA) for 30 min under the condition of 37° C. and 75 rpm/min. The resulting cells were washed with PBS and lysed by red blood cell lysis buffer (Thermo Fisher, USA). To analyze DCs maturation, splenocytes and lymphocytes were double-stained with FITC-anti-CD86 antibody and PE-anti-CD11c antibody, PE-anti-MHC-I antibody, as well as PE-anti-MHC-II antibody. All samples were analyzed using Fortessa multicolor flow cytometer (BD Biosciences, USA) at FITC and PE channels with appropriate compensation and 50,000 events were counted for each sample. In addition, peripheral blood was collected simultaneously from mice to isolate serum for TNF-α ELISA analysis.

L. Statistical Analyses.

Multiple comparisons between different groups were analyzed by one-way AVONA. A comparison between the experimental group and control group was analyzed by the paired Student's t-test. $p<0.0332$, 0.0021, 0.0002, and 0.0001 were considered a statistically significant difference and remarked with *, , * and ****, respectively.

M. Results.

1. NEAR-UV LED LIGHT PROMOTED HIGH-EFFICIENT CELLULAR PRODUCTION OF EVS

Figure 3:
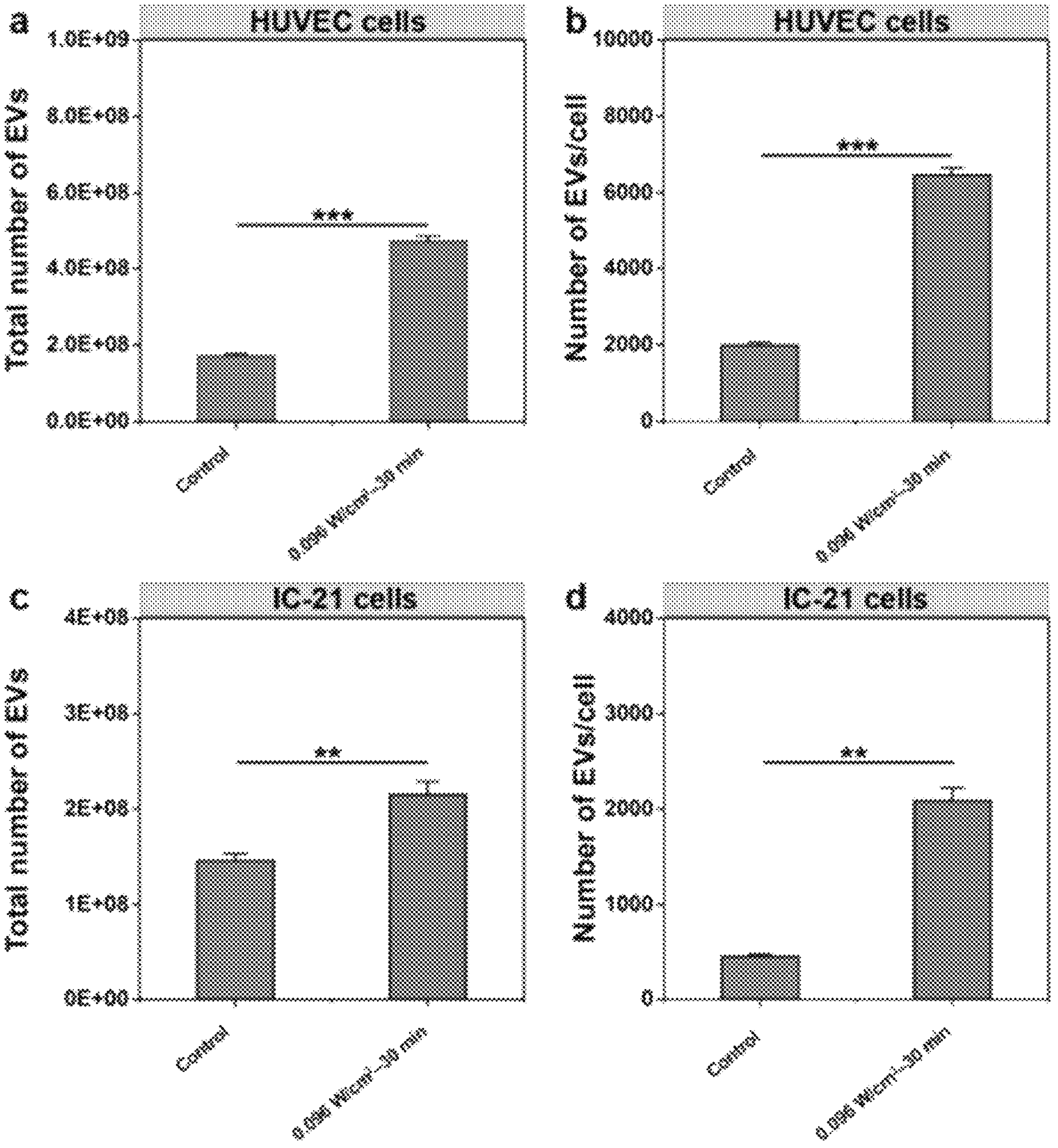
FIG. 3. (a) Total number of EVs secreted by HUVEC cells and their average cellular EV secretion rate (b) after light treatment (365 nm) at optimized light intensity and exposure time. Total number of EVs secreted by IC-21 macrophages (c) and their average cellular EV secretion rate (d) after light treatment (365 nm) at optimized light intensity and exposure time. p<0.0021 and *p<0.0002.
Figure 4:
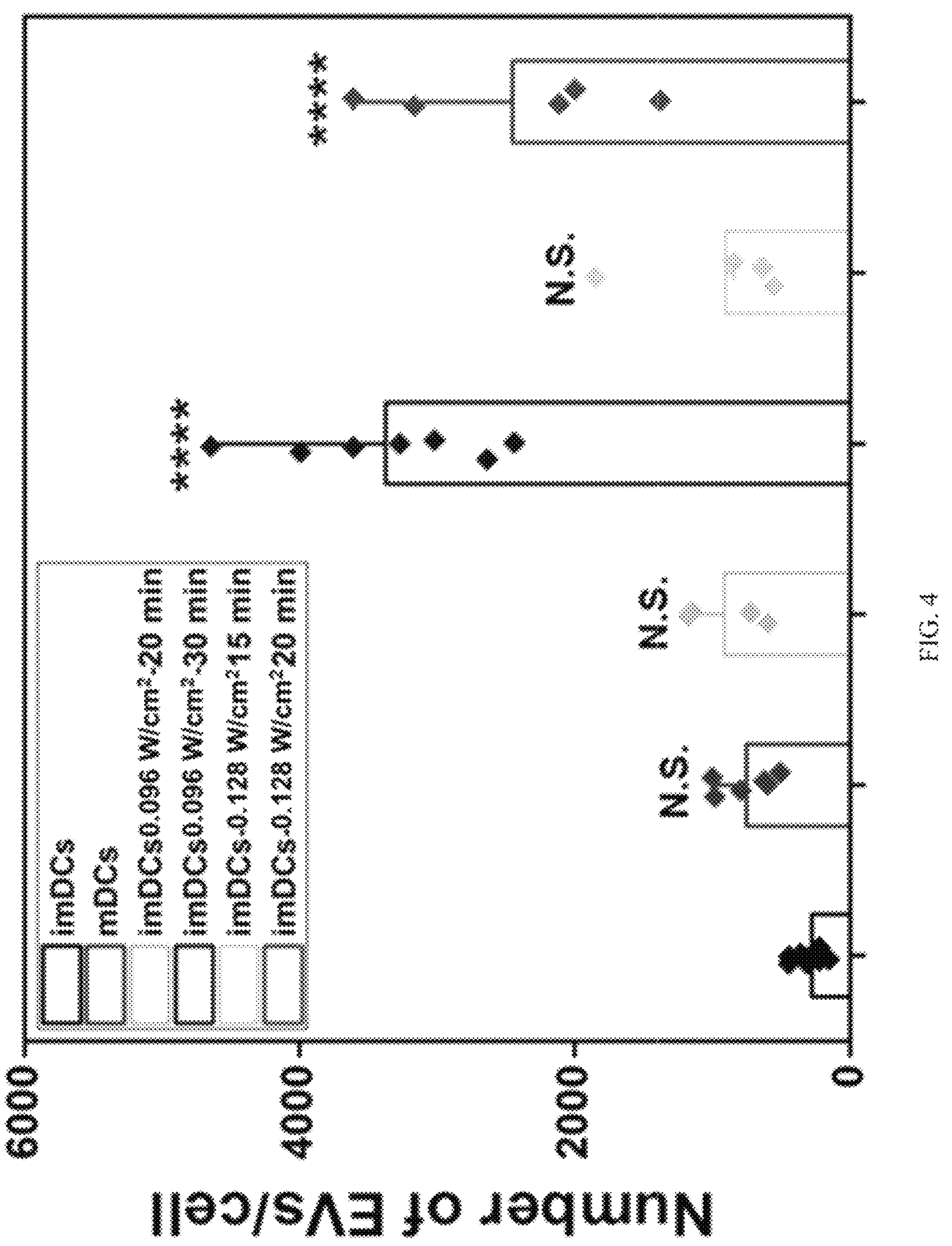
FIG. 4. Total number of EVs secreted by imDCs and mDCs treated with variable light exposure conditions repeated on different days for confirming the robustness and reproducibility. ****p<0.0001.
Figure 5E:
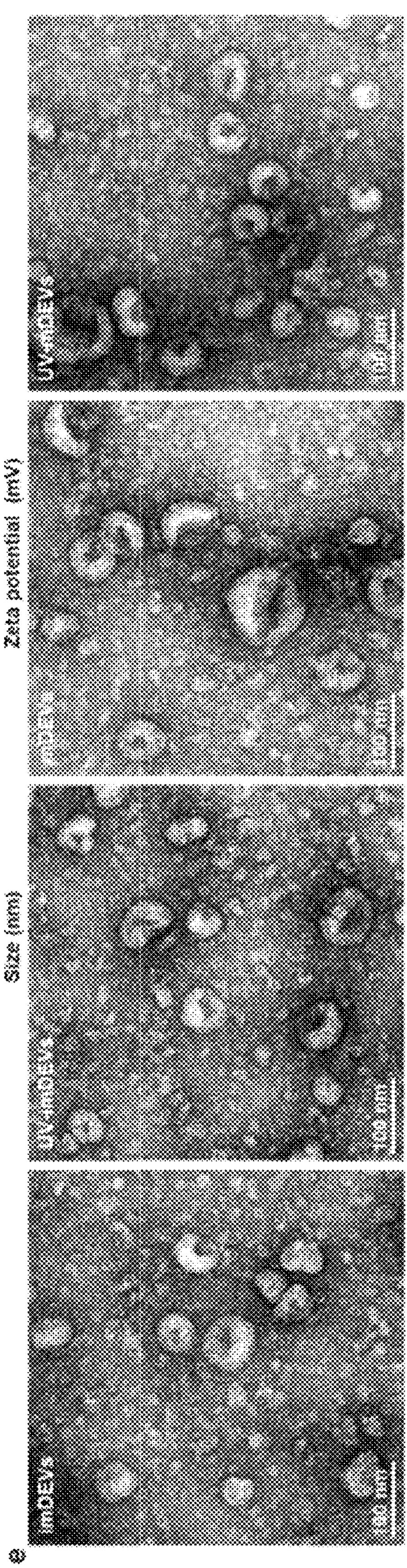
FIG. 5E. TEM images showing the morphology of light-promoted EVs secreted from both imDCs and mDCs, which is consistent with the control group of native EVs.

The influences of LED light from different wavelengths (FIG. 1; 365 nm, 405 nm, and 488 nm) and intensities (FIG. 2) on the secretion dynamics of EVs were investigated using JAWS II cells, a mouse bone marrow DC cell line. The JAWS II was selected as a model for DC cells because it is a professional antigen presenting cell line that is stable and whose characteristics are well-documented. We observed that near UV LED at 365 nm promoted high-efficient EV production from cultured cells compared to that at 405 nm or 488 nm (FIG. 1). The production rate from near UV, 365 nm, LED light promoted EVs was found to correlate with light intensity and exposure time. Similar observation on IC-21 cells (a mouse macrophage cell line) and HUVEC cells supports that near UV LED at 365 nm is suitable to reliably trigger enhanced cellular production of EVs regardless of cell type (FIG. 3). Higher light intensity and longer exposure time resulted in more production of EVs (FIG. 2). After testing several light conditions, we found that a threshold of light exposure with intensity at 0.096 W/cm$^2$ for 30 min was able to efficiently turn on the cellular machinery for highly enhanced production of EVs, as compared with their corresponding cells without light treatment (FIG. 4). At this light exposure, the average ability of cellular secretion of EVs was significantly increased from both immature and mature DC. About 13.3-fold or 5.1-fold enhancement of EV secretion from both light-induced imDCs (UV-imDEVs) or mDCs (UV-mDEVs) were observed, compared to EVs from imDCs (imDEVs) or mDCs (mDEVs) without light treatment (FIG. 5A). The light promoted EVs were of similar size (FIG. 5B), zeta potential (FIG. 5C), and morphology (FIG. 5E) compared to their corresponding control groups without light treatment. Additionally, we investigated TNF-α levels from secreted DC-EVs, as TNF-α is an essential pro-inflammatory cytokine for immunity regulation. We did not observe noticeable changes in TNF-α levels from light produced imDEVs or UV-mDEVs compared to their corresponding control groups, which indicated that consistent immune modulator function is retained using the described light treatment, while the EV production rate is significantly enhanced (FIG. 5D).

Figure 6C:
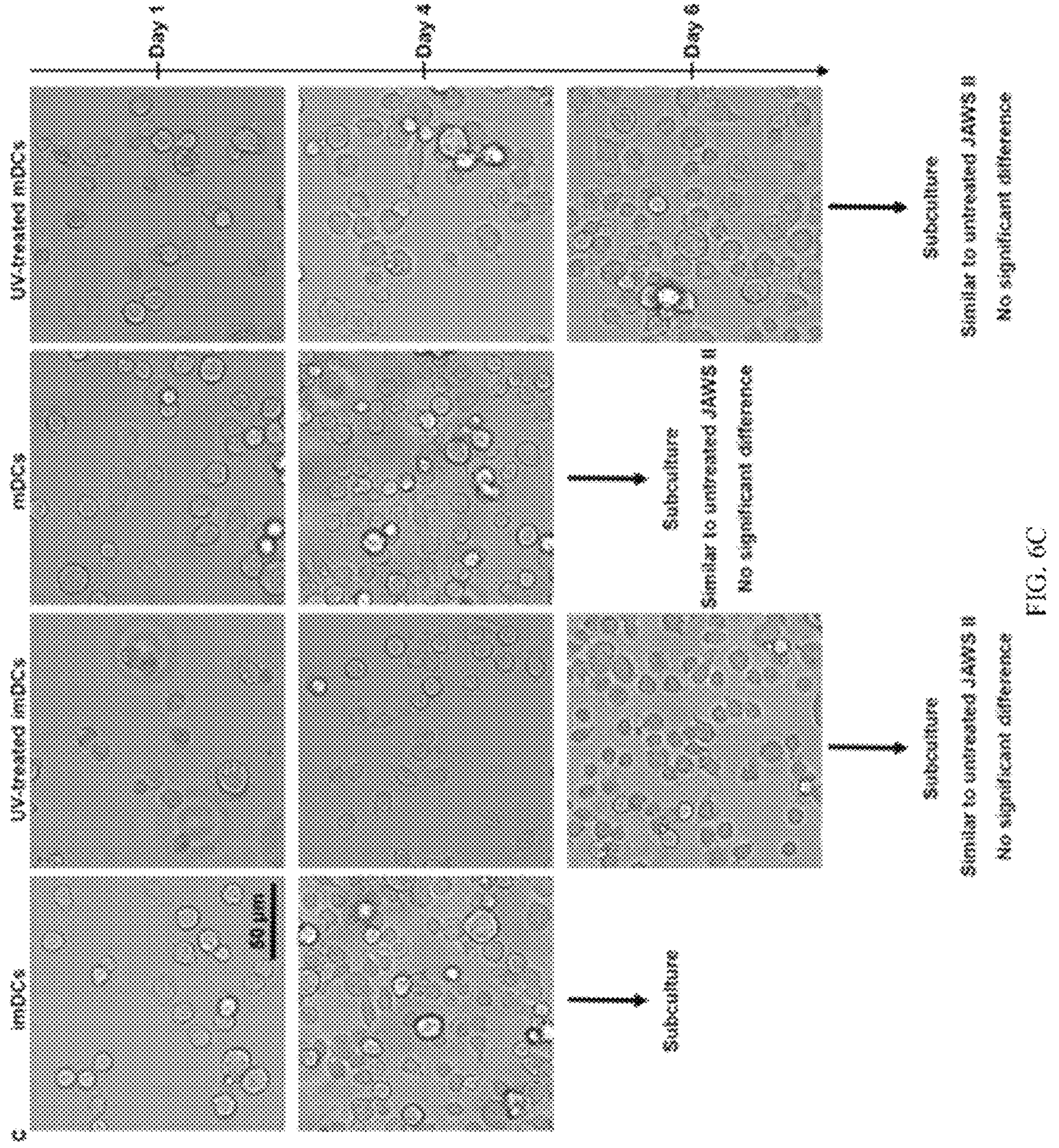
FIG. 6C. The bright field images showing the cell growth morphology and behavior for light treated imDCs and mDCs at the condition of 0.096 W/cm$^2$ for 30 min, compared to the control group imDC cells without light treatment.

Light wavelength around or below 310 nm has been reported to be harmful for cell viability (Masuma R et al. "Effects of UV wavelength on cell damages caused by UV irradiation in PC12 cells," J Photochem Photobiol B 125: 202-8 (2013)). 250-270 nm UV light has been used for inducing gene damage and cell apoptosis (Gao L et al. "Effects of four commonly used UV filters on the growth, cell viability and oxidative stress responses of the *Tetrahymena thermophila*," Chemosphere 93(10):2507-13 (2013); Gary A S et al. "Apoptosis, the only cell death pathway that can be measured in human diploid dermal fibroblasts following lethal UVB irradiation," Sci Rep 10(1):18946 (2020)). However, the influence of longer wavelengths at 365 nm light on cell growth remains to be investigated. We investigated imDC cell viability under the influence of different exposure times and intensities of 365 nm LED light (FIG. 6A). As shown in FIG. 6, two days after light treatment, the majority of cells maintained >80% cell viability under light intensity below 0.128 W/cm$^2$. At light exposure of 0.096 W/cm$^2$ for 30 min, cell viability for both imDCs or mDCs showed only a slight decrease compared to corresponding control cells without light treatment (FIG. 6). We observed that light treated DC cells required two more days to reach 90-100% confluency compared to their native cells without light treatment, which require 4 days to reach confluency for subculture (FIG. 6). At the confluency status, the cells have similar growth capacity regardless of the influence of light treatment (FIG. 6). The data indicate that near UV 365 nm light (e.g., 0.096 W/cm$^2$ for 30 min) minimally influences cell growth and that cell recover to normal status in 2 days. In order to further assess whether light treatment could activate the cell-stress pathway, we tested the production and accumulation of reactive oxygen species (ROS) in cells exposed to near UV 365 nm light at 0.096 W/cm$^2$ for 30 min as shown in FIG. 27. The light treatment groups did not show significant differences compared to the control group without light treatment in terms of ROS level, along the time course of 1, 48, and 96 h post light treatment. In contrast, the positive control group of DCs treated with $H_2O_2$ displayed a significantly enhanced ROS level, and the ROS level gradually reduced along time until 96 h (FIG. 27). We also investigated whether the light-promoted DC-EVs induced cellular oxidative stress on recipient cells. We harvested EVs after 2 days of culture from light treated DCs, compared with EVs derived from DCs without light treatment as the control group. By applying different concentrations of DC-EVs (0, 2.5×10$^6$, 5.5×10$^7$ particles) for dosing recipient imDCs, we monitored ROS levels after 24, 48, and 72 h, and did not observe noticeable differences from light-promoted DC-EVs compared with control groups. It has been reported that low-dose, long-wave UV light does not affect gene expression from human mesenchymal stem cells (Wong D Y et al. "Low-Dose, Long-Wave UV Light Does Not Affect Gene Expression of Human Mesenchymal Stem Cells," PLOS One 10(9): e0139307 (2015)). Our observation is in line with the reported study. The parent DCs can be passaged for continuous usage.

Figure 6D:
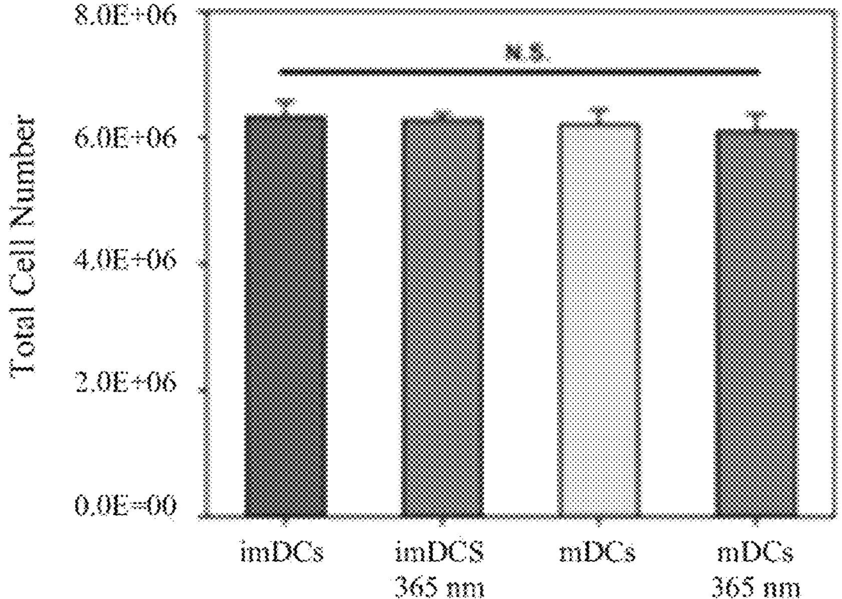
FIG. 6D. The cell density under 90-100% confluency of light treated imDCs and mDCs, compared to the cell density under confluency from control groups of imDCs and mDCs without light treatment.

Higher intensity light treatment at 0.16 W/cm$^2$ (4 W/cm$^2$ light at 10 cm) reduced cell viability to about 65% after 30 min exposure. Lower intensity light treatment, at 0.064 W/cm$^2$, 0.096 W/cm$^2$ and 0.128 W/cm$^2$, did not result in noticeable abnormal cell growth behavior. At 0.128 W/cm$^2$, the cell viability (FIG. 6B) and growth behavior (FIG. 6C) for subculture and passaging were comparable to the control group without light treatment, and both groups reached to about 6.7×10$^6$ cells at the 90-100% confluency (FIG. 6D). This observation also aligned with reported study that low-dose, long-wave UV light does not affect gene expression from human mesenchymal stem cells (Wong D Y et al. "Low-Dose, Long-Wave UV Light Does Not Affect Gene Expression of Human Mesenchymal Stem Cells," PLOS One 10(9):e0139307 (2015)). Thus, the parent DCs can be passaged for continuous usage.

Figure 5F:
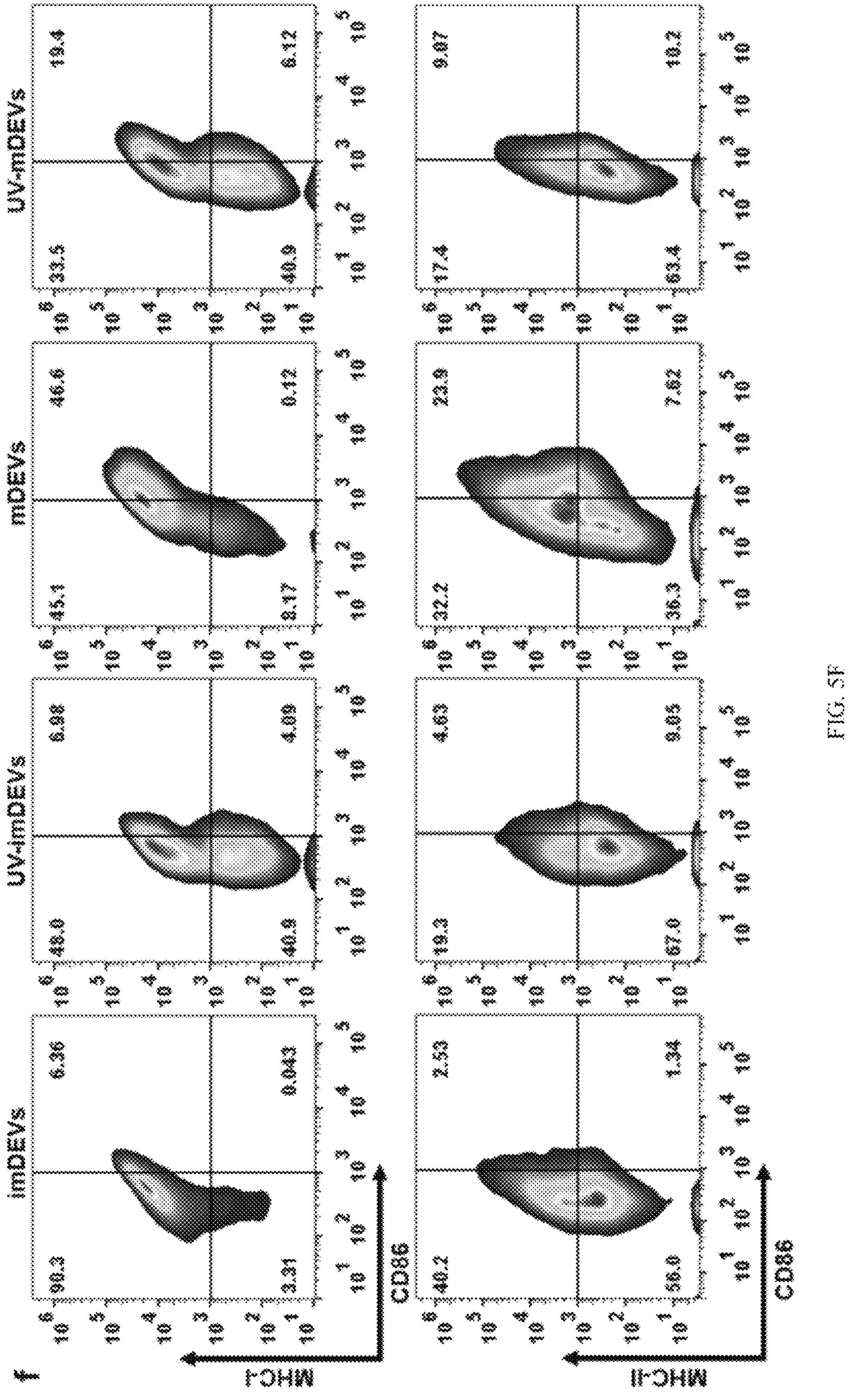
FIG. 5F. Representative flow cytometry analysis of MHC-I, MHC-II, and CD86 marker expression levels from immature and mature DCs with or without light treatment. Cells were immunostained with AF488-conjugated CD86 and PE-conjugated MHC class I/II.

In order to maintain sustainable, high-efficient EV production ability from cell cultures, we also investigated the parent cell immune function after light treatment. Serving as antigen presenting cells, DCs, particularly mDCs, express surface markers MHC-I, MHC-II, and CD86 for regulating immune responses and activating T cells. We studied these surface marker expression levels via flow cytometry and did not observe a noticeable influence of light treatment on imDCs (FIG. 5F-G). For the mDCs group, higher expression levels (about 7-9 fold) of MHC-I, MHC-II, and CD86 were observed compared with imDCs. However, light treatment reduced marker expression by nearly half (FIG. 5F-G). In our cytokine study, parent cell TNF-α levels were slightly reduced from both imDCs and mDCs (FIG. 5H) after light treatment, but the TNF-α levels carried by their correspondingly secreted EVs remained the same (FIG. 5D). It is possible that reduction of surface marker expressions (MHC-I, MHC-II, and CD86) from mDCs could be attributed to substantially increased output transport via EVs. Therefore, we investigated immune marker expression levels from secreted EVs in the next step.

2. IMMUNE MARKER EXPRESSION FROM LIGHT PROMOTED DC-EVS

Figure 7C:
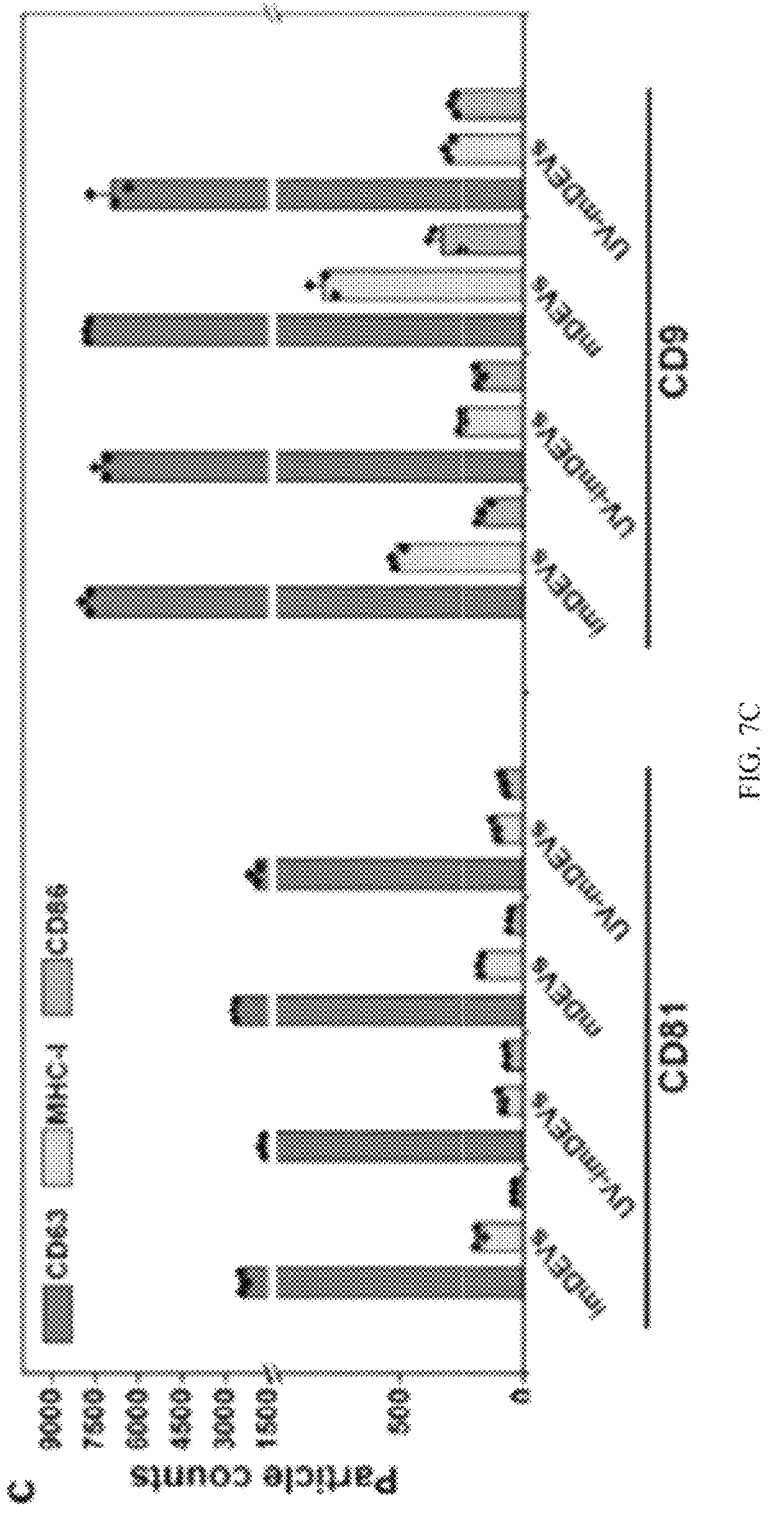
FIG. 7C. Particle counts of captured CD63+, MHC-I+, and CD86+ DEVs from different EV sample conditions on both CD81 and CD9 capture spots (n=3).
Figure 7D:
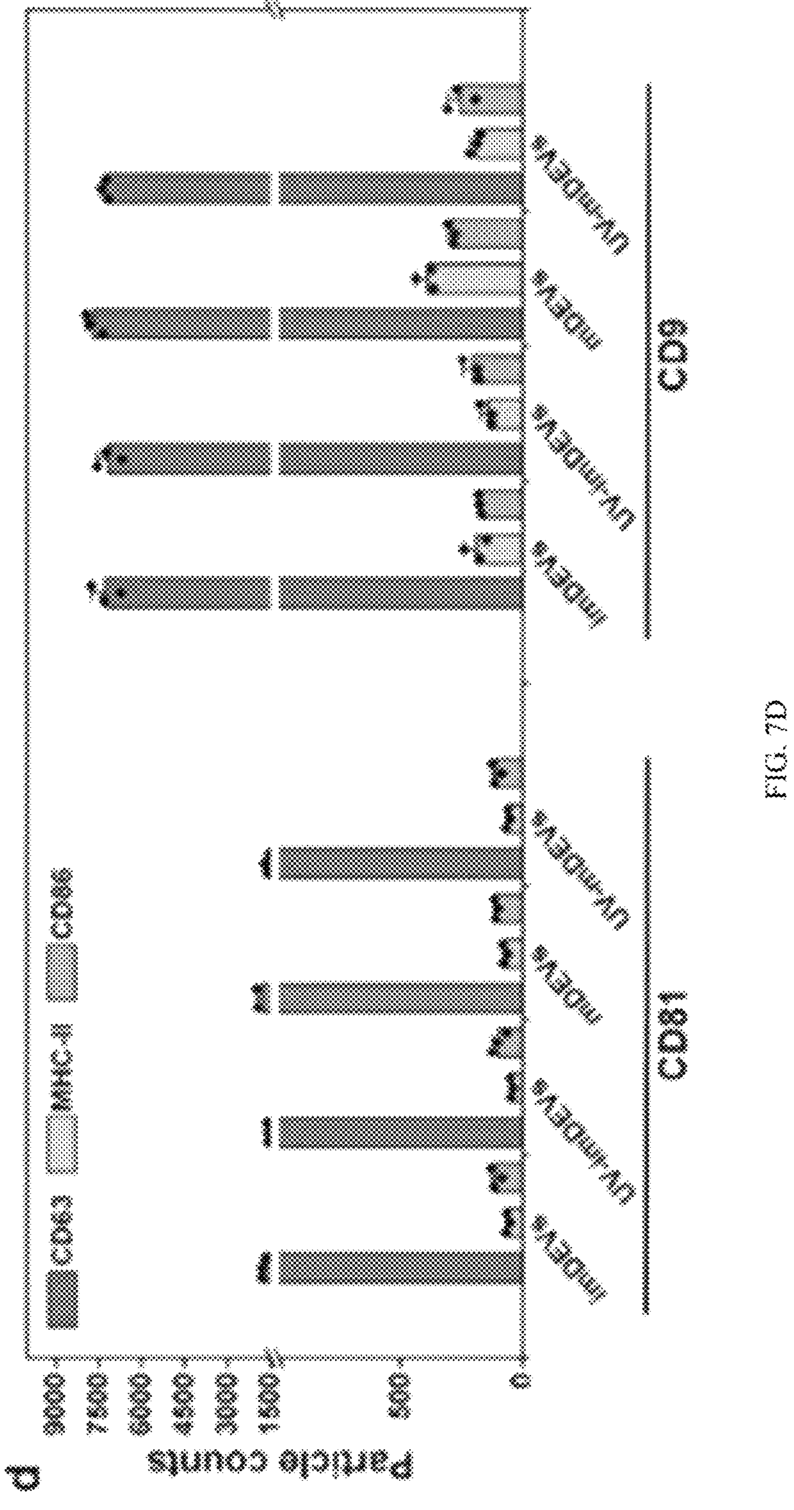
FIG. 7D. Particle counts of captured CD63+, MHC-II+, and CD86+ EVs from different EV sample conditions on both CD81 and CD9 capture spots (n=3).
Figure 8:
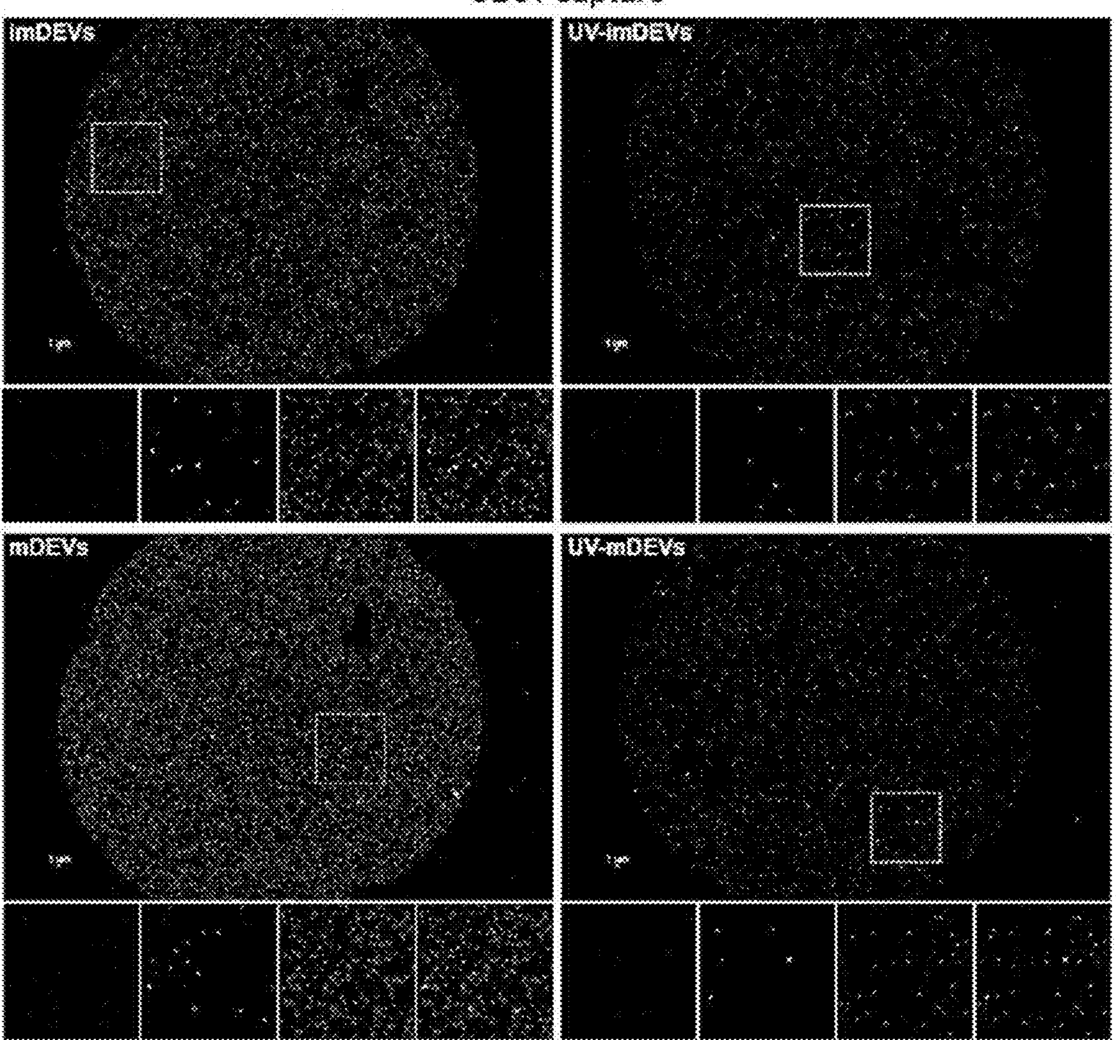
FIG. 8. Representative fluorescence microscope imaging of CD63+ (red), MHC-I+ (green), CD86+ (blue) EVs on CD81 capture spot, dotted frames are showing enlarged individual channel and merged channel.
Figure 9:
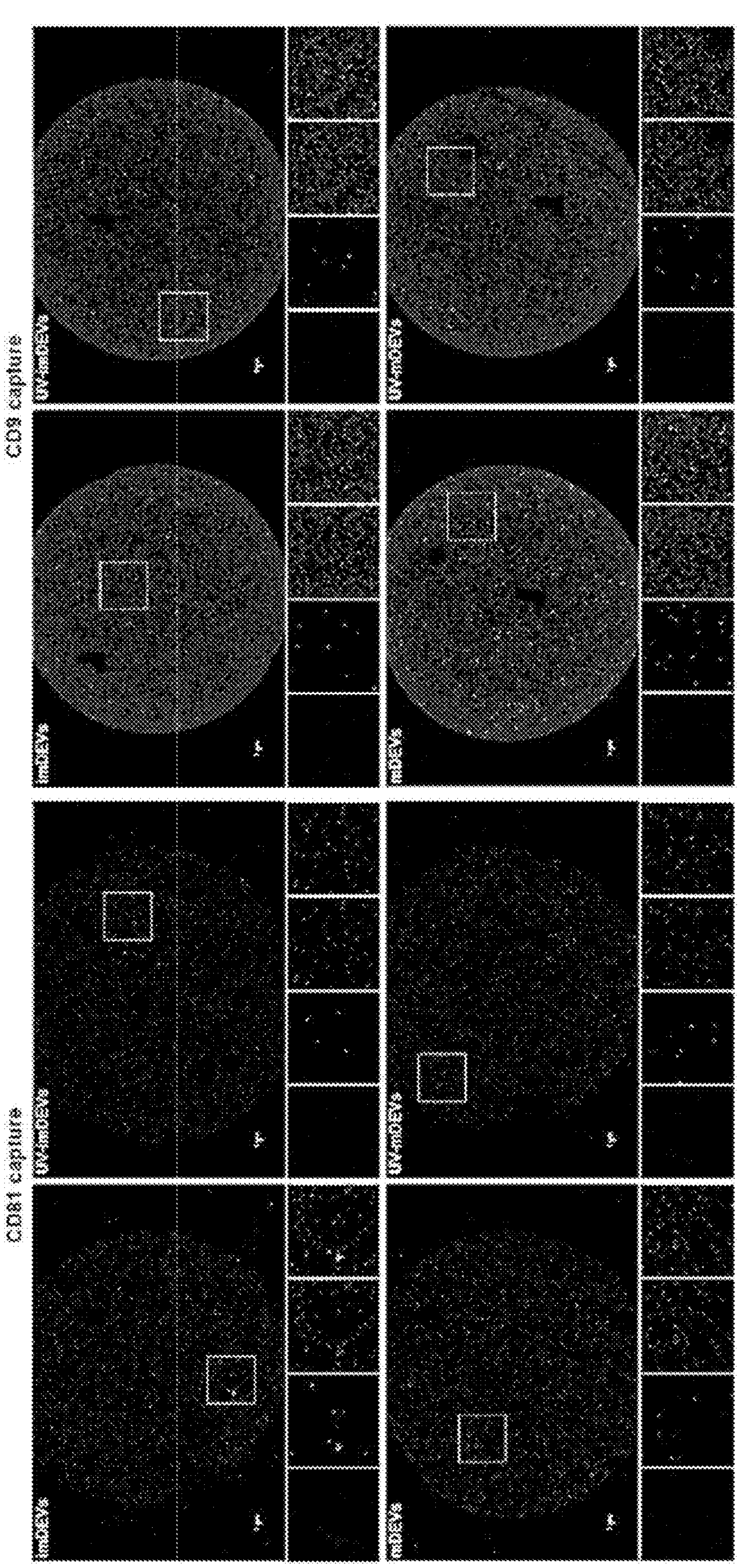
FIG. 9. Representative fluorescence microscope imaging of CD63$^+$ (red), MHC-II$^+$ (green), CD86$^+$ (blue) EVs on CD81 capture spots and CD9 capture spots, dotted frames are showing enlarged individual channel and merged channel.
Figure 10:
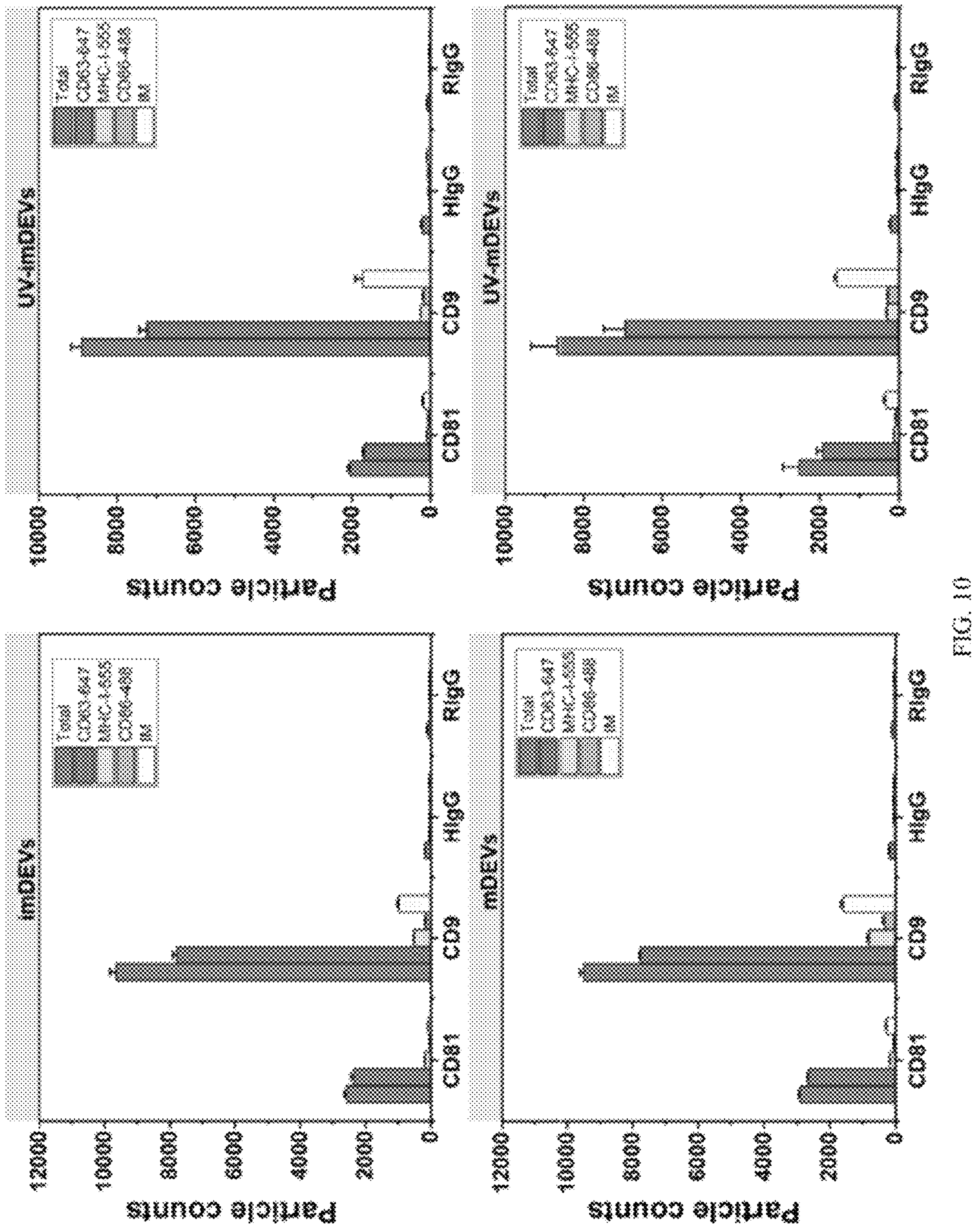
FIG. 10. Particle counts of total, $CD63^+$, $MHC-I^+$, $CD86^+$, $IM^+$ EVs captured in each spot in each chip pre-incubated with different conditions-treated culture medium. Data represent means±SD (n=3).
Figure 11:
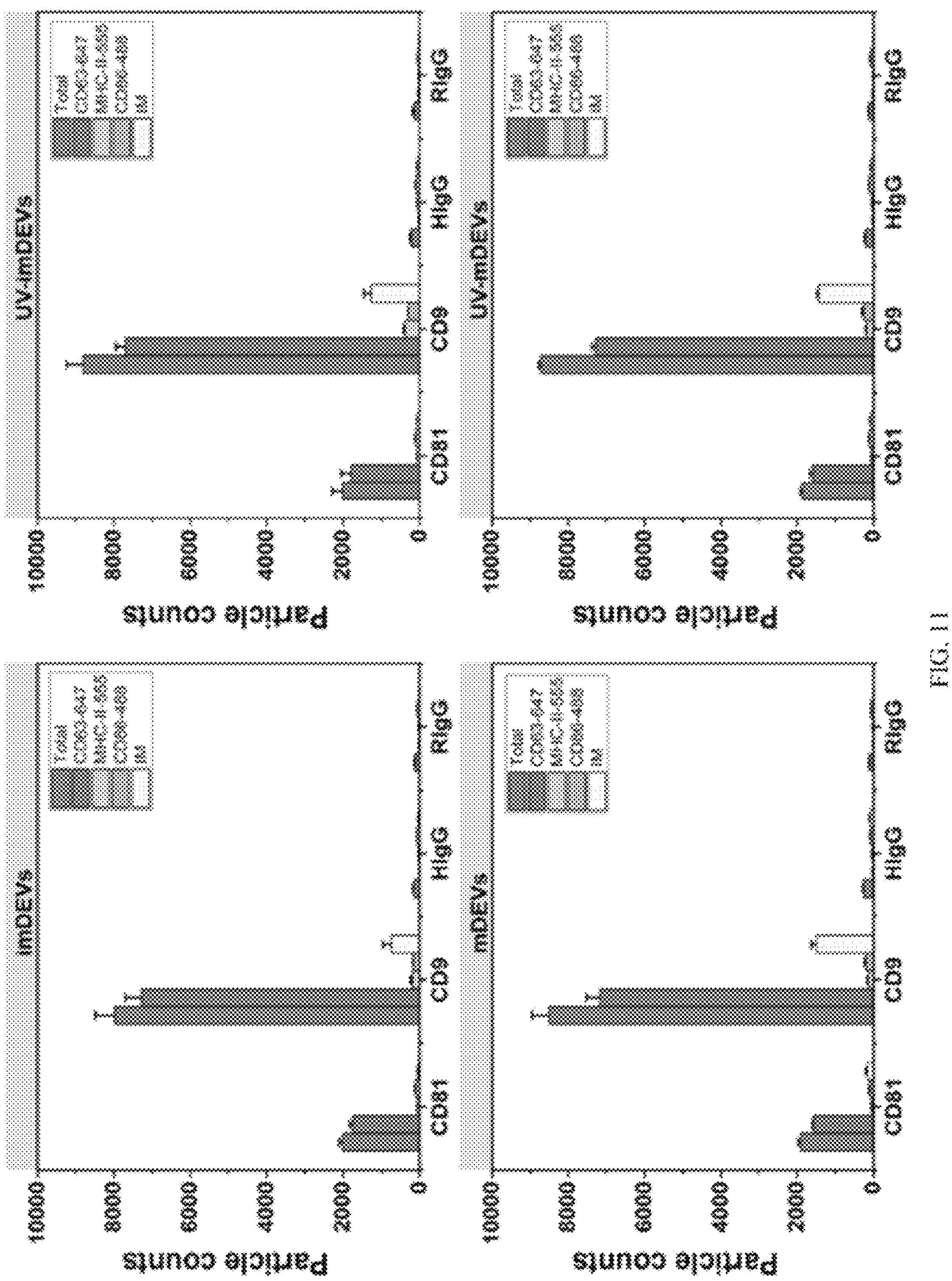
FIG. 11. Particle counts of total, $CD63^+$, $MHC-II^+$, $CD86^+$, $IM^+$ EVs captured in each spot in each chip pre-incubated with different conditions-treated culture medium. Data represent means±SD (n=3).

In order to further characterize the immune activity of light-promoted DC-EVs, we employed a single-EV microarray imaging technology from NanoView to directly determine whether light promoted DC-EVs were significantly immune potent with expression of functional markers. The specific antibody capture on each Nano View chip spot allowed the antibody capture-based immobilization of EV samples for further immune-probing with up to three fluorescently labeled antibodies (here used CD63, MHC-I/-II, and CD86 antibodies) (FIG. 7A). Fluorescence images of CD81 and CD9 capture spots displayed each single EV clearly with either individual or colocalization of antibody probing (CD63 in red, MHC-I/II in green, CD86 in blue) (FIG. 7B, FIG. 8-9). The isotype spots (HIgG or RIgG) were used as the background and non-specific control (FIG. 10-11), which showed negligible EVs capture in either total counts or individual marker counts. We observed that the total EV counts from CD9 antibody capture were always about 4-fold higher than that from CD81 antibody capture, regardless of the measurement settings, which may indicate that majority populations of DC-EVs possess CD9 expression, but not CD81 expression (FIG. 7C-D). Thus, probing of corresponding immune functional surface markers MHC-I, MHC-II, and CD86 from CD9 captured EVs could better represent the immune potency from the total population of light promoted DC-EVs.

CD63 is a common structural and functional protein during EV biogenesis, which makes $CD63^+$ EV counts much higher than that from $MHC\text{-}I^+$ and $CD86^+$ counts. On the other hand, CD63 can serve as the internal EV reference marker to assess total captured EVs, which exhibits comparable abundance between all samples and chip spots, indicating consistent and reproducible measurements (FIG. 7C-D). With CD63 as the internal reference, we conducted two parallel measurements to assess the expression levels of both MHC-I and MHC-II with CD86 under the influence of our light-based EV production conditions in FIG. 7C-D. The relative percentage of surface markers normalized to total captured EVs was used, which showed that mDC EVs possessed slightly higher expression of MHC-I, MHC-II, and CD86 than that from imDC EVs (FIG. 12). The observation is consistent with the literature report that mDC EVs possess stronger elicitation of immune responses (Yin W et al. "Immature dendritic cell-derived exosomes: a promise subcellular vaccine for autoimmunity," Inflammation 36(1): 232-40 (2013)). We did not observe significant differences of these marker expressions between light promoted DC-EVs and native DC-EVs from both mDCs and imDCs. Taken together, light-induced EV production caused little or no influences on their immune marker expressions. Retaining essential immune surface markers on DC-EVs is important in immunity regulation. The light-promoted DC-EVs retain immune-modulation functional markers, while having significantly boosted production rate, which is desired for developing population-based doses at sufficient scale.

Because the co-expression of MHC-I or MHC-II with CD86 could represent the potency for T cell activation, we analyzed such co-expression levels of MHC-I, MHC-II and CD86 in various combinations by utilizing NanoView colocalization imaging. The co-expression of CD63/MHC-I/CD86, CD63/MHC-II/CD86, MHC-I/CD86, MHC-II/CD86, or CD63/CD86 did not show significant changes under different DC-EV conditions with or without light treatment, although MHC-I or MHC-II alone exhibited a slight reduction after light treatment. Overall, the immune profile patterns are comparable within imDC EVs or mDC EVs, regardless of light treatment. The mDC EVs always possess higher expression of MHC proteins and CD86 than that from imDC EVs, which is consistent with literature reported observation (Yin W et al. 2013; Pang X L et al. "Immature dendritic cells derived exosomes promotes immune tolerance by regulating T cell differentiation in renal transplantation," Aging (Albany NY) 11(20):8911-8924 (2019)).

3. LIGHT PROMOTED DC-EVS ARE INTERNALIZED THE SAME AS THE NATIVE DC-EVS

Figure 13A:
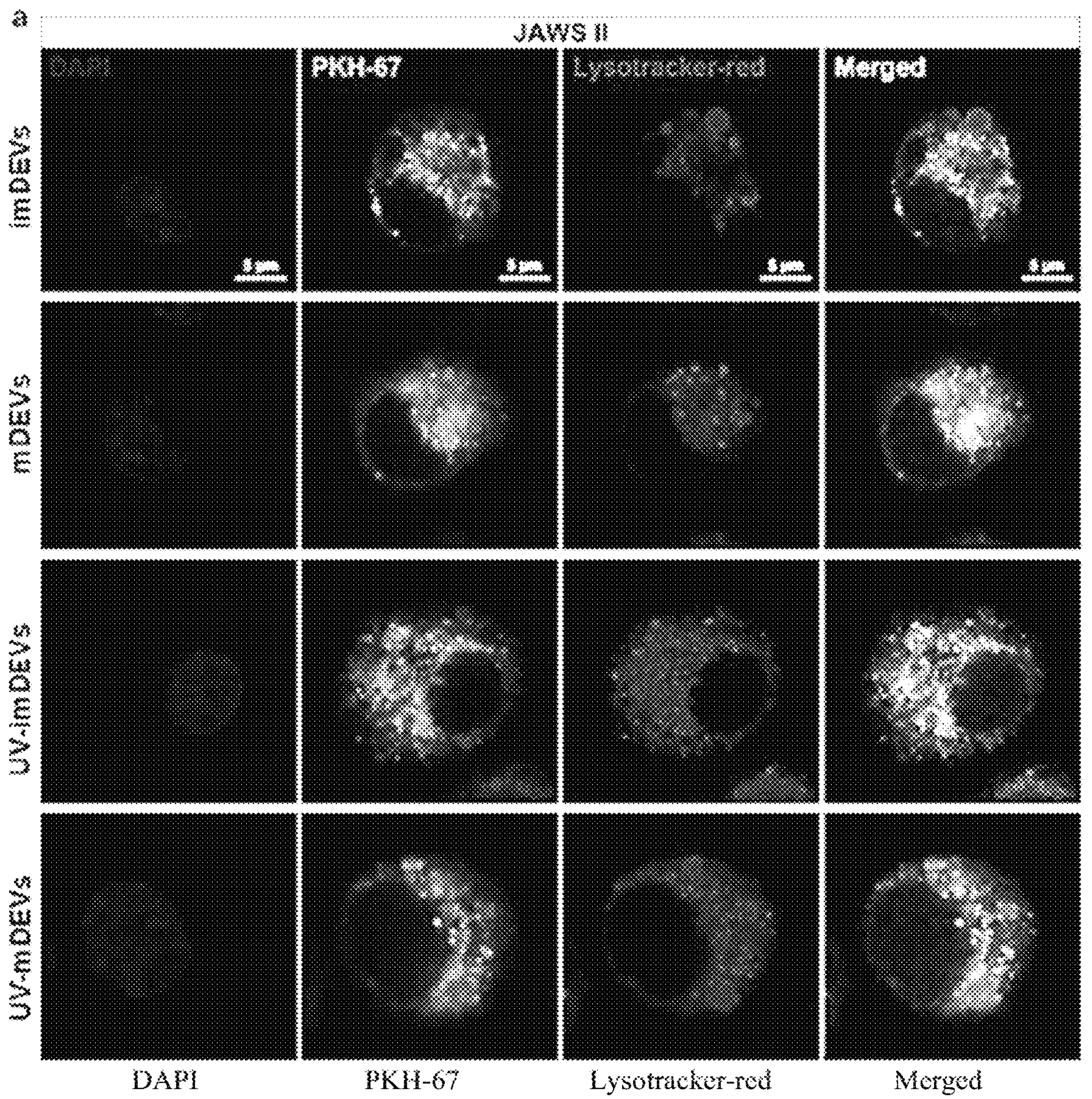
FIG. 13A. Evaluation of the internalization behavior of near UV-visible light-promoted DEVs. Confocal images showing the internalization of different DEVs by immature JAWS II cells. DEVs were labelled with PKH-67 in green for incubation of 1 h. Cells were labelled with lysosomal tracker in red and nucleus in blue.
Figure 13B:
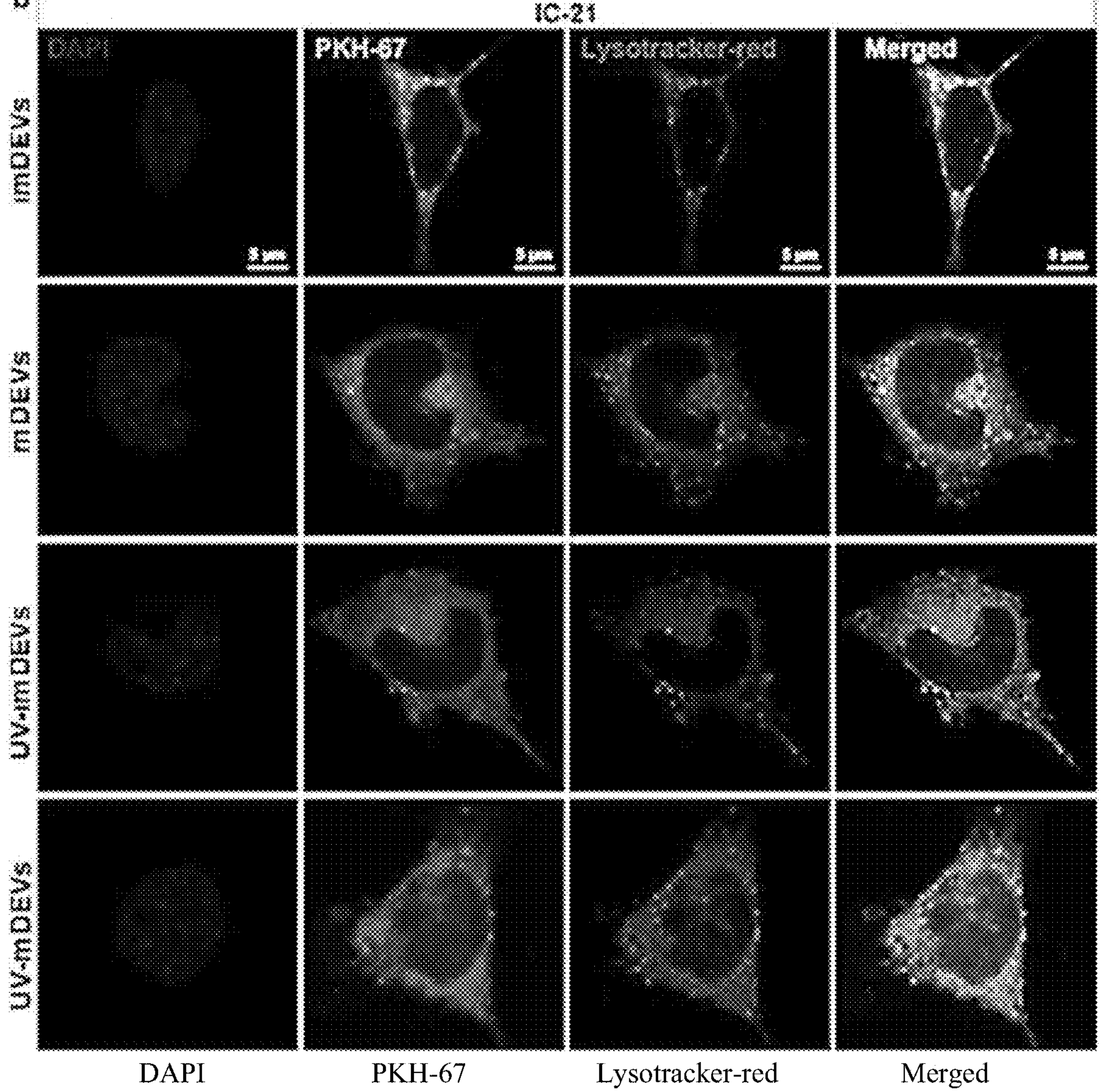
FIG. 13B. Evaluation of the internalization behavior of near UV-visible light-promoted DEVs. Confocal images showing the internalization of different DEVs by IC-21 macrophage cells. DEVs were labelled with PKH-67 in green for incubation of 1 h. Cells were labelled with lysosomal tracker in red and nucleus in blue.
Figure 13C:
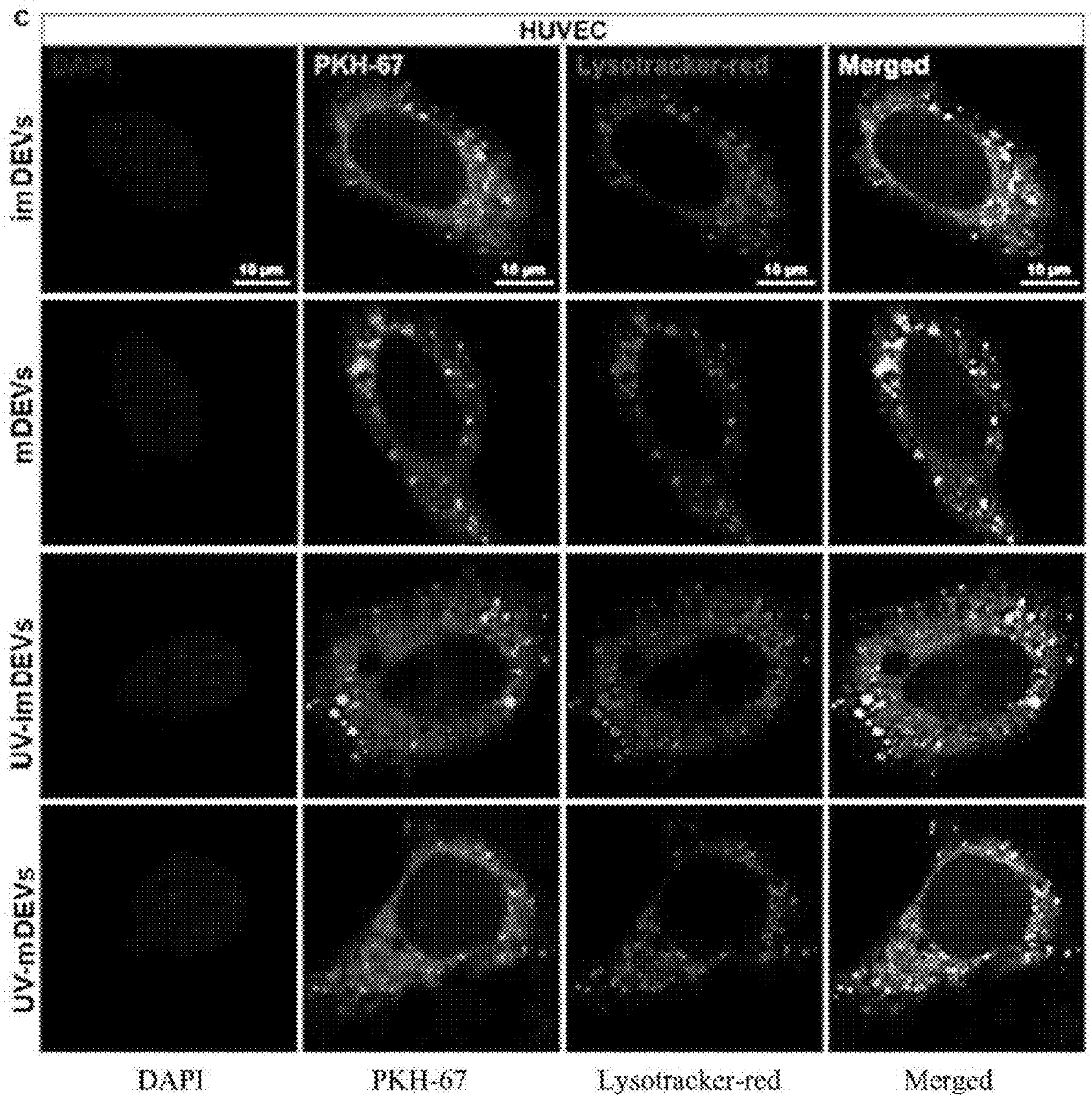
FIG. 13C Evaluation of the internalization behavior of near UV-visible light-promoted DEVs. Confocal images showing the internalization of different DEVs by HUVEC cells. DEVs were labelled with PKH-67 in green for incubation of 1 h. Cells were labelled with lysosomal tracker in red and nucleus in blue.
Figure 13D:
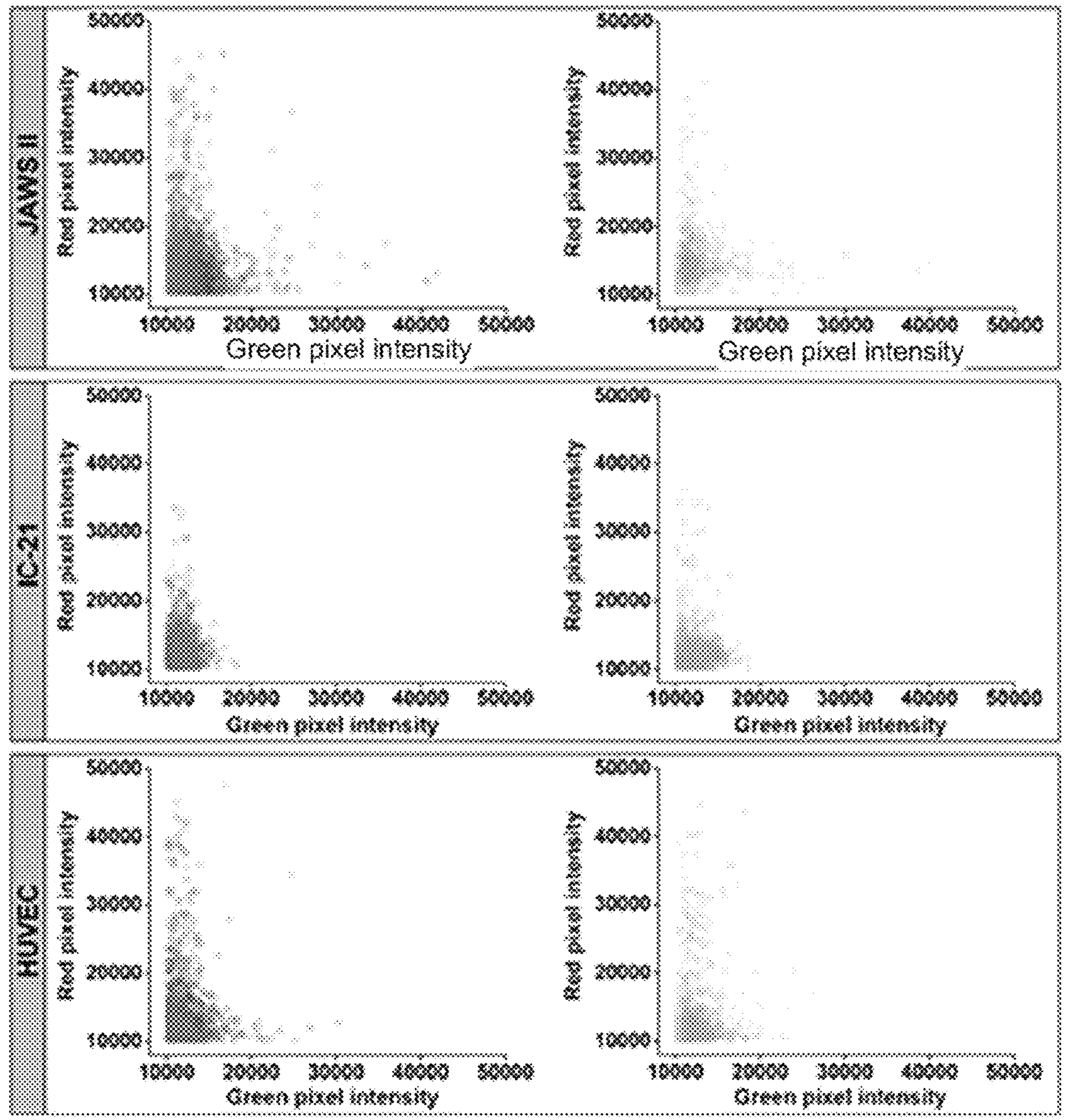
FIG. 13D. Scatter plot analysis of dispersion degree between DEVs internalization and lysosome colocalization. The comparison was made for assessing uptake of near UV-imDEVs (red dots) and imDEVs (black dots), as well as near UV-mDEVs (blue dots) and mDEVs (green dots) by immature JAWS II cells, IC-21 macrophages, and HUVEC cells.
Figure 14:
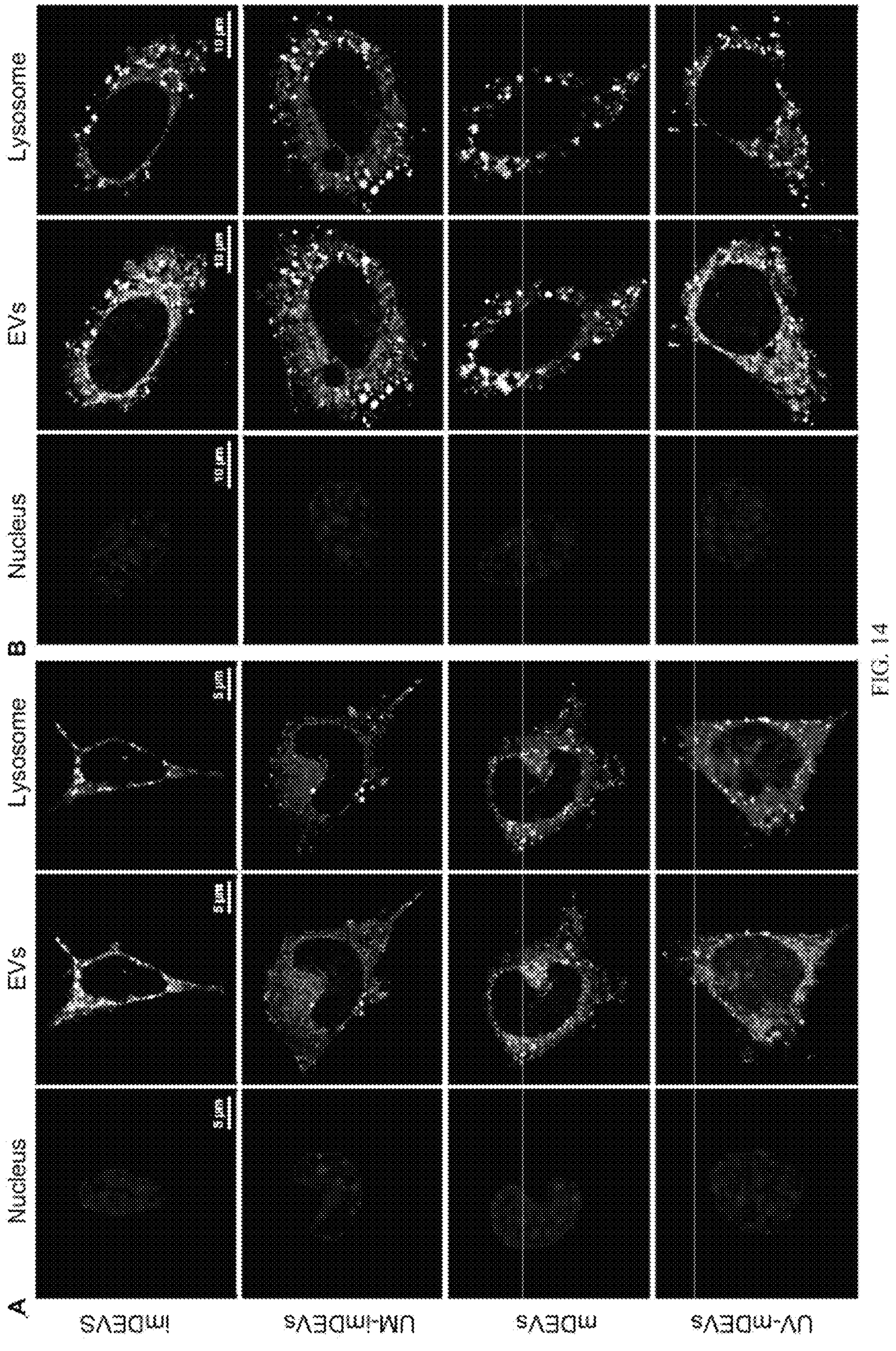
FIG. 14. Confocal microscope images of immature IC-21 cells (a) and HUVEC cells (b) treated with different PKH-67-labeled EVs (green) for 1 h, cells are also labeled with lysosomal tracker (red) and blue indicates nucleus.

Due to the significance of surface properties and receptors in controlling the EV internalization process (Mulcahy L A et al. "Routes and mechanisms of extracellular vesicle uptake," J Extracell Vesicles 3(2014)), studying the cellular internalization of light promoted DC-EVs can precisely evaluate the integral quality and immunological viability for use as a well-controlled therapeutic platform. Currently, the most recognized cellular internalization pathways for EVs are receptor- and raft-mediated endocytosis, phagocytosis, micropinocytosis, and membrane fusion (McKelvey K J et al. "Exosomes: Mechanisms of Uptake," J Circ Biomark 4:7 (2015); Gonda A et al. "Internalization of Exosomes through Receptor-Mediated Endocytosis," Mol Cancer Res 17(2): 337-347 (2019); Feng D et al. "Cellular internalization of exosomes occurs through phagocytosis," Traffic 11(5):675-87 (2010); Franzen C A et al. "Characterization of uptake and internalization of exosomes by bladder cancer cells," Biomed Res Int 2014:619829 (2014)). We investigated the cellular internalization of light promoted DC-EVs using both immune cells (immature JAWS II and IC-21 macrophages) and non-immune cells (HUVEC cells), compared with native DC-EVs as the control group (FIG. 13-14). For the early stage of uptake at 1 h, all DC-EVs were internalized by the three types of cells regardless of the producing DC cell conditions or light treatment conditions (FIG. 13). By tracking the lysosomes, the most internalized DC-EVs were in early endosomes and a few were partially colocalized within the lysosomes. DC-EVs could be internalized through multiple routes including endocytosis, phagocytosis, and membrane fusion (He F et al. "Probing exosome internalization pathways through confocal microscopy imaging," Chem Commun (Camb) 55(93):14015-14018 (2019); Tian T et al. "Dynamics of exosome internalization and trafficking," J Cell Physiol 228(7):1487-95 (2013)). In order to quantitatively evaluate the light-promoted DC-EVs in terms of their internalization behavior compared to native DC-EVs, we used scatterplot analysis to assess the dispersion degree between red fluorescence tracking lysosomes and green fluorescence tracking DC-EVs. After internalization by immature JAWS II cells, both UV-imDC EVs and UV-mDC EVs exhibited the same dispersion degree as their control imDC EV and mDC EVs groups, respectively (FIG. 13D). Similarly, we did not observe noticeable differences between light-promoted DC-EVs and native DC-EVs for internalization by IC-21 macrophages and HUVEC cells (FIG. 13D). Overall, these results validated that the internalization of light-promoted DC-EVs by either immune cells or non-immune cells are comparable to native DC-EVs, which indicates the high integral quality and immunological viability of light-promoted DC EVs.

4. LIGHT PROMOTED DC-EVS ARE HIGHLY BIOCOMPATIBLE AND IMMUNE FUNCTIONAL

Figure 15A:
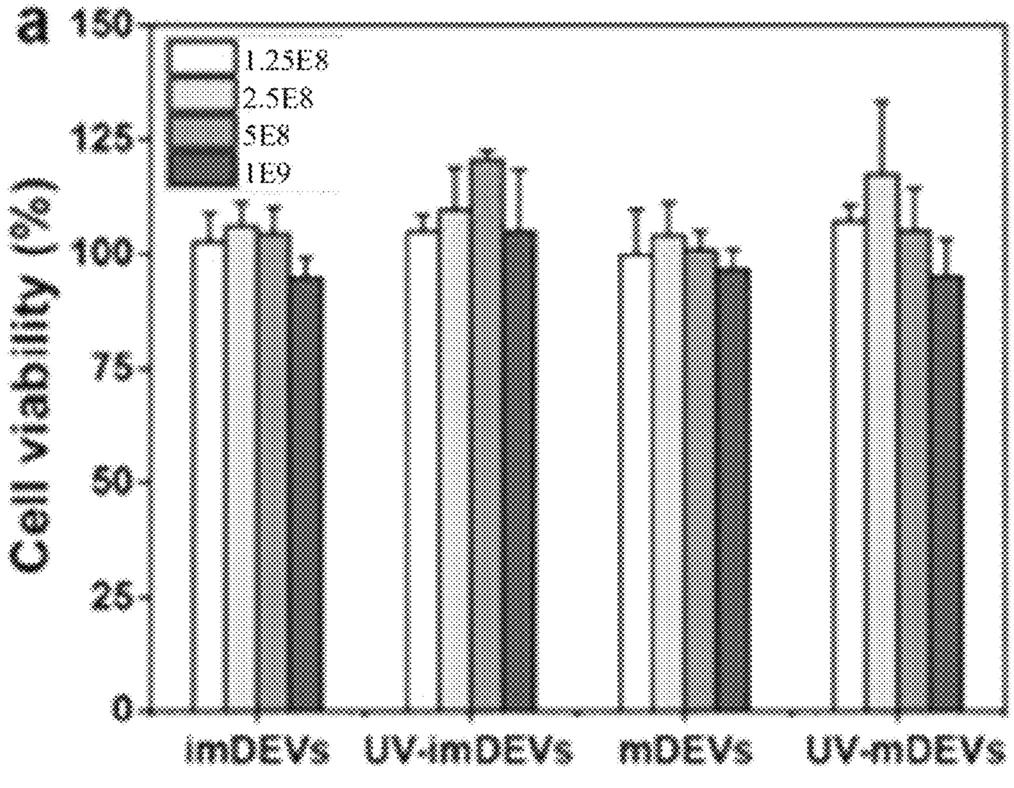
FIG. 15A. In vitro evaluation of biocompatibility and cellular uptake behavior of light-promoted DEVs. Cell viability analysis of imDCs incubated with light-promoted and native DEVs with dose titrations for 72 h (n=5).
Figure 16:
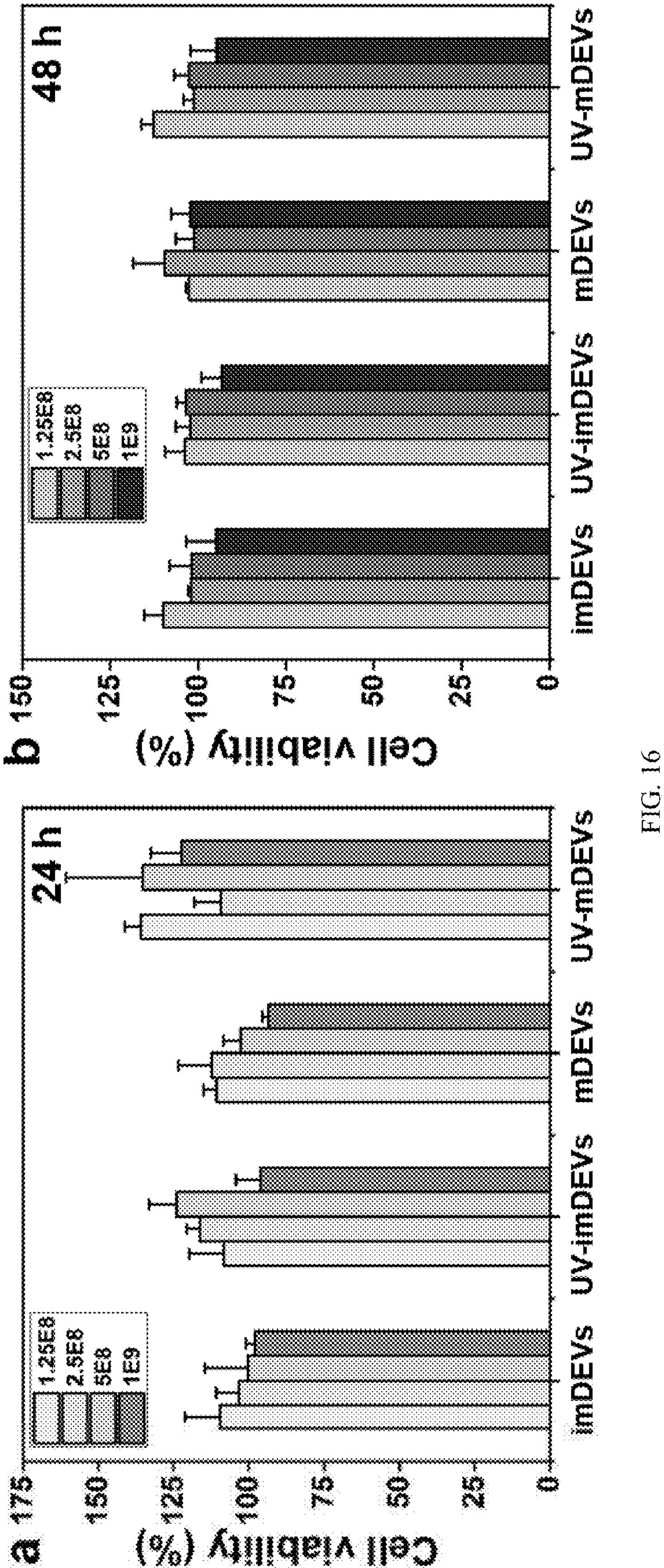
FIG. 16. Cell viability of immature JAWS II cells after treatment with different EVs under titration dose for 24 h (a) and 48 h (b).
Figure 18:
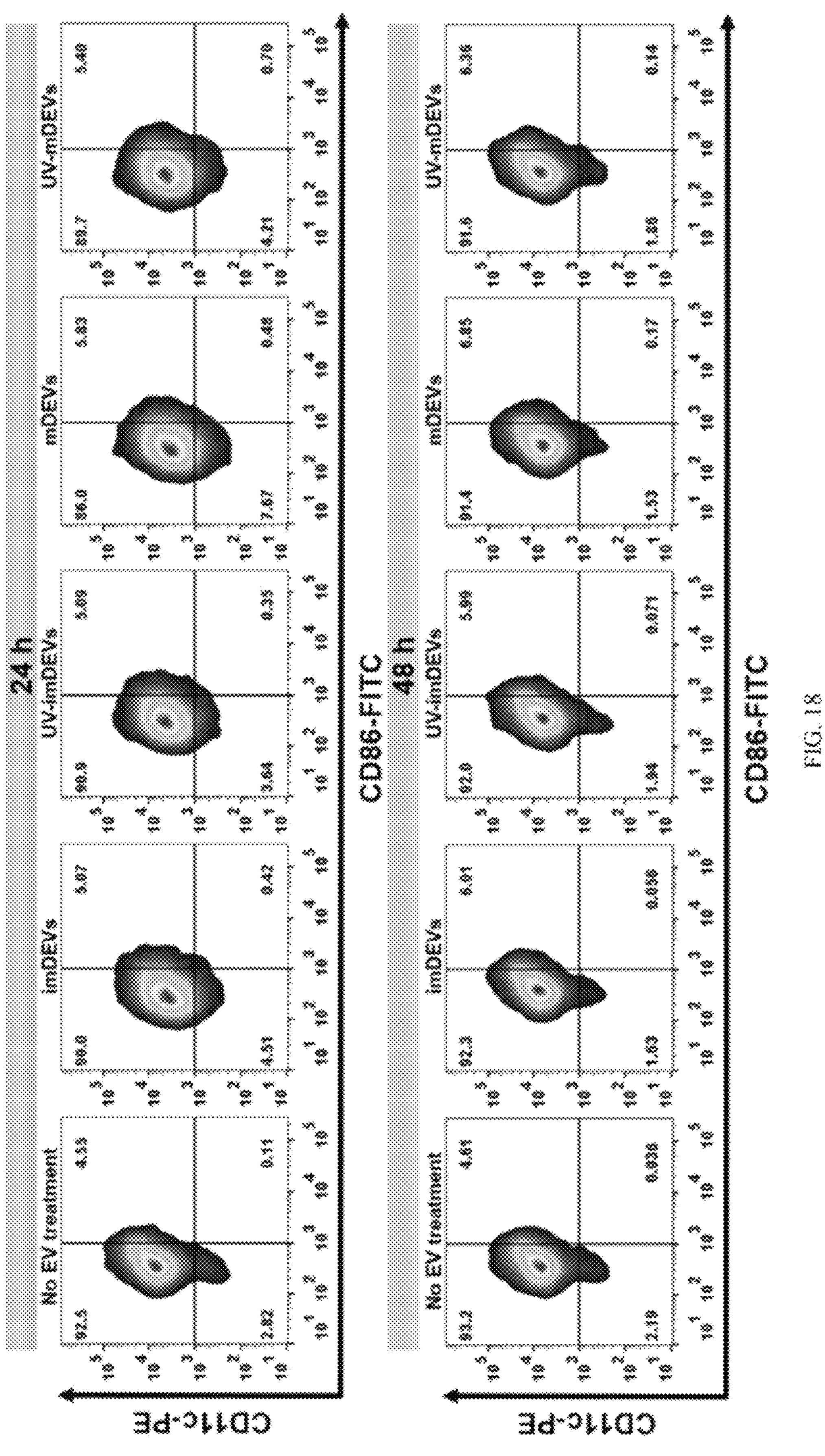
FIG. 18. Representative flow cytometry analysis of imDCs treated with different EVs for 24 h and 48 h, cells were immunofluorescence stained with PE-conjugated anti-mouse CD11c antibody and AF488-conjugated anti-mouse CD86 antibody.
Figure 19:
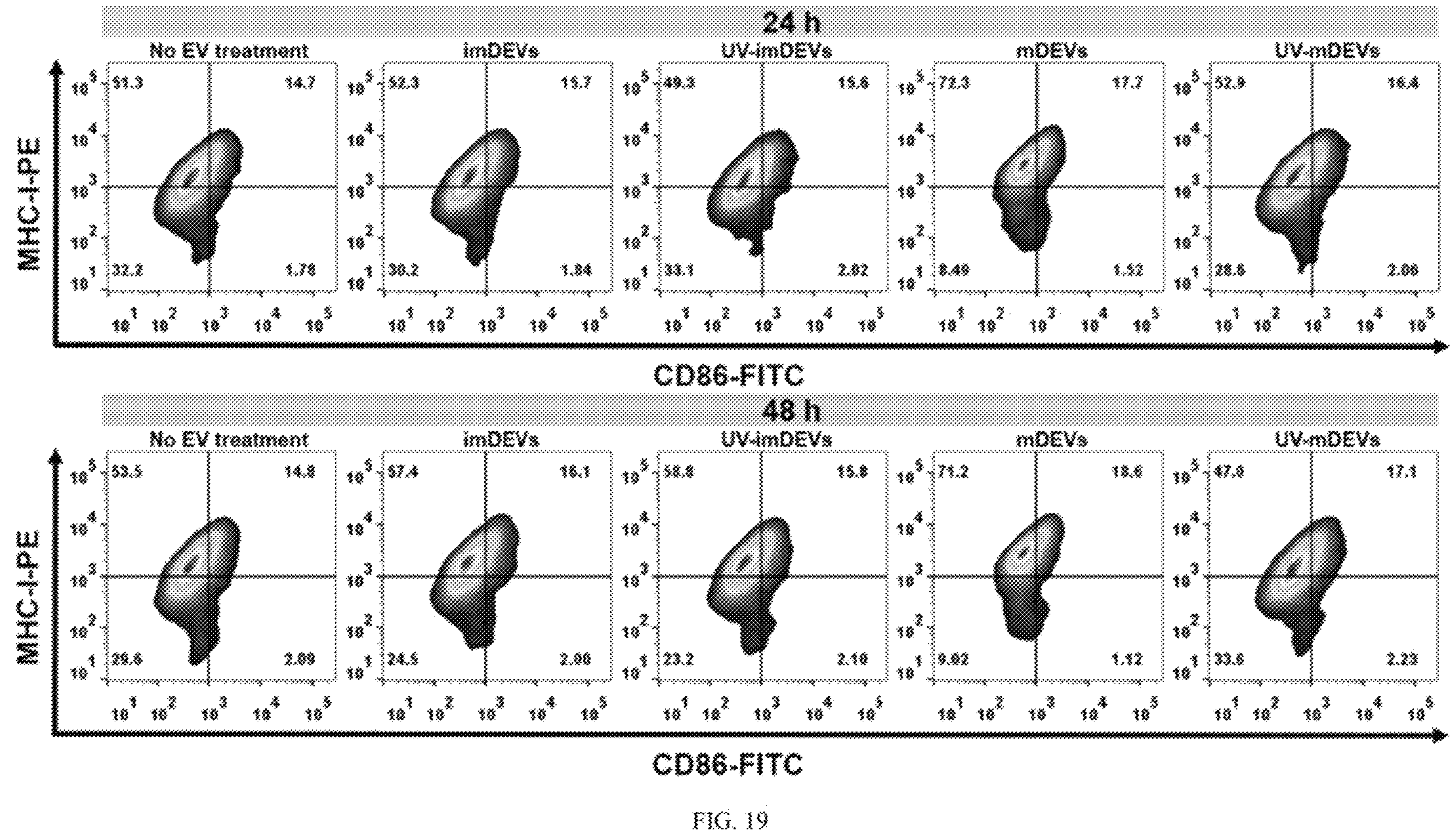
FIG. 19. Representative flow cytometry analysis of imDCs treated with different EVs for 24 h and 48 h, cells were immunofluorescence stained with PE-conjugated anti-mouse MHC-I antibody and AF488-conjugated anti-mouse CD86 antibody.
Figure 20:
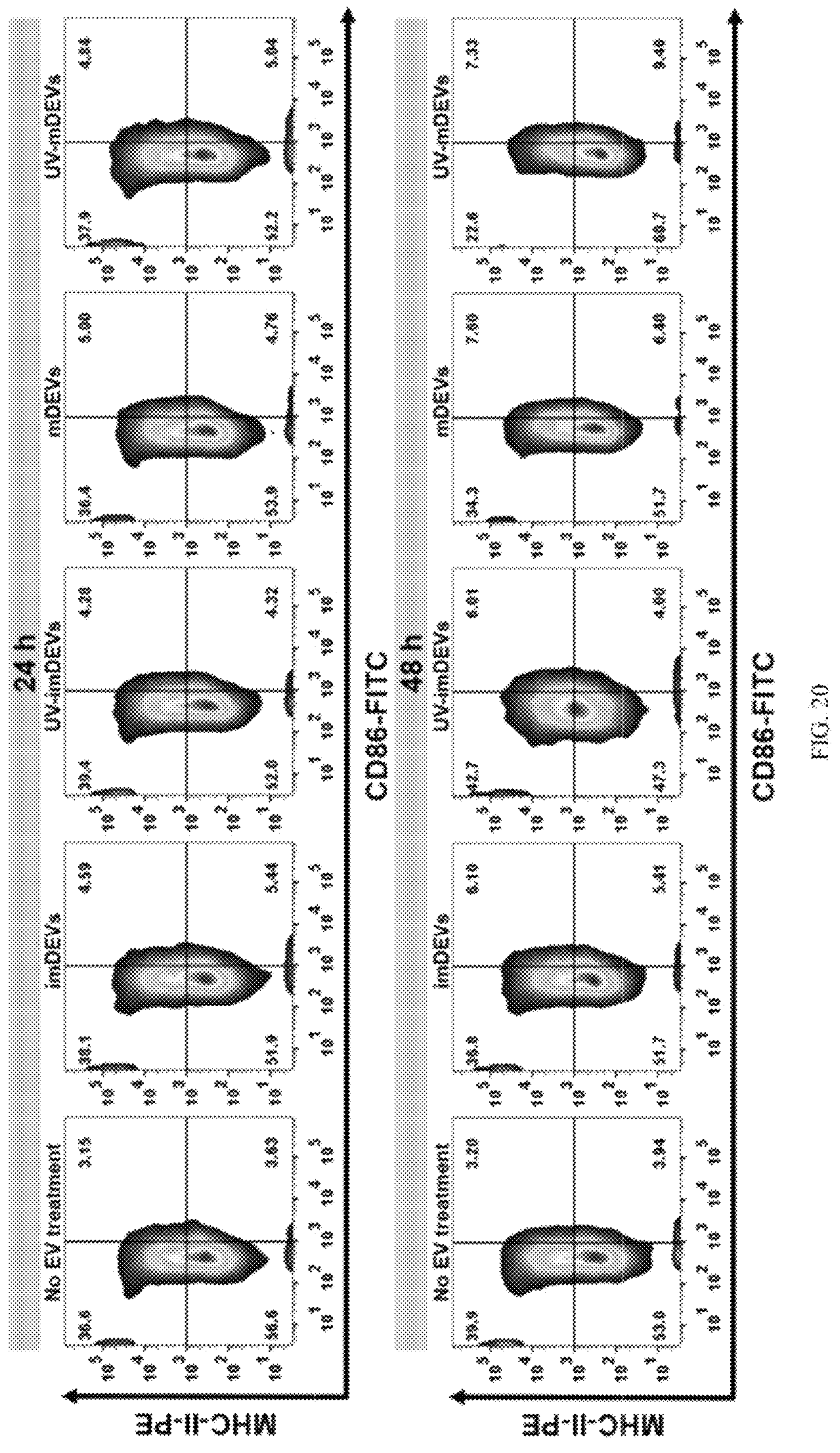
FIG. 20. Representative flow cytometry analysis of imDCs treated with different EVs for 24 h and 48 h, cells were immunofluorescence stained with PE-conjugated anti-mouse MHC-II antibody and AF488-conjugated anti-mouse CD86 antibody.

To evaluate the biocompatibility of light promoted DC-EVs, we conducted a MTT assay to assess cellular viability after incubating with DC-EVs from different production conditions. By titrating EV doses ranging from $1.25\times10^8$ to $1\times10^9$ for 24 h, 48 h, or 72 h incubation, all imDCs showed excellent viability larger than 90% regardless of incubation with light-promoted DC-EVs or native DC-EVs (FIG. 15A FIG. 6), which was not affected by incubation time as we tested after 24 h and 48 h (FIG. 16). Light promoted DC-EVs, either from mature or immature conditions, led to slightly higher cell viability across all dose ranges, indicating light-promoted DC-EVs possessed good biocompatibility for use in the in vivo applications.

Figure 15B:
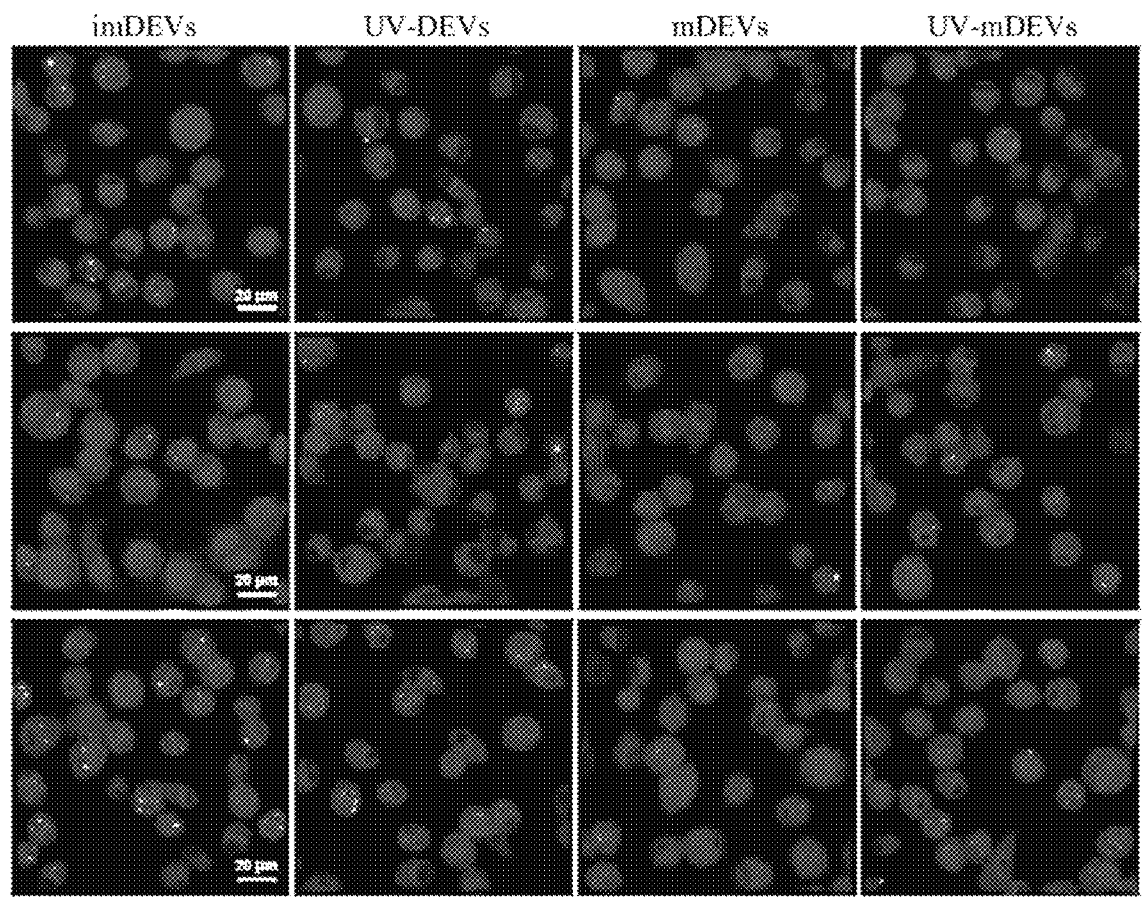
FIG. 15B. Confocal imaging of cellular uptake of light-promoted DEVs compared with native DEVs along time intervals between 1 h (top row), 2 h (middle row), and 4 h bottom row.

To investigate the cellular uptake kinetics and behavior of light promoted DC-EVs, we used confocal imaging to monitor the uptake rate of DC-EVs labeled with PKH-26, at time intervals of 1 h, 2 h, and 4 h. For the first 4 h, shown in FIG. 15B, the example, confocal images for internalizing UV-imDEVs and UV-mDEVs by imDCs exhibited similar increasing rates as their corresponding control groups without light treatment (imDEVs and mDEVs). However, after 4 h incubation until 24 hours, we noticed decreased uptake of UV-imDEVs, as well as mDEVs and UV-mDEVs, compared to imDEVs. Note that UV-imDEVs gave similar reduced uptake rate after 4 h as the mDEVs regardless of the light treatment conditions (FIG. 15C). It has been reported that EVs are more preferentially internalized by their origin parent cells (Jurgielewicz B J et al. "Kinetics and Specificity of HEK293T Extracellular Vesicle Uptake using Imaging Flow Cytometry," Nanoscale Res Lett 15(1):170 (2020)). Thus, native imDEVs were more preferentially internalized by their imDCs compared with mDEVs or light promoted DC-EVs. Additionally, EVs have been shown to either break down or release out after 24 h internalization. Therefore, longer incubation times may not accurately reflect EV internalization (Jurgielewicz B J et al. 2020), due to increased breakdown rate. In order to further validate our observation, we used IC-21 macrophage cells to uptake the same EV samples and observed similar uptake trends up to 24 h (FIG. 15D). The overall uptake from IC-21 macrophage cells was slower than imDCs, but has a significant about 3-fold higher uptake amount at 24 h. This trend follows the reported observation that slower first-order rate constant of EV uptake is correlated with higher total cellular uptake amount (Jurgielewicz B J et al. 2020).

Figure 21:
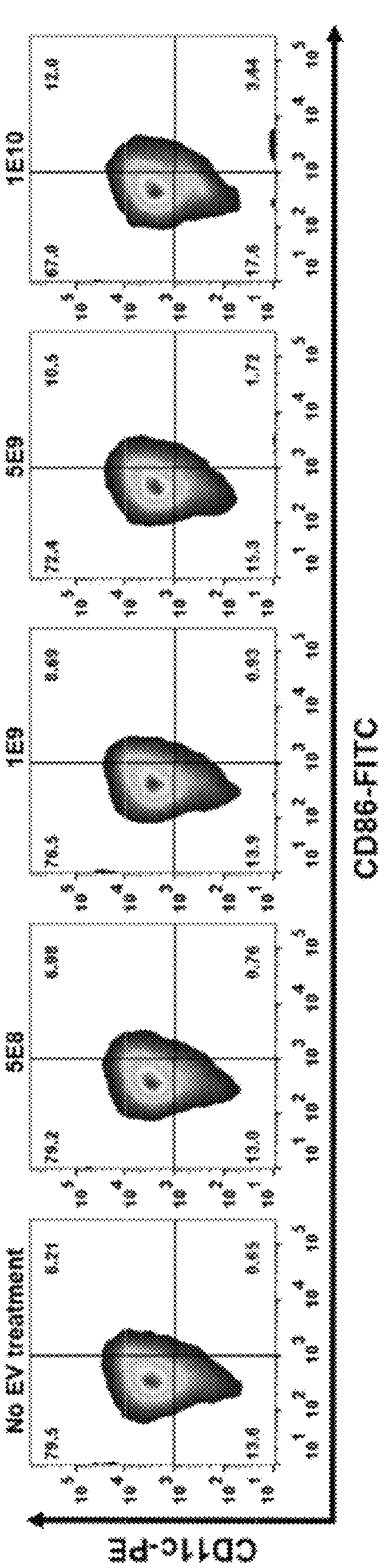
FIG. 21. Representative flow cytometry analysis of imDCs treated with near UV-mDEVs under titration dose for 24 h, cells were immunofluorescence stained with PE-conjugated anti-mouse CD11c antibody and AF488-conjugated anti-mouse CD86 antibody.

In order to further assess the immunomodulatory function from light-promoted DC-EVs in eliciting cellular level response, we used flow cytometry to investigate several important immune surface marker expressions (CD11c, MHC-I, MHC-II, CD86) from imDC cells after uptaking EVs for 24 h, 48 h, 72 h). We noticed that after 72 h uptake of either UV-mDEVs or mDEVs, imDCs could be significantly elicited to express much higher immune functional markers (FIG. 17A-F, FIG. 18-20), indicating the stronger ability of both UV-mDEVs and mDEVs to stimulate in vitro cellular DC maturation. We did not observe noticeable differences from light promoted DC-EVs compared to native EVs, in terms of the ability for in vitro cellular level immunomodulation. We also monitored the cellular secretion of TNF-α from immature imDCs after uptaking different EV samples, which essentially indicates DC immune activity. At 72 h uptake, we observed both UV-mDEVs and mDEVs can significantly elicit TNF-α secretion from imDCs, with an about 1.5-fold increase compared to the group of imDEVs and a ~3-fold increase compared to the group of untreated DCs, indicating the higher immunomodulation potential of mDEVs compared to imDEVs (FIG. 17G-I) which is consistent with previous report (Quah B J et al. "The immunogenicity of dendritic cell-derived exosomes," Blood Cells Mol Dis 35(2):94-110 (2005)), regardless of light treatment conditions. Moreover, there was no noticeable difference between mDEVs and UV-mDC-EVs, suggesting the light-promoted DC-EVs did not exhibit alterations in their intrinsic immunological function compared to native DEVs. Additionally, flow cytometry analysis also validated that cellular immune marker expression ($CD11c^{+}CD86^{+}$) increased in a dose-dependent manner through incubation with UV-mDEVs (FIG. 21), indicating the direct correlation of cellular immune response with EV uptake.

5. LIGHT PROMOTED DC-EVS EXHIBIT NATIVE IN VIVO BIODISTRIBUTION AND IMMUNOGENICITY

Figure 22A:
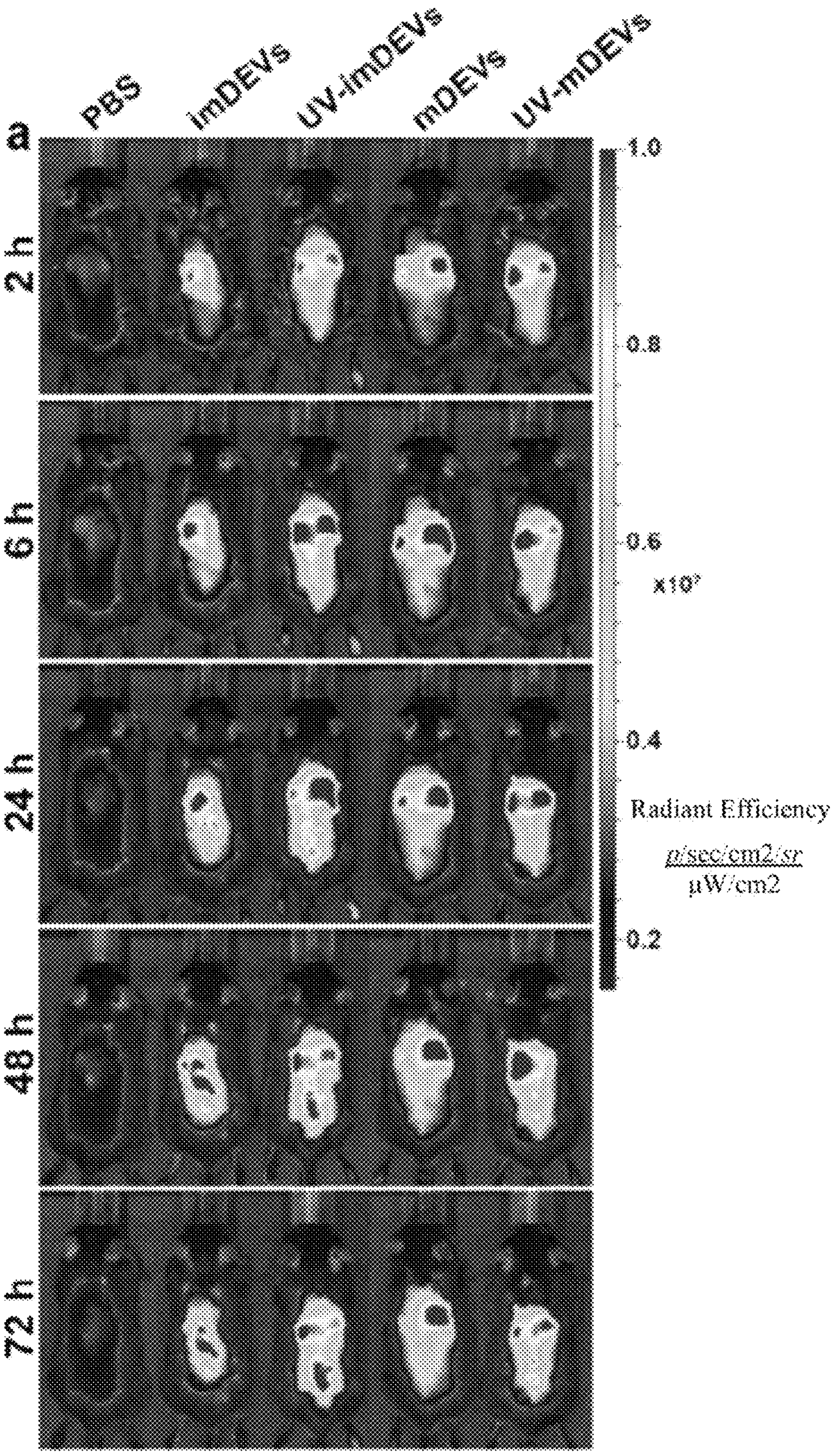
FIG. 22A. In vivo biodistribution analysis of light-promoted DC-EVs. In vivo living imaging of female C57BL6 mice at different time intervals after intravenous injection of DiR-labeled DC-EV samples. In vivo biodistribution analysis of light-promoted DEVs. Representative living in vivo imaging of male C57BL6 mice at different time intervals after intravenous injection of DiR-labelled DEV samples.
Figure 22B:
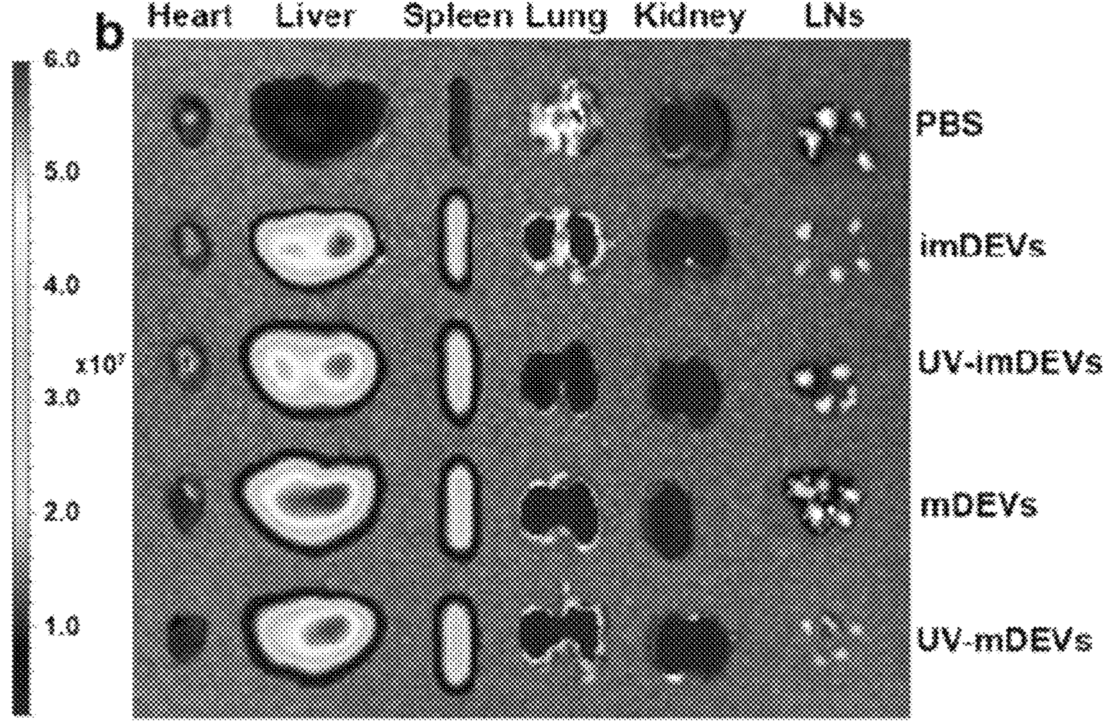
FIG. 22B. Ex vivo imaging of major organs harvested from healthy female mice sacrificed at 72 h post-injection. Ex vivo imaging of major organs harvested from healthy male mice sacrificed at 72 h post injection.
Figure 22C:
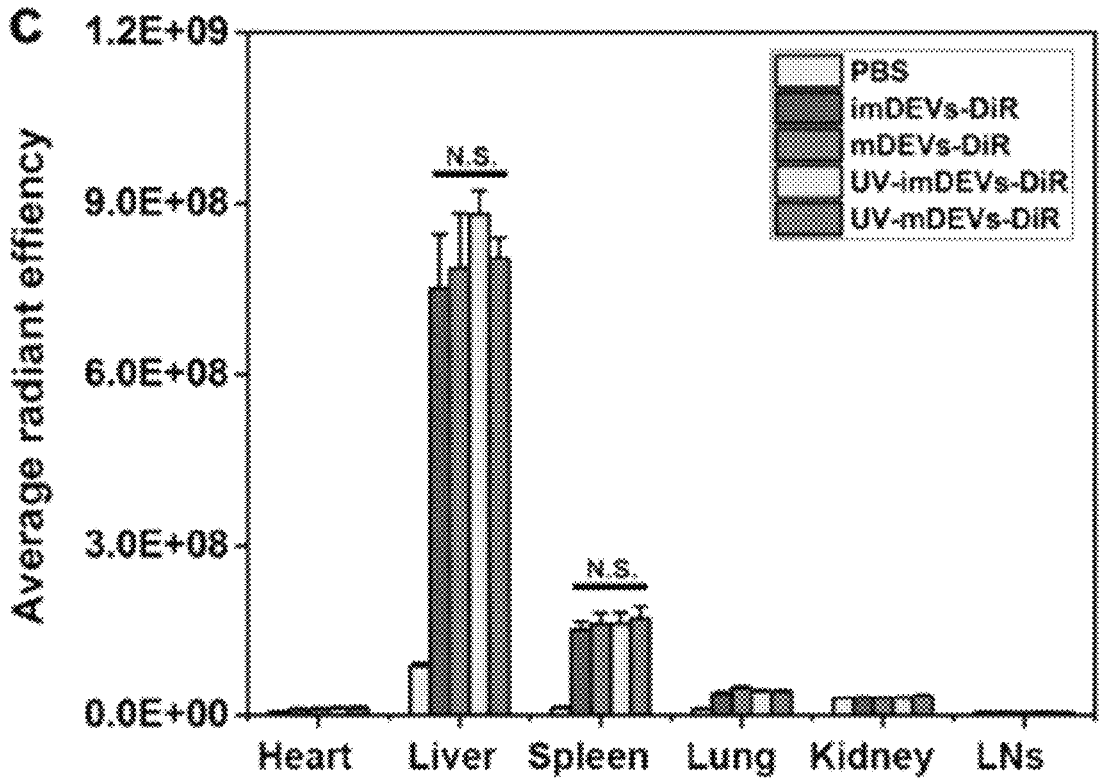
FIG. 22C. The average radiant efficiency (n=3) of different DiR-labeled DC-EV samples distributed in different organs from FIG. 22B *$p<0.0332$. The average radiant efficiency (n=3) of different DiR-labelled DEV samples distributed in different organs from FIG. 22Bb.
Figure 24A:
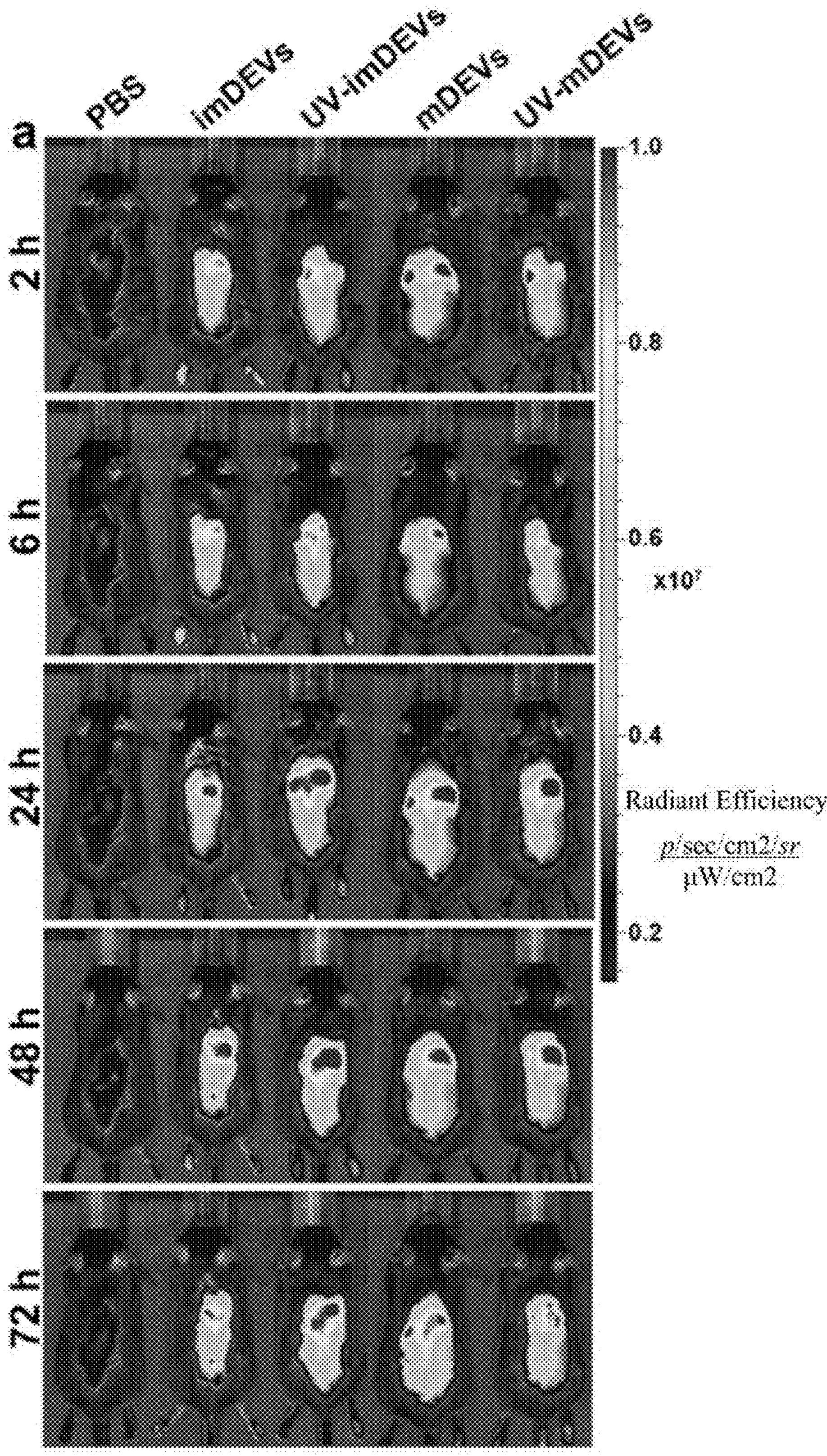
FIG. 24. In vivo biodistribution analysis of light-promoted DC-EVs. In vivo living imaging of female C57BL6 mice at different time intervals after intravenous injection of DiR-labeled DC-EV samples.
FIG. 24B. Ex vivo imaging of major organs harvested from healthy male mice sacrificed at 72 h post injection.
FIG. 24C. The average radiant efficiency (n=3) of different DiR-labelled DEV samples distributed in different organs from FIG. 22Bb.
Figure 24B:
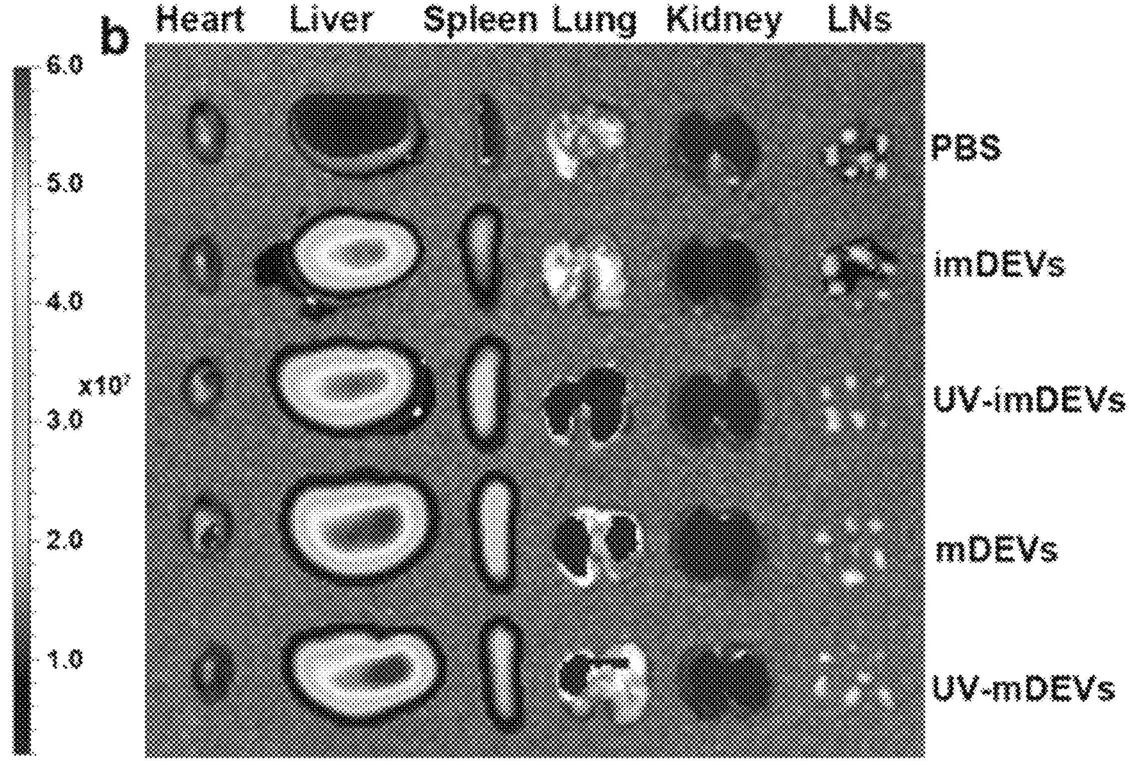
Figure 24C:
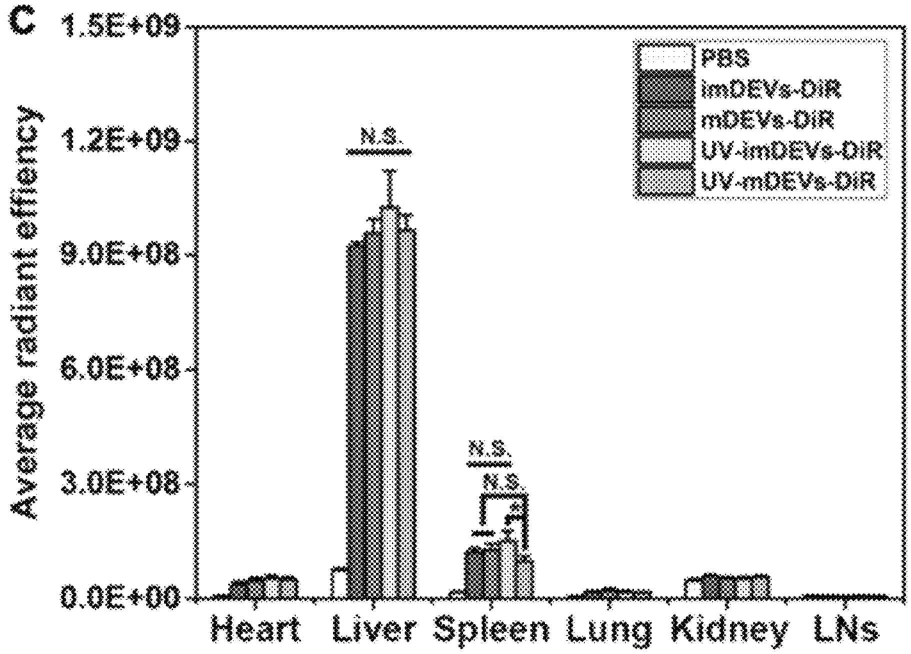

For safe and successful therapeutic development and clinical applications, understanding the light-promoted DC EV in vivo biodistribution profile, immunogenicity, and administration are critical. Therefore, we labeled different DC-EV samples with a near-infrared dye (DiR) and further evaluated their in vivo biodistribution in healthy male and female C57BL6 mice, respectively. Compared to the mice treated with PBS only, DC-EV treated mice groups showed much higher fluorescent signal 2 h post-injection (FIG. 22A). The fluorescent signals were mainly centered in the region of the liver and gradually spread, followed be a slight decrease at 72 h. To quantitively monitor the fluorescence distribution among organs, we harvested the major organs (heart, liver, spleen, lung, kidney, and lymph nodes) from mice post 72 h injection and performed ex vivo imaging (FIG. 22B). The results consistently showed strong distribution centered mainly in the liver and spleen over the heart, lung, kidney, and lymph nodes, regardless of treatment with light-promoted DC EVs or native DC EVs. The EVs either from immature DCs or mature DCs did not exhibit any differences neither. To investigate whether the gender of mouse will affect the biodistribution profile of these DC-EVs, we further performed the in vivo and ex vivo imaging parallelly using healthy female C57BL6 mice. The displayed biodistribution profile was consistent with that from male mice (FIG. 24). Overall results support that light-promoted DC EVs possess consistent in vivo biodistribution profile as the naturally derived DC-EVs, and they are well tolerated and can be safely administrated.

Figure 25:
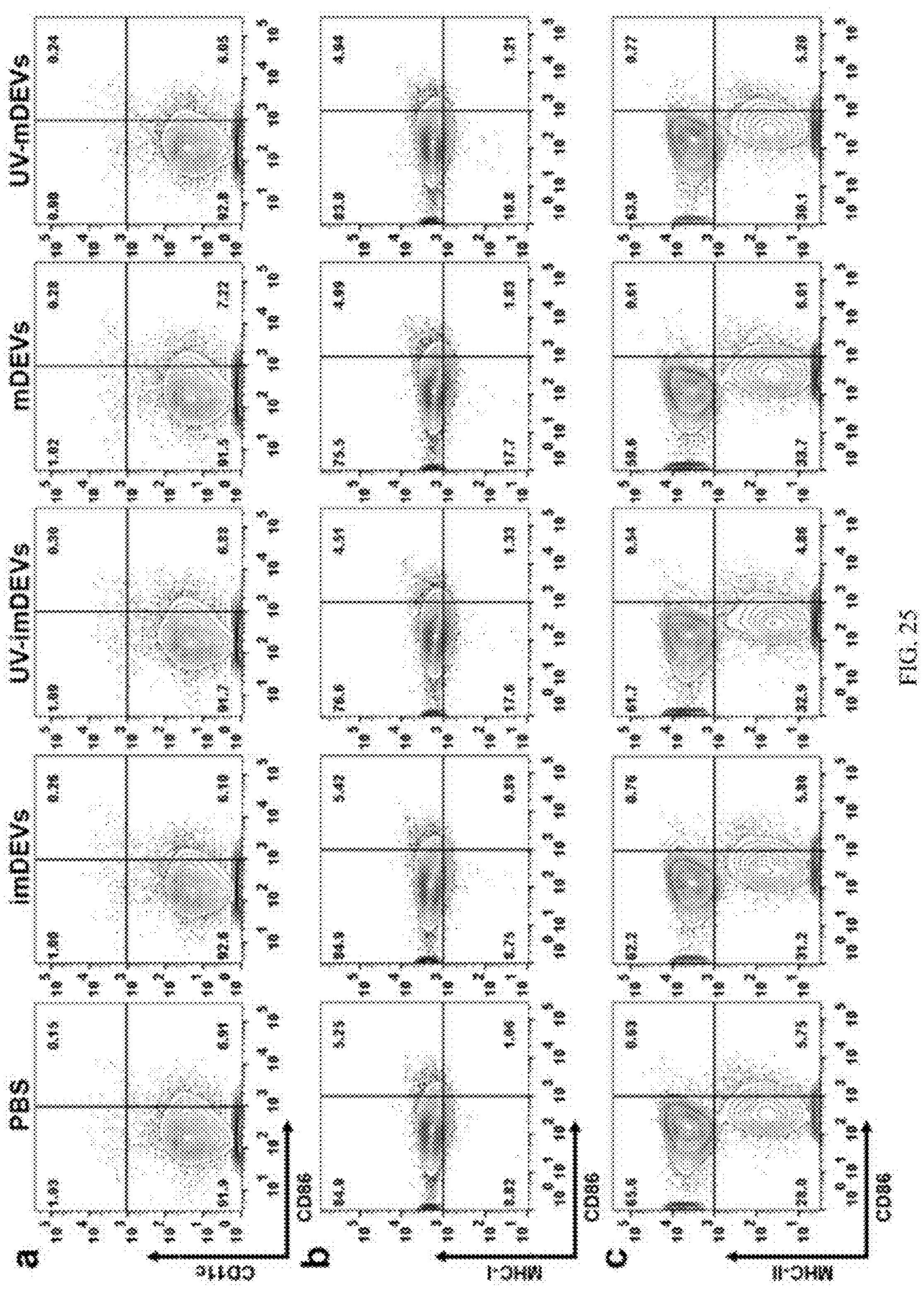
FIG. 25. Representative flow cytometry analysis of $CD11c^+CD86^+$ (a), $MHC\text{-}I^+CD86^+$ (b), and $MHC\text{-}II^+CD86^+$ (c) DCs in total lymphocytes from healthy mice at 72 h post injection with different DC-EV samples. The PBS injection group serves as the negative control.
Figure 26A:
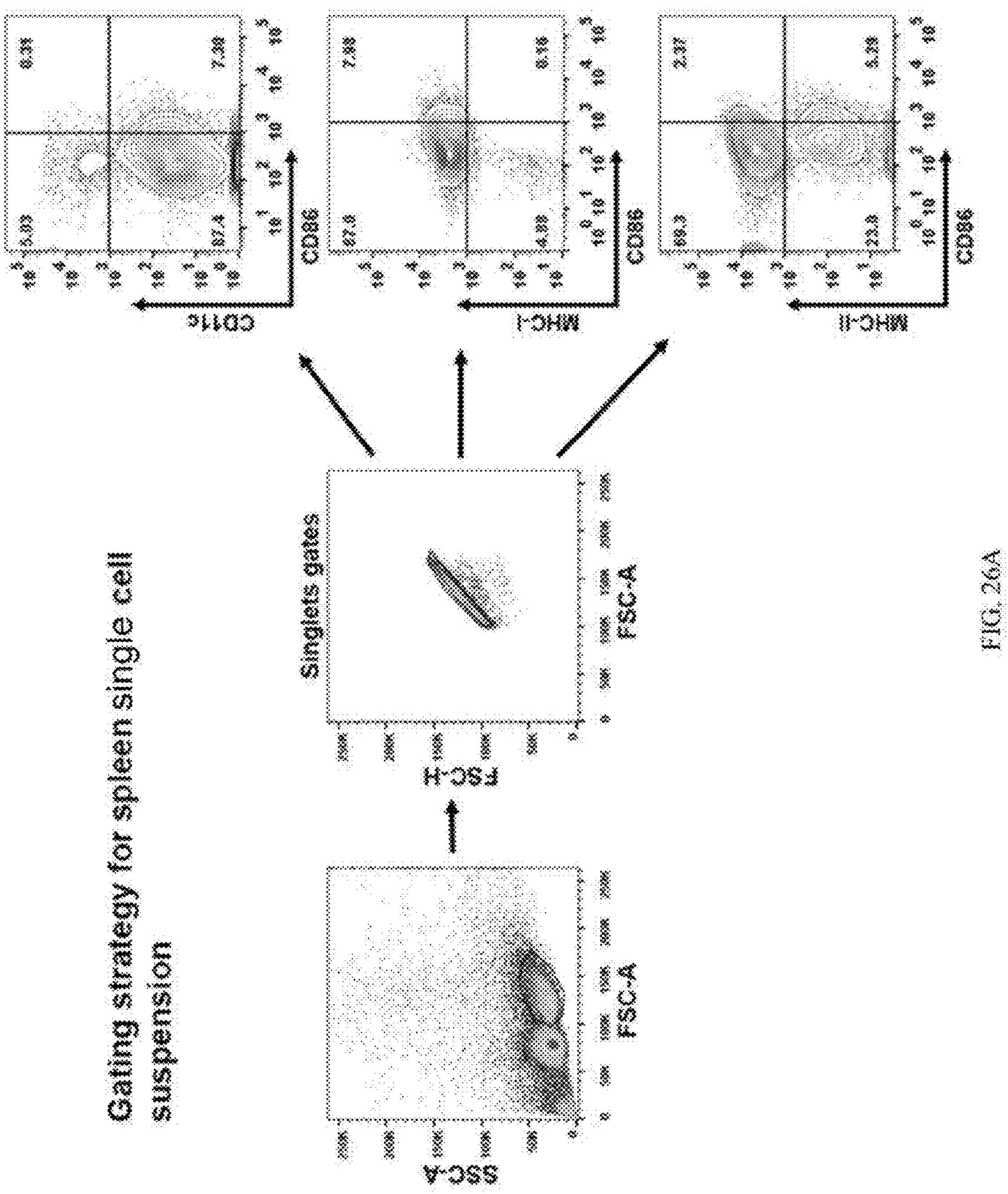
FIG. 26A. Gating strategy for flow cytometry analysis of total splenocytes.
Figure 26B:
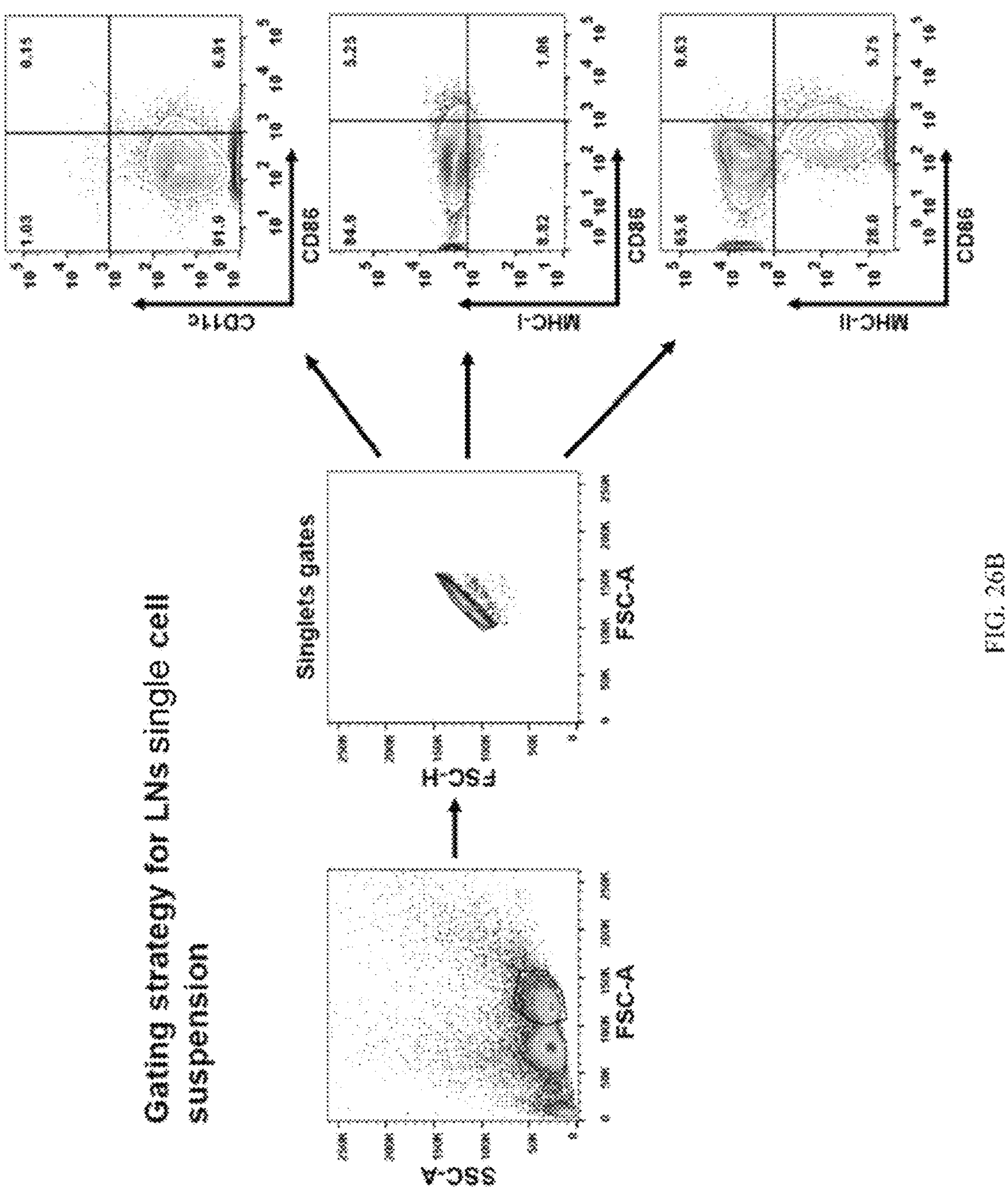
FIG. 26B. Gating strategy for flow cytometry analysis of lymphocytes.

As primary peripheral lymphoid organs, spleen and LNs play an important role in governing the immune response against foreign substances. Therefore, we further investigated the in vivo immunogenicity of these DC-EVs by monitoring immune marker expression from spleen and LNs derived total splenocytes and lymphocytes at 72 h post injection, using flow cytometry analysis. The expression levels of $CD11c^{+}CD86^{+}$ (FIG. 23A), $MHC\text{-}I^{+}CD86^{+}$ (FIG. 23B), MHC-II $CD86^{+}$ (FIG. 23C) in total splenocytes between native and light promoted DC EV groups did not show noticeable differences. Meanwhile, both mature and immature DC EV groups also exhibited similar immune marker expressions from both total splenocytes (FIG. 23D) and lymphocytes (FIG. 23E, FIG. 25), which is comparable to the PBS treated negative control group. The corresponding gating strategy for flow cytometry analysis of splenocytes and lymphocytes was provided in Supporting Information (FIG. 26). This result strongly supports that light-promoted DC-EVs are well tolerated, with no immunogenic concerns and are well suited to serve as natural drug delivery carriers. TNF-α secretion levels in the serum 72 h post mice intravenous injection, showed a slight increase after treatment with these DC-EV samples compared to the negative control group treated with PBS only. Such slight elicitation on TNF-α secretion may be may due to the import of TNF-α intrinsically carried by DC-EVs (FIG. 23F). Although the in vitro cellular level study showed significant differences in TNF-α secretion between imDEVs and mDEVs, the in vivo system is more tolerant. Collectively, we validated that light-promoted DC-EVs possess as little or no immunogenicity as their native DEVs. The light-promoted DC-EVs are suitable for use in therapeutic delivery, therapy development, and as therapeutic agents and as drug delivery carriers. The light-promoted DC-EVs exhibit excellent tolerance like the native DC-EVs without safety concerns, while having more than 13-fold higher production rate. MHC molecules, co-stimulatory molecules, and cytokines, the light-promoted DC EVs are not only suitable for developing drug delivery system, but also for vaccine or immunotherapy development.

6. CONCLUSION AND DISCUSSION

The use of EVs as alternative drug delivery system has gained tremendous interests, due to their intrinsic properties, such as natural cellular origin, good biocompatibility and safety, stable and long circulation time in human body, versatile regulatory functions, and excellent targeting ability (Elliott R O et al. "Unlocking the Power of Exosomes for Crossing Biological Barriers in Drug Delivery," Pharmaceutics 13(1) (2021); Liang Y et al. "Engineering exosomes for targeted drug delivery," Theranostics 11(7):3183-3195 (2021)). However, due to the limited cellular production rate, harvesting good quality of EVs at the scale has previously been a bottleneck challenge for clinical translation. Our study explores a new opportunity using light stimulation for parent DC cells to produce immune functional DC-EVs efficiently, with more than 13-fold enhancement in production rate, while remaining good integral quality, biocompatibility, cellular internalization ability, and immunogenicity. Under our optimized light treatment condition, the method is very simple, straightforward, low cost, and generic for promoting other cell types. The protocols can be easily adapted into the cell culture incubators or bioreactors on demand at manufacturing scale. We conducted a series of quality validation of light-promoted DC-EVs, in terms of size, zeta potential, morphology, immune surface markers and cytokines, biocompatibility, ROS production, cellular uptake behavior, and immune-modulation ability on eliciting cellular responses, as well as their cellular internalization behavior. We also validated the biodistribution, immunogenicity, and administration safety using light-promoted DC-EVs in mice model from both male and female genders. Taken together, the data supports that light promoted DC-EVs are in excellent quality, high biocompatibility, and immune functional for serving as ideal therapeutic platform with scalable production.

Despite EV-based therapeutic and diagnostic applications have been intensively explored, the in-depth understanding of DC-EVs and their immune functions during the production process with light induction has not been investigated elsewhere. Our study provides the necessary quantitative information for evaluating light promoted DC-EVs, and correlating their immune surface marker expressions (MHC-I, MHC-II, CD86), cytokine deposit (TNF-$\alpha$) and EV generic surface marker expressions (CD63, CD9, CD81) with cellular production parameters. The co-expression levels of those markers measured by NanoView analysis also provide precision immune profiles on light-promoted DC-EVs for quantitative therapeutic assessment. The in vivo biodistribution and immunogenicity study also demonstrated no significant differences between light-promoted DC-EVs and native DC-EVs, which proves the strong feasibility for using near UV light induction for promoting high-rate production of DC-EVs in therapeutic development.

It has been reported that UVB irradiation (280-315 nm) could elevate cellular oxidative pressure and secret EVs for communicating protective messages during oxidative stress (Shen Z et al. "Ultraviolet B irradiation enhances the secretion of exosomes by human primary melanocytes and changes their exosomal miRNA profile," PLOS One 15(8): e0237023 (2020); Liu J et al. "UV cell stress induces oxidative cyclization of a protective reagent for DNA damage reduction in skin explants," Free Radic Biol Med 134:133-138 (2019)). Our light induction wavelength is far from UVB at 365 nm. We observed that 365 nm light treatment at the level employed does not increase ROS production for activating the cellular oxidative stress pathway. Using the described methods, (including 0.096 W/cm2 for 30 min), cells produced good quality EVs. Without wishing to be bound by theory, it is possible that increased oxidative stress of parent cells may in turn promote the EV secretion. As described above and shown in FIG. 6, treatment of cells with 4.0 W/cm$^2$ partially reduced cell viability. Cells treated with lower intensity near UV light retained high viability and were able to recover and reach to 90-100% confluency in 6 days for passaging and subculture.

The invention claimed is:

1. A method for producing extracellular vesicles comprising: exposing at least one cell to near UV-visible light, wherein intensity of light exposure on the cells is about 0.05 W/cm$^2$ to about 0.25 W/cm$^2$, wherein exposing the at least one cell to near UV-light increases production of extracellular vesicles from the at least one cell.

2. The method of claim 1, wherein the near UV-visible light comprises light having a wavelength of:

(a) about 315 nm to about 750 nm;
(b) about 315 nm to about 500 nm;
(c) about 340 nm to about 390 nm;
(d) about 365 nm;
(e) about 405 nm;
(f) about 488 nm; or
(g) about 670 nm.

3. The method of claim 1, wherein the cell is exposed to a lamp producing light at an intensity of:

(a) about 0.1 mW/cm$^2$ to about 10 W/cm$^2$;
(b) about 1 to about 10 W/cm$^2$;
(c) 2.4±0.6 W/cm$^2$; or
(d) 2.4±0.2 W/cm$^2$.

4. The method of claim 1, wherein the cell is exposed to a lamp positioned:

(a) about 1 to about 20 cm from the cell;
(b) 10±5 cm from the cell; or
(c) 10±1 cm from the cell.

5. The method of claim 1, wherein the cell is exposed to a lamp producing light at an intensity of about 2.4 W/cm$^2$, and wherein the lamp is positioned about 10 cm from the cell.

6. The method of claim 1, wherein the cell is exposed to the near UV-visible light at an intensity of (a) about 0.064 W/cm$^2$ to about 0.16 W/cm$^2$; or
(b) about 0.096 W/cm$^2$.

7. The method of claim 6, wherein the near UV-visible light has a wavelength of about 365 nm.

8. The method of claim 6, wherein the cell is exposed to the near UV-visible light for a duration of (a) about 5 to about 45 minutes;
(b) 30±10 minutes; or
(c) 30 minutes.

9. The method of claim 1, wherein the cell comprises a mammalian cell, an immune cell, an antigen presenting cell, a T cell, a stem cell, an endothelial cell, a primary cell, or a cell line cell.

10. The method of claim 9, wherein (a) the antigen presenting cell comprises a dendritic cell, an immature dendritic cell, a mature dendritic cell, a macrophage, or a B cell; or (b) the dendritic cell comprises a bone marrow derived dendritic cell.

11. The method of claim 10, wherein the dendritic cell comprises a mammalian dendritic cell, a mouse dendritic cell, a rat dendritic cell, a rabbit dendritic cell, a pig dendritic cell, a sheep dendritic cell, a non-human primate dendritic cell, a human dendritic cell, a horse dendritic cell, a bovine dendritic cell, a dog dendritic cell, or a cat dendritic cell.

12. The method of claim 1, wherein the extracellular vesicles are immune functional and/or contain one or more of: TNF-α, MHC-I, MHC-II, CD86, CD9, and CD63.

13. The method of claim 1, wherein the cell expresses one or more therapeutic or targeting proteins or polypeptides.

14. The method of claim 1, wherein the cell is modified to contain one or more therapeutic or targeting molecules prior to exposure to the near UV-visible light.

15. The method of claim 1, further comprising collecting the extracellular vesicles produced from the at least one cell.

16. The method of claim 15, further comprises loading the extracellular vesicles with one or more therapeutic molecules.

17. An extracellular vesicle made by the process of claim 1.

18. The extracellular vesicle of claim 17, for use in (a) delivering or providing a therapeutic treatment to a subject;

(b) stimulating an immune response in the subject;

(c) inducing an immune response against a cancer; or (d) vaccinating the subject against a pathogen.

19. A method of providing therapeutic extracellular vesicles to a subject comprising: exposing at least one cell to near UV light to induce production of extracellular vesicles; isolating the extracellular vesicles; optionally loading the extracellular vesicles with one or more therapeutic molecules, and administering the extracellular vesicles to the subject.

20. A method of immunotherapy comprising: exposing at least one cell containing or expressing a therapeutic polypeptide or nucleic acid to near UV light to induce production of extracellular vesicles; isolating the extracellular vesicles; optionally loading the extracellular vesicles with one or more therapeutic molecules, and administering the extracellular vesicles to the subject.

* * * * *